(12) United States Patent
Taylor et al.

(10) Patent No.: US 7,888,335 B2
(45) Date of Patent: *Feb. 15, 2011

(54) MITOQUINONE DERIVATIVES USED AS MITOCHONDRIALLY TARGETED ANTIOXIDANTS

(75) Inventors: Kenneth Martin Taylor, Auckland (NZ); Robin A. J. Smith, Dunedin (NZ)

(73) Assignee: Antipodean Pharmaceuticals, Inc., Menlo Park, CA (US)

( * ) Notice: Subject to any disclaimer, the term of this patent is extended or adjusted under 35 U.S.C. 154(b) by 673 days.

This patent is subject to a terminal disclaimer.

(21) Appl. No.: 10/568,655

(22) PCT Filed: Aug. 23, 2004

(86) PCT No.: PCT/NZ2004/000196

§ 371 (c)(1),
(2), (4) Date: Aug. 31, 2006

(87) PCT Pub. No.: WO2005/019232

PCT Pub. Date: Mar. 3, 2005

(65) Prior Publication Data

US 2008/0161267 A1      Jul. 3, 2008

(30) Foreign Application Priority Data

Aug. 22, 2003 (NZ) .................................. 527800
Oct. 23, 2003 (NZ) .................................. 529153
Jun. 14, 2004 (NZ) .................................. 533556

(51) Int. Cl.
*A01N 43/04* (2006.01)
*A61K 31/715* (2006.01)

(52) U.S. Cl. ........................... 514/58; 514/125; 568/11; 435/243

(58) Field of Classification Search .................. 514/58, 514/125; 435/243; 568/11
See application file for complete search history.

(56) References Cited

U.S. PATENT DOCUMENTS

| | | | |
|---|---|---|---|
| 3,532,667 A | 10/1970 | Singh et al. | 524/99 |
| 6,133,322 A | 10/2000 | Rustin et al. | 514/689 |
| 6,331,532 B1 * | 12/2001 | Murphy et al. | 514/100 |
| 6,673,908 B1 | 1/2004 | Stanton, Jr. | |
| 6,825,179 B2 | 11/2004 | Nielsen et al. | |
| 6,861,447 B2 | 3/2005 | Moldenhauer et al. | |
| 7,109,189 B2 | 9/2006 | Murphy et al. | |
| 7,179,928 B2 * | 2/2007 | Smith et al. | 552/303 |
| 7,232,809 B2 * | 6/2007 | Murphy et al. | 514/100 |
| 2002/0052342 A1 | 5/2002 | Murphy et al. | 514/75 |
| 2003/0069208 A1 | 4/2003 | Murphy et al. | 514/75 |
| 2004/0106579 A1 | 6/2004 | Murphy et al. | 514/75 |
| 2006/0229278 A1 | 10/2006 | Taylor et al. | |
| 2007/0238709 A1 | 10/2007 | Murphy et al. | 514/183 |
| 2007/0270381 A1 | 11/2007 | Murphy et al. | 514/100 |
| 2008/0275005 A1 | 11/2008 | Murphy et al. | |
| 2009/0258841 A1 | 10/2009 | Murphy et al. | |

FOREIGN PATENT DOCUMENTS

| | | |
|---|---|---|
| EP | 0 289 223 A1 | 11/1988 |
| EP | 5356036 B1 | 4/1993 |
| EP | 0535283 A1 | 11/1993 |
| EP | 549366 | 4/1998 |
| JP | 59-39855 | 3/1984 |
| JP | 03074395 A | 3/1991 |
| JP | 5-310763 | 11/1993 |
| JP | 7-223991 | 8/1995 |
| JP | 8-239340 | 9/1996 |
| JP | 2002104922 A | 4/2002 |
| JP | 2003520827 T | 7/2003 |
| JP | 09-278770 | 9/2006 |
| NZ | 513547 | 1/2003 |
| WO | 91/19815 A1 | 12/1991 |
| WO | 95/26973 A1 | 10/1995 |
| WO | 99/26582 A2 | 6/1999 |
| WO | 99/26954 A1 | 6/1999 |
| WO | 03/016323 | 2/2003 |
| WO | 03/065882 A2 | 8/2003 |
| WO | 2005/019233 A1 | 3/2005 |
| WO | 2005019232 A1 | 3/2005 |
| WO | 2009145982 A1 | 12/2009 |

OTHER PUBLICATIONS

Beg et al, Spectroscopic studies of organophosphorus compounds, 1986, Pakistan J. of Scientific and Industrial Research, 29(3), 165-171, See abstract.*

Saretzki et al., MitoQ counteracts telomere shortening and elongates lifespan of fibroblasts under mild oxidative stress, Aging Cell (2003), 2(2), 141-143.*

Kelso et al., Selective targeting of a redox-active ubiquinone to mitochondria within cells. Antioxidant and antiapoptotic properties, Journal of Biological Chemistry (2001), 276(7), 4588-4596.*

Smith et al., {.Delivery of bioactive molecules to mitochondria in vivo, Proceedings of the National Academy of Sciences of the United States of America (2003), 100(9), 5407-5412.*

(Continued)

*Primary Examiner*—Daniel M Sullivan
*Assistant Examiner*—Chukwuma O Nwaonicha
(74) *Attorney, Agent, or Firm*—Seed IP Law Group PLLC

(57) ABSTRACT

This invention relates to pharmaceutically acceptable amphiphilic antioxidant compounds, compositions and dosage forms comprising said compounds, and methods and uses reliant on said compounds. The exemplified compounds are all mitoquinone derivatives, being methoxyphenyl alkyl triphenylphosphonium or methoxy dioxocyclohexadiene alkyl triphenylphosphonium derivatives. The compounds, compositions, dosage forms, uses and methods are useful in, for example, the treatment of diseases or conditions associated with oxidative stress.

52 Claims, 20 Drawing Sheets

OTHER PUBLICATIONS

Burns, R., et al., "Labeling Of Mitochondrial Proteins In Living Cells By The Thiol Probe Thiobutyltriphenylphosphonium Bromide," Arch .Biochem .Biophys., 339(1):33-9, Mar. 1, 1997.

Burns, R., et al., "Synthesis and Characterization Of Thiobutyltriphenylphosphonium Bromide, A Novel Thiol Reagent Targeted To The Mitochondrial Matrix," Arch. Biochem. Biophys., 322(1):60-8, Sep. 10, 1995.

Chen, L.B., "Mitochondrial Membrane Potential in Living Cells," Annual Review of Cell Biology, 4:155-181, Nov. 1988.

Coulter et al., Mitochondrially targeted antioxidants and thiol Reagents, Free Radical Biology & Medicine (2000), 28(10), 1547-1554.

Davey, G.P., et al., "Uptake and accumulation of 1-methyl-4-phenylpyridinium by rat liver mitochondria measured using an ion-selective electrode," Biochem J., 288(Pt 2): 439-443, Dec. 1, 1992.

Dean., W., et al. "Mitochondrial Nutrition, Aging and Cognition,"Smart Drug News (5)2, Aug. 1, 1996.

Ernster, L. et al., "The mode of action of lipid-soluble antioxidants in biological membranes: relationship between the effect of ubiquinol and vitamin E as inhibitors of lipid peroxidation in submitochondrial particles," BioFactors 3(4): 241-248 1992.

Everett, S., et al., "Scavenging Of Nitrogen Dioxide, Thiyl, And Sulfonyl Free Radicals By The Nutritional Antioxidant Beta-Carotene," *J. Biol. Chem.*, 271(8):3988-94, Feb. 23, 1996.

Goto, G., et al., "A Facile Synthesis of 1,4-Benzoquinones Having a Hydroxyalkyl Side Chain," Chem Pharm Bull (Tokyo), 33(10):4422-31, 1985. cited by other.

Grisar, J. Martin et al., "Cardioselective ammonium, phosphonium, and sulfonium analogues of alpha-tocopherol and ascorbic acid that inhibit in vitro and ex vivo lipid peroxidation and scavenge superoxide radicals," 1: J Med Chem. 38(15):2880-6, Jul. 21, 1995.

James, A.M. et al.,"Antioxidant and prooxidant properties of mitochondrial coenzyme Q," Arch. Biochem. Biophys. 423, 47-56, 2004.

Jauslin, M. L., et al., "A cellular model for Friedreich Ataxia reveals small-molecule glutathione peroxidase mimetics as novel treatment strategy," Human Molecular Genetics, 11(24):3055-3063, 2002.

Jauslin, M., et al., "Mitochondria-Targeted Antioxidants Protect Friedreich Ataxia Fibroblasts From Endogenous Oxidative Stress More Effectively Than Untargeted Antioxidants," *FASEB J.*, 17(13):1972-4, Oct. 2003.

Kamo, N. et al., "Membrane potential measured with an electrods sensitive to tetraphenyl-phosphonium and relationship," J Membr. Biol, 49:105-121, 1979.

Keinan, E. et al., "Total synthesis of linear polyprenoids. II: Improved preparation of the aromatic nucleus of ubiquinone," J. Org. Chem. 52(17) 3872-3875, 1987.

Kelso, G., et al., "Prevention Of Mitochondrial Oxidative Damage Using Targeted Antioxidants," Ann. NY Acad. Sci., 959:263-74, Apr. 2002.

Koyama, Mayumi, et al., "Synthesis of Fluorine Analogs of Vitamin E. II. Synthesis of 2-(3-chloropropyl)-2,5,7,8-tetramethyl-6-chromano and its application for stereocontrolled Witting reaction and trifluromethyl ketones," Chemical and Pharmaceutical Bulletin, 36(8):2950-2954, 1988.

Masaki, N. et al., "Mitochondrial Damage as a Mechanism of Cell Injury in the Killing of Cultured Hepatocytes by tert-Butyl Hydroperoxide,"*Archives of Biochemistry and Biophysics*, 270(2): 672-680, May 1, 1989. (Abstract only).

Masaki, N., et al., "Intracellular Acidosis Protects Cultured Hepatocytes From The Toxic Consequences Of A Loss Of Mitochondrial Energization," Arch Biochem Biophys., 272(1):152-61, Jul. 1989. (Abstract only).

McKittrick et al., "Synthesis of the Yeast Antioxidant Benzofuran and Analogs," J. Chem. Soc. Perkin Trans, 1:709-712(721?), 1984.

Okamoto, K., et al., "Synthesis of quinones having carboxy- and hydroxy-alkyl side chains, and their effects on rat-liver lysosomal membrane," Chem Pharm Bull (Tokyo). Aug. 1982; 30(8):2797-819.

Rottenberg H., "The measurement of membrane potential and deltapH in cells, organelles, and vesicles," Methods Enzymol., 55:547-569, 1979.

Sakamoto, K. et al., "Role of the isoprenyl tail of ubiquinone in reaction with respiratory enzymes: studies with bovine heart mitochondrial complex I and *Escherichia coli* bo-type ubiquinol oxidase," Biochemistry 37(43), 15106-15113, Oct. 27, 1998.

Smith, Robin A.J., et al. "Targeting Coenzyme Q Derivatives to Mitochondria," Methods in Enzymology; Quinones and Quinone Enzymes, Part B, 382: 45-67, 2004.

Smith, Robin, A.J. et al., "Selective targeting of an antioxidant to mitochondria," *European Journal of Biochemistry*, 263:709-716, 1999.

Asin-Cayuela et al., "Fine-tuning the hydrophobicity of a mitochondria-targeted antioxidant," FEBS Letters 571:9-16, 2004.

Littaru et al., "Drugs Under Experimental and Clinical Research," 11(8):529-532, Abstract Only, from CAPLUS, Accession No. 1986:2306, p. 1 of 1, 1985.

Murphy, Michael P., "Selective targeting of bioactive compounds to mitochondria," Trends in Biotechnology 15 (8):326-330, 1997.

Oliveira et al., "Oxidatives stress in the pathogenesis of nonalcoholic fatty liver disease, in rats fed with a choline-deficient diet," J. Cell. Mol. Med. 6(3):399-406, 2002.

Videla et al., "Oxidative stress-related parameters in the liver of non-alcoholic fatty liver disease patients," Clinical Science 106:261-268, 2004.

* cited by examiner

A

B

MITOQUINONE DERIVATIVES USED AS MITOCHONDRIALLY TARGETED ANTIOXIDANTS

FIELD OF THE INVENTION

The invention relates to amphiphilic antioxidant compounds having a lipophilic cationic group, and the synthesis, formulation, and physicochemical properties of such compounds that favour their use as, for example, pharmaceuticals.

BACKGROUND

Oxidative stress contributes to a number of human degenerative diseases associated with ageing, such as Parkinson's disease, and Alzheimer's disease, as well as to Huntington's Chorea and Friedreich's Ataxia, and to non-specific damage that accumulates with aging. It also contributes to inflammation and ischaemic-reperfusion tissue injury in stroke and heart attack, and also during organ transplantation and surgery. To prevent the damage caused by oxidative stress a number of antioxidant therapies have been developed. However, most of these are not targeted within cells and are therefore less than optimally effective. Moreover, many such antioxidants have unfavourable physicochemical properties that limit for example, their bioavailability, and their ability to penetrate to the target organ to exert a therapeutic effect.

Mitochondria are intracellular organelles responsible for energy metabolism. Consequently, mitochondrial defects are damaging, particularly to neural and muscle tissues which have high energy demands. They are also the major source of the free radicals and reactive oxygen species that cause oxidative stress inside most cells. Therefore, the applicants believe delivering antioxidants selectively to mitochondria will be more effective than using non-targeted antioxidants. Accordingly, it is towards the provision of antioxidants which may be targeted to mitochondria that the present invention is directed.

Lipophilic cations may be accumulated in the mitochondrial matrix because of their positive charge (Rottenberg, 1979 *Methods Enzymol* 55, 547. Chen, 1988 *Ann Rev Cell Biol* 4, 155). Such ions are accumulated provided they are sufficiently lipophilic to screen the positive charge or delocalise it over a large surface area, also provided that there is no active efflux pathway and the cation is not metabolised or immediately toxic to a cell.

The focus of the invention is therefore on an approach by which it is possible to use the ability of mitochondria to concentrate specific lipophilic cations to take up linked antioxidants so as to target the antioxidant to the major source of free radicals and reactive oxygen species causing the oxidative stress.

Examples of antioxidant compounds that show good antioxidant activity in vivo yet exhibit poor antioxidant functionality with respect to the target compartment in vivo include Coenzyme Q (CoQ) and Idebenone. Both of these compounds have low bioavailability and must be administered at very high dose rates to be efficacious, and therefore have low therapeutic efficacy when referenced to the dose rate administered.

We believe without wishing to be bound by any theory that for an antioxidant compound, activity in vitro or ex vivo (such as, for example, antioxidant activity or mitochondrial accumulation) is by no means the sole determinant of antioxidant functionality and/or efficacy in vivo (such as, for example, therapeutic efficacy). Whilst it is true that to be useful as a mitochondrially targeted antioxidant compound of the present invention an antioxidant compound must exhibit a suitable antioxidant activity in vitro or ex vivo, to be efficacious in vivo the mitochondrially targeted antioxidant compound must exhibit other desirable physicochemical properties, such as, for example, suitable bioavailability, suitable localization or distribution within the target mitochondria, and/or suitable stability.

We believe without wishing to be bound by any theory that the mitochondrially targeted antioxidant compounds of the present invention exhibit advantageous antioxidant functionality, including bioavailability, and/or mitochondrial targeting and accumulation in vivo at least in part by virtue of their physicochemical properties, such as, for example, their amphiphilicity, their physical structure and/or dimensions, and/or low to moderate hydrophobicity and/or partition coefficient. Such compounds are thereby therapeutically efficacious at low dose rates in comparison to other antioxidant compounds.

In U.S. Pat. No. 6,331,532 by reference to exemplifications of compounds mitoquinol and mitoquinone (referred to collectively herein as mitoquinone/mitoquinol) there is disclosed the prospect of mitochondrial targeting of an antioxidant moiety reliant upon a lipophilic cation covalently coupled to the antioxidant moiety. The exemplified compound therein (despite generalisation of the bridge length), is the compound mitoquinone of the formula

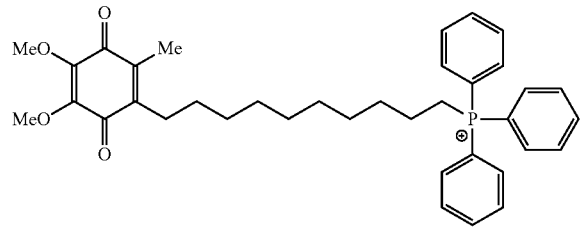

with a carbon bridge length of 10 (i.e. $C_{10}$ bridged). Its reduced form, mitoquinol, is also $C_{10}$ bridged.

Mitoquinone/mitoquinol, despite excellence in antioxidant activity and targeting and accumulation in mitochondria in vitro and in vivo, we have found to be somewhat unstable as the bromide salt. We have also found that the physiochemical properties of mitoquione/mitoquinol as disclosed in U.S. Pat. No. 6,331,532 less appropriate for pharmaceutical formulation, for example, where administration is to be oral or parenteral and/or where there is targeting of the compound to mitochondria in tissues of internal organs (for example, brain, heart, liver, or other organs).

Examples of compounds of the present invention are suitable for pharmaceutical formulation. They may be in a form other than a crystalline and/or solid form, but are amenable to formation of a solid form by admixture with other agents such as for example, carriers, excipients, complexation agents, or other additives and the like, such as, for example, cyclodextrins. Advantageously such agents are pharmaceutically acceptable.

We have determined a desirability to offer examples of the amphiphilic mitochondrially targeted antioxidant compounds of the present invention with their positive charge in association with a suitable anion thereby to provide the compound as a general neutralised salt form, including solid or crystalline products. In such salt forms however certain salt forming anions we have found to be best avoided as they exhibit reactivity against the antioxidant compound, for example, against the antioxidant moiety, the linking moiety, or the lipophilic cationic moiety, and/or may lead to cleavage at or of the antioxidant moiety. Other salt forming anions are considered pharmaceutically undesirable. For example, nitrate moieties are considered inappropriate generally by pharmaceutical companies as being pharmaceutically or environmentally unacceptable, whilst a hydrogen bromide frequently used in salt forming of such compounds we find to have nucleophilic properties that can lead to a reactivity against the antioxidant moiety, for example, a cleavage of a methyl group from the antioxidant moiety of the compound of general formula (II) herein, and/or some overall decrease in stability of the overall compound. For example, we have determined that the bromide salt of mitoquinone is somewhat unstable.

We believe therefore that salt forms, including salt forms as a liquid, solid or crystalline form, of mitochondrially targeted antioxidants are best associated with an anion or like moiety that is not nucleophilic, and/or one which does not exhibit reactivity against any of the moieties comprising the antioxidant compound or complex. It is also preferable that the anion is pharmaceutically acceptable.

OBJECT OF THE INVENTION

Accordingly, it is an object of the present invention to provide pharmaceutically acceptable amphiphilic antioxidant compounds and compositions, dosage forms and methods reliant on said compounds which are, for example, useful in the treatment of diseases or conditions associated with oxidative stress, or to provide the public with a useful choice.

SUMMARY OF THE INVENTION

In a first aspect, the present invention consists in a compound comprising a lipophilic cationic moiety linked by a linking moiety to an antioxidant moiety, and an anionic complement for said cationic moiety, wherein the cationic species is capable of mitochondrially targeting the antioxidant species, and the salt form is chemically stable and/or the anionic complement does not exhibit reactivity against the antioxidant moiety, the cationic moiety or the linking moiety.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fullerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

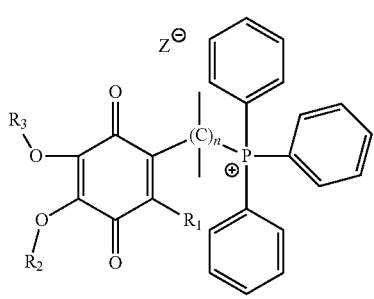

and/or its quinol form, wherein $R_1$, $R_2$, and $R_3$, which can be the same or different, are selected from $C_1$ to $C_5$ alkyl (optionally substituted) moieties or H, and wherein n is an integer from about 2 to about 20, and wherein Z is a non-reactive anion.

Preferably Z is selected from the group consisting of alkyl or aryl sulfonates or nitrates.

Preferably each C of the (C)n bridge is saturated.

In a preferred embodiment, the compound has the formula

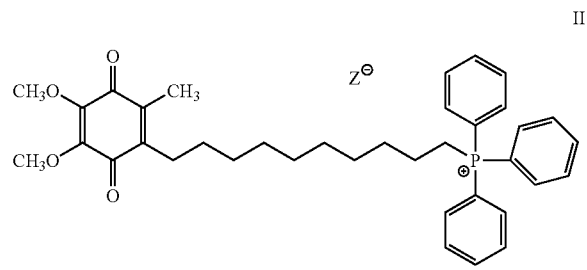

and/or its quinol form, wherein Z is a non-nucleophilic anion.

More preferably, the compound has the formula

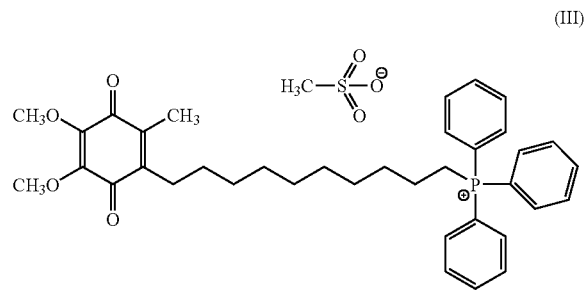

In another aspect the invention provides a pharmaceutical composition comprising or including a compound comprising a lipophilic cationic moiety linked by a linking moiety to an antioxidant moiety, and an anionic complement for said cationic moiety, wherein the cationic species is capable of mitochondrially targeting the antioxidant species, and the salt form is chemically stable and/or the anionic complement does not exhibit reactivity against the antioxidant moiety, the cationic moiety or the linking moiety.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fullerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

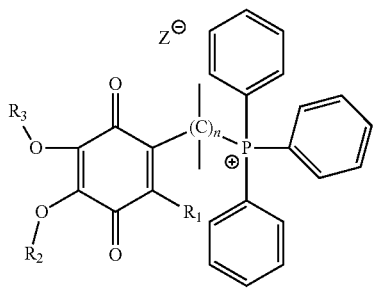

and/or its quinol form, wherein $R_1$, $R_2$, and $R_3$, which can be the same or different, are selected from $C_1$ to $C_5$ alkyl (optionally substituted) moieties or H, and wherein n is an integer from about 2 to 20, and wherein Z is a non-reactive anion.

Preferably Z is selected from the group consisting of alkyl or aryl sulfonates or nitrates.

Preferably each C of the (C)n bridge is saturated.

In a further embodiment, the compound has the formula

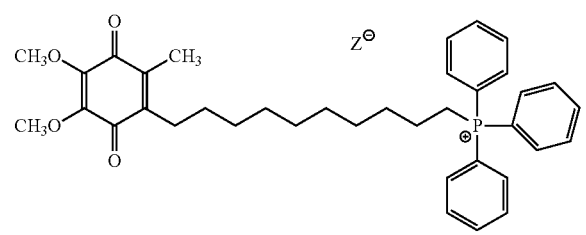

and/or its quinol form, wherein Z is a non-nucleophilic anion.

In a further embodiment the composition comprises a compound having the formula II and/or its quinol form, wherein Z is a non-nucleophilic anion, and wherein the composition comprises cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the composition comprises a compound having the formula

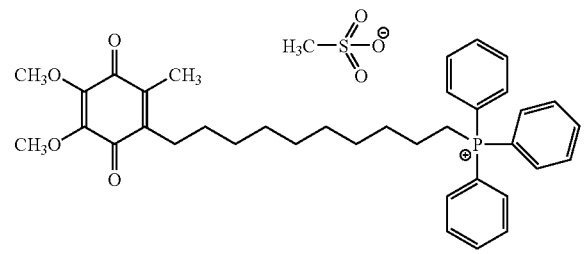

wherein the cyclodextrin is β-cyclodrextrin, more preferably the molar ratio of compound to cyclodextrin is about 1:2.

In one embodiment the pharmaceutical composition is formulated for oral administration.

In a further embodiment the pharmaceutical composition is formulated for parenteral administration.

In a further aspect the present invention provides a dosage unit comprising or including a compound comprising a lipophilic cationic moiety linked by a linking moiety to an antioxidant moiety, and an anionic complement for said cationic moiety, wherein the cationic species is capable of mitochondrially targeting the antioxidant species, and the salt form is chemically stable and/or the anionic complement does not exhibit reactivity against the antioxidant moiety, the cationic moiety or the linking moiety, together with any pharmaceutically acceptable diluent and/or carrier and/or excipient.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fillerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

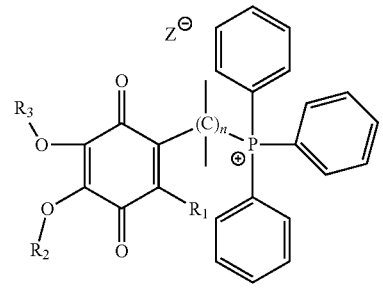

and/or its quinol form, wherein $R_1$, $R_2$, and $R_3$, which can be the same or different, are selected from $C_1$ to $C_5$ alkyl (optionally substituted) moieties or H, and wherein n is an integer from about 2 to 20, and wherein Z is a non-reactive anion.

Preferably Z is selected from the group consisting of alkyl or aryl sulfonates or nitrates.

Preferably each C of the (C)n bridge is saturated.

In a further embodiment, the compound has the formula and/or its quinol form, wherein Z is a non-nucleophilic anion.

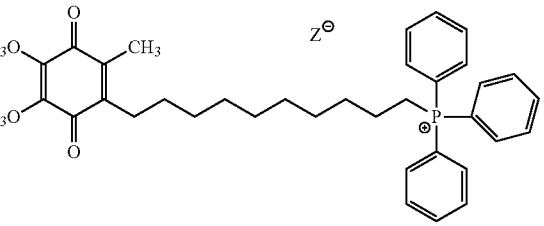

In a further embodiment the dosage unit comprises a compound having the formula II and/or its quinol form, wherein Z is a non-nucleophilic anion, and wherein the composition comprises cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the dosage unit comprises a compound having the formula

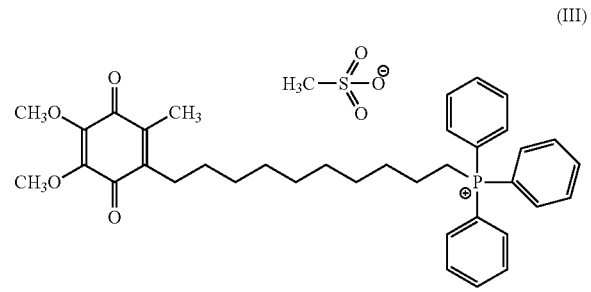

(III)

wherein the cyclodextrin is β-cyclodrextrin, more preferably the molar ratio of compound to cyclodextrin is about 1:2.

In one embodiment the dosage unit is suitable for oral administration.

In a further embodiment the dosage unit is suitable for parenteral administration.

In a further aspect the present invention provides a compound or a pharmaceutically acceptable salt thereof, a composition, or a dosage form of the present invention for use in the prophylaxis or treatment of oxidative stress in a mammal by administration of the compound or the salt thereof to said mammal.

In one embodiment, the compound is a compound of formula II or a pharmaceutically acceptable salt thereof.

In another embodiment, said administration is on the first day at a dose of about 1.02 about 2.0 times the daily maintenance dose, followed by administration of the compound or the salt thereof at the daily maintenance dose of the subsequent days.

Preferably the salt is that of the methanesulfonate, and the compound is combined with cyclodextrin.

More preferably the compound has the formula

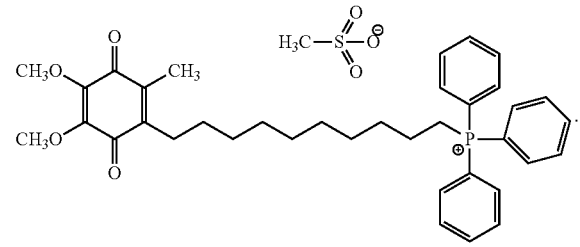

(III)

Preferably, the cyclodextrin is β-cyclodrextrin, more preferably the molar ratio of compound to cyclodextrin is about 1:2.

In a further aspect the present invention provides a compound or a pharmaceutically acceptable salt thereof, a composition, or a dosage form of the present invention for use in the prophylaxis or treatment of symptoms of aging in a mammal by administration of the compound or the salt thereof to said mammal.

In one embodiment, the compound is a compound of formula II or a pharmaceutically acceptable salt thereof.

In another embodiment, said administration is on the first day at a dose of about 1.02 about 2.0 times the daily maintenance dose, followed by administration of the compound or the salt thereof at the daily maintenance dose of the subsequent days.

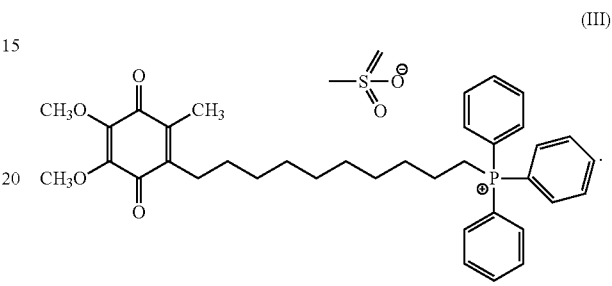

(III)

Preferably the salt is that of the methanesulfonate, and the compound is combined with cyclodextrin.

More preferably the compound has the formula

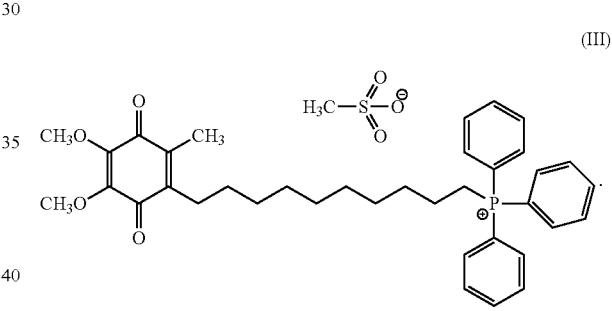

(III)

Preferably, the cyclodextrin is β-cyclodrextrin, more preferably the molar ratio of compound to cyclodextrin is about 1:2.

In a further aspect, the present invention consists in a stable compound comprising a lipophilic cationic moiety linked by a linking moiety to an antioxidant moiety, and an anionic complement for said cationic moiety, wherein the cationic species is capable of mitochondrially targeting the antioxidant species, and the anionic complement is not a halogen ion, and the anionic complement is non-nucleophilic, and/or the anionic complement does not exhibit reactivity against the cationic moiety, the linking moiety, or the antioxidant moiety.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fillerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

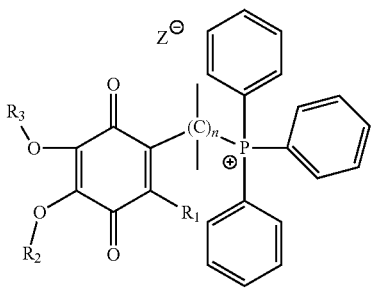

and/or its quinol form, wherein $R_1$, $R_2$, and $R_3$, which can be the same or different, are selected from $C_1$ to $C_5$ alkyl (optionally substituted) moieties or H, and wherein n is an integer from about 2 to about 20, and wherein Z is a non-reactive anion.

Preferably Z is selected from the group consisting of alkyl or aryl sulfonates or nitrates.

Preferably each C of the (C)n bridge is saturated.

In a preferred embodiment, the compound has the formula

II

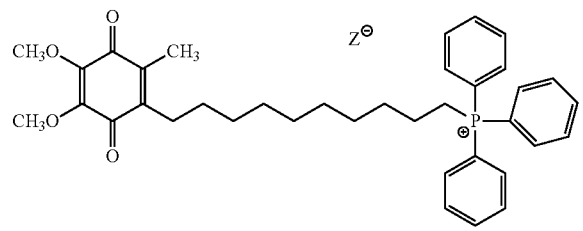

and/or its quinol form, wherein Z is a non-nucleophilic anion.

More preferably, the compound has the formula (III)

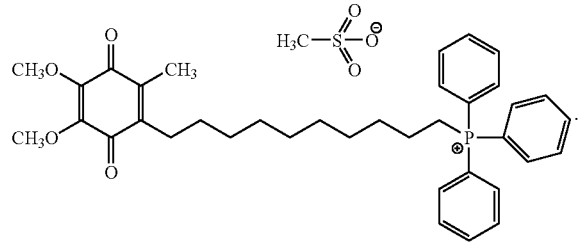

In another aspect the invention provides a pharmaceutical composition comprising or including a stable compound comprising a cationic species being a lipophilic cationic moiety linked by a linking moiety to an antioxidant moiety, and an anionic complement for said cationic moiety, wherein the cationic species is capable of mitochondrially targeting the antioxidant species, and the anionic complement is not a halogen ion, and the anionic complement is non-nucleophilic, and/or the anionic complement does not exhibit reactivity against the cationic moiety, the linking moiety, or the antioxidant moiety.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fullerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

I

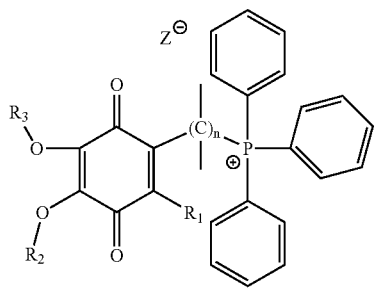

and/or its quinol form, wherein $R_1$, $R_2$, and $R_3$, which can be the same or different, are selected from $C_1$ to $C_5$ alkyl (optionally substituted) moieties or H, and wherein n is an integer from about 2 to 20, and wherein Z is a non-reactive anion.

Preferably Z is selected from the group consisting of alkyl or aryl sulfonates or nitrates.

Preferably each C of the (C)n bridge is saturated.

In a further embodiment, the compound has the formula

II

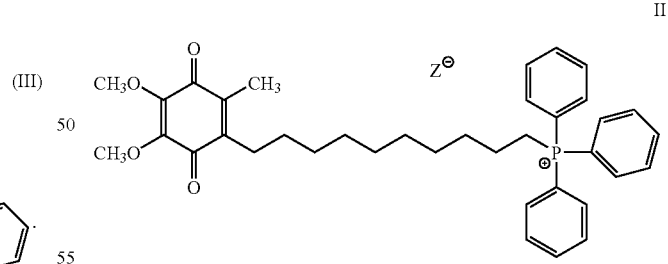

and/or its quinol form, wherein Z is a non-nucleophilic anion.

In a further embodiment the composition comprises a compound having the formula II and/or its quinol form, wherein Z is a non-nucleophilic anion, and wherein the composition comprises cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the composition comprises a compound having the formula

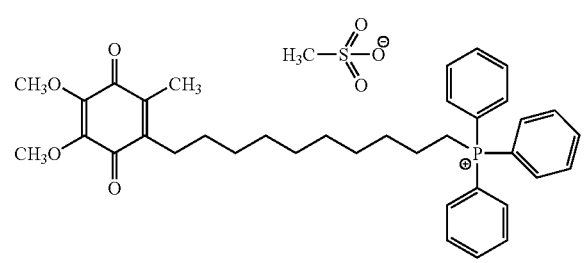

(III)

wherein the cyclodextrin is β-cyclodrextrin, more preferably the molar ratio of compound to cyclodextrin is about 1:2.

In one embodiment the pharmaceutical composition is formulated for oral administration.

In a further embodiment the pharmaceutical composition is formulated for parenteral administration.

In a further aspect the present invention consists of a dosage unit comprising or including a stable compound comprising a lipophilic cationic moiety linked by a linking moiety to an antioxidant moiety, and an anionic complement for said cationic moiety, together with any pharmaceutically acceptable diluent and/or carrier and/or excipient wherein the cationic species is capable of mitochondrially targeting the antioxidant species, and the anionic complement is not a halogen ion, and the anionic complement is non-nucleophilic, and/or the anionic complement does not exhibit reactivity against the cationic moiety, the linking moiety, or the antioxidant moiety.

In one embodiment the antioxidant moiety is a quinone or a quinol.

In other embodiments the antioxidant moiety is selected from the group comprising vitamin E and vitamin E derivatives, chain breaking antioxidants, including butylated hydroxyanisole, butylated hydroxytoluene, general radical scavengers including derivatised fillerenes, spin traps including derivatives of 5,5-dimethylpyrroline-N-oxide, tert-butylnitrosobenzene, tert-nitrosobenzene, α-phenyl-tert-butylnitrone and related compounds.

In one embodiment, the lipophilic cationic moiety is a substituted or an unsubstituted triphenylphosphonium cation.

In one embodiment the compound has the general formula I

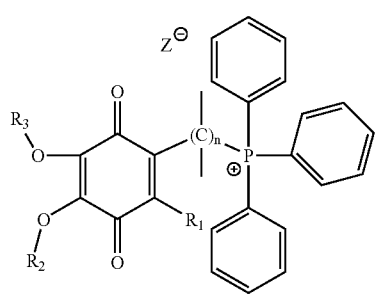

I and/or its quinol form, wherein $R_1$, $R_2$, and $R_3$, which can be the same or different, are selected from $C_1$ to $C_5$ alkyl (optionally substituted) moieties or H, and wherein n is an integer from about 2 to 20, and wherein Z is a non-reactive anion.

Preferably Z is selected from the group consisting of alkyl or aryl sulfonates or nitrates.

Preferably each C of the (C)n bridge is saturated.

In a further embodiment, the compound has the formula

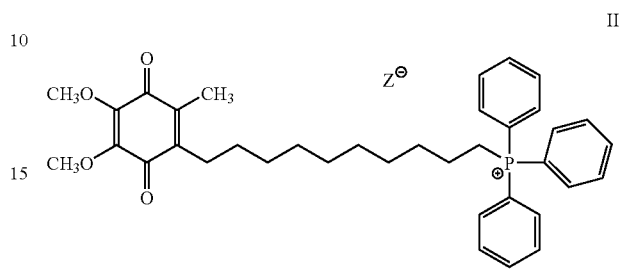

II and/or its quinol form, wherein Z is a non-nucleophilic anion.

In a further embodiment the dosage unit comprises a compound having the formula II and/or its quinol form, wherein Z is a non-nucleophilic anion, and wherein the composition comprises cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the dosage unit comprises a compound having the formula

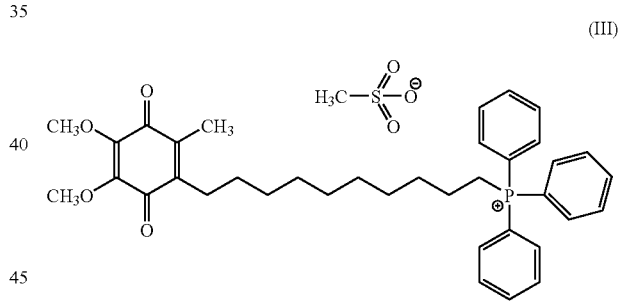

(III)

wherein the cyclodextrin is β-cyclodrextrin, more preferably the molar ratio of compound to cyclodextrin is about 1:2.

In one embodiment the dosage unit is suitable for oral administration.

In a further embodiment the dosage unit is suitable for parenteral administration.

In a further aspect, the present invention consists in a dosage unit suitable for oral administration comprising as an active ingredient a compound in accordance with the present invention, the compound being of or being formulated as a crystalline form and/or non-liquid form.

In a further aspect, the present invention consists in a dosage unit suitable for parenteral administration comprising as an active ingredient a compound in accordance with the present invention.

In a further aspect, the present invention provides a pharmaceutical composition suitable for treatment of a patient who would benefit from reduced oxidative stress or reduced symptoms of ageing which comprises or includes an effective amount of a compound of the present invention in combination with one or more pharmaceutically acceptable carriers, excipients, or diluents.

In one embodiment the compound is a compound of formula I.

In one example, the compound is complexed with cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the compound is a compound of formula (III) and the cyclodextrin is β-cyclodrextrin, more preferably and the molar ratio of compound to cyclodextrin is about 1:2.

In a further aspect, the invention provides a method of reducing oxidative stress in a cell which comprises the step of contacting said cell with a compound of the present invention.

In one embodiment the compound is a compound of formula I.

In one example, the compound is complexed with cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the compound is a compound of formula (III) and the cyclodextrin is β-cyclodrextrin, more preferably and the molar ratio of compound to cyclodextrin is about 1:2.

In one embodiment the pharmaceutical composition is formulated for oral administration.

In a further embodiment the pharmaceutical composition is formulated for parenteral administration.

In a further aspect, the present invention provides a pharmaceutical composition suitable for treatment of a patient suffering from or predisposed to Parkinson's disease, Alzheimer's disease, Huntington's Chorea, or Friedreich's Ataxia, which comprises or includes an effective amount of a compound of the present invention in combination with one or more pharmaceutically acceptable carriers, excipients, or diluents.

Preferably said treatment is of a patient suffering from or predisposed to Friedreich's Ataxia.

In still a further aspect, the invention provides a method of therapy or prophylaxis of a patient who would benefit from reduced oxidative stress which comprises or includes the step of administering to said patient a compound of the present invention.

In one embodiment the compound is a compound of formula I.

In one example, the compound is complexed with cyclodextrin.

In various examples the molar ratio of compound to cyclodextrin is from about 10:1 to about 1:10, from about 5:1 to about 1:5, from about 4:1 to about 1:4, from about 2:1 to about 1:2, or about 1:1, for example the molar ratio of compound to cyclodextrin is about 1:2.

More preferably, the compound is a compound of formula (III) and the cyclodextrin is β-cyclodrextrin, more preferably and the molar ratio of compound to cyclodextrin is about 1:2.

In one embodiment said administration is oral administration.

In another embodiment said administration is parenteral administration.

In another aspect the invention provides a method of therapy or prophylaxis of a patient who would benefit from reduced oxidative stress, or reduced symptoms of ageing, which comprises the step of administering to the patient a compound of the present invention.

In yet another aspect, the invention provides a method of therapy or prophylaxis of a patient suffering from or predisposed to Parkinson's disease, Alzheimer's disease, Huntington's Chorea, or Friedreich's Ataxia which comprises or includes the step of administering to said patent a compound of the present invention.

Preferably the method of therapy or prophylaxis is of a patient suffering from or predisposed to Friedreich's Ataxia.

In another aspect the invention provides a method of reducing oxidative stress in a cell, which comprises the step of administering to the cell a compound of the present invention.

In another aspect the invention provides the use of a compound as previously described in the preparation or manufacture of a medicament, dosage unit, or pharmaceutical composition effective for use in for the reduction of oxidative stress in a patient.

In another aspect the invention provides the use of a compound as previously described in the preparation or manufacture of a medicament, dosage unit, or pharmaceutical composition effective for use for the reduction of symptoms of aging in a patient.

In a further aspect the invention provides the use of a compound of the present invention in the preparation or manufacture of a medicament, dosage unit, or pharmaceutical composition effective for use in the treatment or prophylaxis of a patient suffering from or predisposed to Parkinson's disease, Alzheimer's disease, Huntington's Chorea, or Friedreich's Ataxia which comprises or includes the step of administering to said patent a compound of the present invention.

Preferably the medicament, dosage unit, or pharmaceutical composition is effective for use in the treatment or prophylaxis of a patient suffering from or predisposed to Friedreich's Ataxia.

In another aspect the invention provides the use of a compound as previously described in the preparation or manufacture of a medicament, dosage unit, or pharmaceutical composition effective for use in the reduction of oxidative stress in a cell.

Preferably, said preparation or manufacture is with other material or materials, more preferably pharmaceutically acceptable diluents, excipients, and/or carriers.

In a further aspect the present invention consists in a method of synthesis of a compound with a moiety or the moiety of the formula I

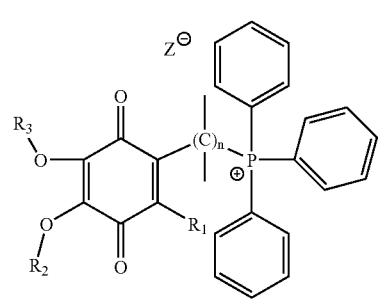

(and/or its quinone form) wherein $R_1$, $R_2$, and $R_3$, which can be the same or different, are selected from $C_1$ to $C_5$ alkyl (optionally substituted) moieties, and wherein n is an integer from 2 to 20, said method including or comprising the admixture of cyclodextrin.

Preferably each C of the (C)n bridge is saturated.

In a further aspect the present invention consists in a method of synthesis of a compound having the formula

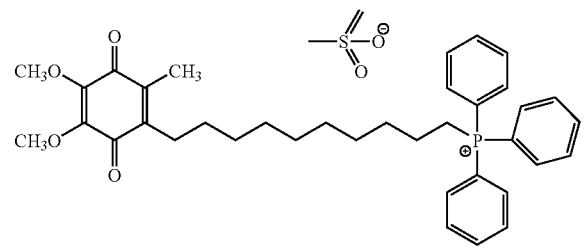

said method including or comprising the admixture of cyclodextrin.

In a further aspect the present invention consists in a method of synthesis of a compound having the formula (III)

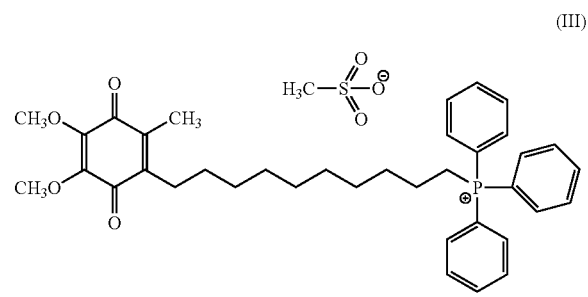

essentially as herein described.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification the term "quinone", whether used alone or prefixed with another term to describe the oxidized form of a compound, will be understood to include within its scope the reduced form of that compound, that is, the quinol form. Similarly, reference to a quinone, by structural depiction for example, also includes within its scope the quinol form.

Throughout this specification the term "quinol", whether used alone or prefixed with another term to describe the reduced form of a compound, will be understood to include within its scope the oxidised form of that compound, that is, the quinone form. Similarly, reference to a quinol, by structural depiction for example, also includes within its scope the quinone form.

As used herein the term "and/or" includes both "and" and "or" as options.

As used herein, the term "partition coefficient" and "partition coefficient (octanol:water)" refer to the octan-1-ol/phosphate buffered saline partition coefficient determined at 25° C. or 37° C. (see Kelso, G. F., Porteous, C. M., Coulter, C. V., Hughes, G. Porteous, W. K., Ledgerwood, E. C., Smith, R. A. J. and Murphy, M. P. 2001 J Biol Chem 276 4588. Smith, R. A. J., Porteous, C. M., Coulter, C. V. and Murphy, M. P. 1999 Eu. J Biochem 263, 709. Smith, R. A. J., Porteous, C. M., Gane, A. M. and Murphy, M. P. 2003 Proc Nat Acad Sci 100, 5407.), or the octanol/water partition coefficient calculated using Advanced Chemistry Development (ACD) Software Solaris V4.67 as described in Jauslin, M. L., Wirth, T., Meier, T., and Schoumacher, F., 2002, Hum Mol Genet. 11, 3055.

As used herein, the phrase "acceptable for pharmaceutical preparation" includes within its meaning not only an acceptability with regard to pharmaceutical administration, but also in respect of formulation for, for example, acceptable stability, shelf life, hygroscopicity, preparation and the like.

As used herein a "non-reactive anion" is an anion which exhibits no reactivity against the antioxidant moiety, the lipophilic cation, or the linking moiety. For example, if one such moiety of the compound comprises a target of nucleophilic attack, the anion is non-nucleophilic.

Although broadly as defined above, the invention is not limited thereto but also consists of embodiments of which the following description provides examples.

In particular, a better understanding of the invention will be gained with reference to the accompanying drawings.

DETAILED DESCRIPTION OF THE INVENTION

Figure 1:
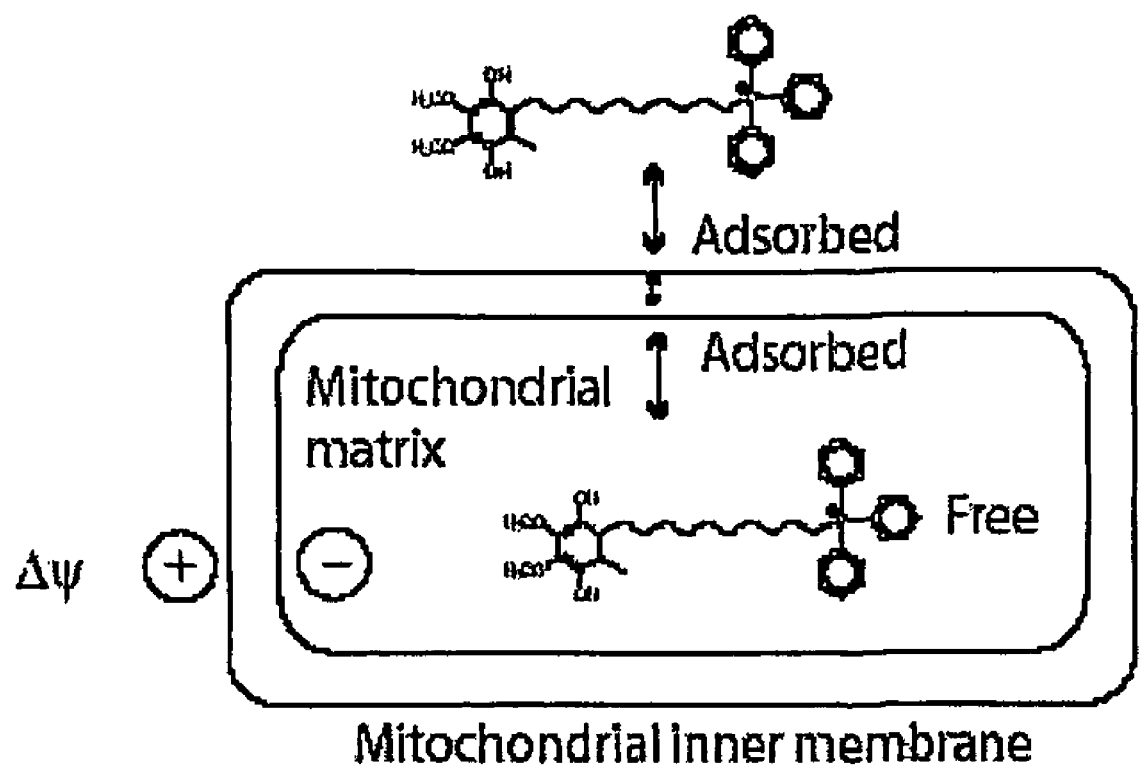
FIG. 1 depicts the uptake of amphiphilic antioxidant compounds by mitochondria, wherein the uptake of Mitoquinone-C10 into an energised mitochondrion is shown schematically.

As stated above, the focus of this invention is on the mitochondrial targeting of compounds, primarily for the purpose of therapy and/or prophylaxis to reduce oxidative stress.

Mitochondria have a substantial membrane potential of up to 180 mV across their inner membrane (negative inside). Because of this potential, membrane permeant, lipophilic cations accumulate several-hundred fold within the mitochondrial matrix.

The applicants have found that by coupling lipophilic cations (for example the lipophilic triphenylphosphonium cation) to an antioxidant moiety the resulting amphiphilic compound can be delivered to the mitochondrial matrix within intact cells. The antioxidant is then targeted to a primary production site of free radicals and reactive oxygen species within the cell, rather than being randomly dispersed.

The applicants have now further determined that the properties of the antioxidant compound, such as for example the nature of the antioxidant moiety, the physical and chemical characteristics of the linking moiety, such as, for example, the length or lipophilicity of the linking moiety, and/or the nature of the lipophilic cation contribute to the efficacy of the antioxidant compound in vivo and contribute to the antioxidant functionality of the compound. For antioxidant compounds of the present invention, efficacy in vivo may in part comprise suitable bioavailability, suitable stability, suitable pharmacokinetics suitable antioxidant activity, and/or suitable mitochondrial targeting and/or accumulation.

In principle, any lipophilic cation and any antioxidant capable of being transported to and/or through the mitochondrial membrane and accumulated at or within the mitochondria of intact cells, can be employed in forming the compounds of the invention.

It is however preferred that the lipophilic cation be the triphenylphosphonium cation herein exemplified. Other lipophilic cations which may covalently be coupled to antioxidants in accordance with the present invention include the tribenzyl ammonium and phosphonium cations. In some examples of antioxidant compounds of the present invention, the lipophilic cation is coupled to the antioxidant moiety by a saturated linear carbon chain having from 1 to about 30 carbon atoms, for example from 2 to about 20, from about 2 to about 15, from about 3 to about 10, or from about 5 to about 10 carbon atoms. In a particularly preferred example, the linear carbon chain comprises 10 carbon atoms.

Preferably the carbon chain is an alkylene group (for example, $C_1$-$C_{20}$, or $C_1$-$C_{15}$), yet carbon chains which optionally include one or more double or triple bonds are also within the scope of the invention. Also included are carbon chains which include one or more substituents (such as hydroxyl, carboxylic acid or amide groups), and/or include one or more side chains or branches, such as those selected from unsubstituted or substituted alkyl, alkenyl, or alkynyl groups. Also included are carbon chains which comprise more than about 30 carbon atoms but whose length is equivalent to a linear saturated carbon chain having from 1 to about 30 carbon atoms.

It will be appreciated by those skilled in the art that moieties other than a straight alkylene may be used to covalently couple the antioxidant moiety to the lipophilic cation, for example, substituted or branched alkyl groups, peptide bonds, and the like.

In some embodiments, the lipophilic cation is linked to the antioxidant moiety by a straight chain alkylene group having 1 to 10 carbon atoms; such as, for example an ethylene, propylene, butylene, pentylene or decylene group.

Antioxidant moieties useful in the present invention include those which require interaction with reductants for antioxidant activity whether for initial antioxidant activity or for the recycling of antioxidant activity, or both. For example, antioxidant compounds of the present invention which comprise as the active antioxidant moiety a quinol moiety may be administered in the quinone form. To function as an antioxidant, that is to have antioxidant activity, the quinone must be reduced to the quinol form by interaction with a reductant, such as, for example, a mitochondrial reductant such as Complex II, for initial antioxidant activity. Subsequent interaction of the oxidised quinone form with reductants can lead to recycling of antioxidant activity.

Other examples of antioxidant moieties useful in the present invention include those which exist already as the reduced form and do not require interaction with reductants for initial antioxidant activity. Notwithstanding this, subsequent interaction of the oxidised form of such antioxidant moieties with mitochondrial reductants can lead to the recycling of antioxidant activity. For example, the antioxidant moiety Vitamin E can be administered in the reduced form and so does not require interaction with reductants for initial antioxidant activity, but may subsequently interact with reductants, such as, for example, the endogenous quinone pool, thereby to recycle antioxidant activity.

Further examples of antioxidant moieties useful in the present invention include those that are not recycled by interaction with mitochondrial reductants.

Examples of antioxidant moieties useful in the present invention include vitamin E and vitamin E derivatives, chain breaking antioxidants, such as butylated hydroxyanisole, butylated hydroxytoluene, quinols and general radical scavengers such as derivatised fullerenes. In addition, spin traps, which react with free radicals to generate stable free radicals can also be used. These will include derivatives of 5,5-dimethylpyrroline-N-oxide, tert-butylnitrosobenzene, tert-nitrosobenzene, α-phenyl-tert-butylnitrone and related compounds.

Preferred antioxidant compounds, including those of general formulae I and II herein, can be readily prepared, for example, by the following reaction:

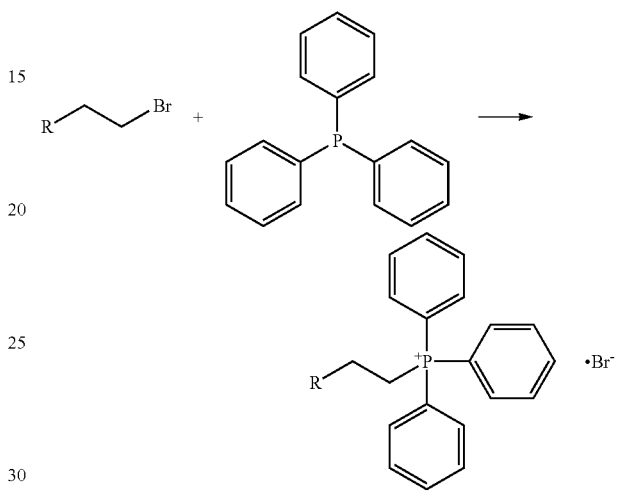

The general synthesis strategy is to heat a precursor containing a suitable leaving group, preferably a alkyl sulfonyl, bromo or iodo precursor with greater than 1 equivalents of triphenylphosphine under argon for several days. The phosphonium compound is then isolated as its salt. To do this the product is triturated repeatedly with diethyl ether until an off-white solid remains. This is then dissolved in chloroform or dichloromethane and precipitated with diethyl ether to remove the excess triphenylphosphine. This is repeated until the solid no longer dissolves in chloroform. At this point the product is recrystallised several times from a suitable solvent such as chloroform, acetone, ethyl acetate or higher alcohols.

A preferred synthetic method which may be used to prepare a stable form of a preferred mitochondrially targeted antioxidant compound of formula III (also referred to herein as Mitoquinone-C10 mesylate or Mitoquinone-C10 methanesultonate) is as set out in Example 1 herein.

It will also be appreciated that the anion of the antioxidant compound thus prepared can readily be exchanged with another pharmaceutically or pharmacologically acceptable anion, if this is desirable or necessary, using ion exchange or other techniques known in the art.

The applicants have determined that the stability of the salt form of the antioxidant compound is enhanced when the anion does not exhibit reactivity towards the antioxidant moiety, the linking moiety, or the lipophilic cationic moiety. For example, in the case of preferred examples of antioxidant compounds of the invention, the anion is not nucleophilic. It is also desirable that the anion is a pharmaceutically acceptable anion. It is also preferred that for pharmaceutical formulation the anion does not exhibit reactivity towards any other agents comprising the formulation.

Examples of non-nucleophilic anions include hexafluoroantimonate, -arsenate or -phosphate, or tetraphenylborate, tetra(perfluorophenyl)borate or other tetrafluoroborates, trifluoromethane sulfonate, aryl and alkyl sulfonates such as methanesulfonate and p-toluenesulfonate, and phosphates.

Examples of pharmaceutically acceptable anions include halogen ions such as a fluoride ion, chloride ion, bromide ion and iodide ion; anions of inorganic acid salts such as nitrate, perchlorate, sulfate, phosphate, and carbonate; pharmaceutically acceptable anions of lower alkylsulfonic acid salts such as methanesulfonic acid, and ethanesulfonic acid salts; pharmaceutically acceptable anions of arylsulfonic acid salts such as benzenesulfonic acid, 2-naphthalenesulfonic acid and p-toluenesulfonic acid salts; pharmaceutically acceptable anions of organic acid salts such as trichloroacetic acid, trifluoroacetic acid, hydroxyacetic acid, benzoic acid, mandelic acid, butyric acid, propionic acid, formic acid, fumaric acid, succinic acid, citric acid, tartaric acid, oxalic acid, maleic acid, acetic acid, malic acid, lactic acid, and ascorbic acid salts; and pharmaceutically acceptable anions of acidic amino acid salts such as glutamic acid and asparatic acid salts.

In the case of preferred examples antioxidant compounds of the invention, the halogen anion precursor is exchanged for aryl or alkyl sulphonate anions. Examples include, but are not limited to, benzene sulfonate, p-toluene sulfonate, 2-napthylene sulphonate, methanesulfonate, ethanesulfonate, propanesulfonate. A particularly preferred anion is the methanesulfonate anion. As described above, an example of an antioxidant compound of the invention wherein the anion is methanesulfonate is the particularly preferred antioxidant compound of formula III, herein referred to as Mitoquinone-C10 methanesulfonate or Mitoquinone-C10 mesylate.

The same general procedure can be used to make a wide range of mitochondrially targeted compounds with different antioxidant moieties R attached to the triphenylphosphonium (or other lipophilic cationic) moiety or moieties. These will include a series of vitamin E derivatives, in which the length of the bridge coupling the Vitamin-E function with the triphenylphosphonium (or other lipohilic cationic) moiety is varied. Other antioxidants which can be used as R include chain breaking antioxidants, such as butylated hydroxyanisole, butylated hydroxytoluene, quinols and general radical scavengers such as derivatised fullerenes. In addition, spin traps, which react with free radicals to generate stable free radicals can also be synthesized. These will include derivatives of 5,5-dimethylpyrroline-N-oxide, tert-butylnitrosobenzene, tert-nitrosobenzene, α-phenyl-tert-butylnitrone and related compounds.

It will be appreciated that for an antioxidant compound of the present invention, as for any drug, activity in vitro is by no means the sole determinant of functionality or efficacy in vivo. The antioxidant activity of the antioxidant compounds of the present invention can be determined by methods such as those described herein using, for example, isolated mitochondria and/or isolated cells. Whilst it is true that, to be useful as a mitochondrially targeted antioxidant compound of the present invention an antioxidant compound must exhibit a suitably high antioxidant activity in such assays, to be efficacious in vivo the mitochondrially targeted antioxidant compound must exhibit other desirable physicochemical properties, for example, suitable bioavailability, stability, or antioxidant functionality.

Examples of antioxidant compounds that show good antioxidant activity yet exhibit poor bioavailability with respect to the target compartment in vivo include Coenzyme Q (CoQ) and Idebenone. Both of these compounds must be administered at very high dose rates (for example, 0.5-1.2 g) to obtain minimal clinical effects in human patients.

Examples of the mitochondrially targeted antioxidant compounds of the present invention exhibit good antioxidant activity and bioavailability and thereby are efficacious in vivo at low dose rates. A determination of the bioavailability of a preferred amphiphilic mitochondrially targeted antioxidant compound of the present invention, Mitoquinone-C10 mesylate and a cyclodextrin complex thereof is presented herein in Example 11. We believe the antioxidant compounds of the present invention to be effective at mitochondrial targeting of antioxidant activity, whilst exhibiting one or more of the additional benefits of being available as a crystalline or solid form or being able to be formulated as a solid form, increased stability, enhanced bioavailability, and/or enhanced antioxidant functionality. The physical and chemical characteristics of the antioxidant compounds of the present invention we believe, again without wishing to be bound by any theory, confer upon the antioxidant compounds of the present invention preferred characteristics, thereby enabling their use in compositions, formulations and methods amongst other applications to which the antioxidant compounds of the prior art may be less suitable given their chemical and physical properties.

In some embodiments of the invention, the antioxidant compound is a quinol derivative of the formula II defined above. For example, a quinol derivative of the invention is the compound Mitoquinone-C10 (of which the compound of formula III is a specific salt form) as defined above. A further example of a compound of the invention is a compound of formula I in which $(C)_n$ is $(CH_2)_5$, and the quinol moiety is the same as that of Mitoquinone-C10, herein referred to as Mitoquinone-C5 (see FIG. 3C). Yet a further example of a compound of the invention is a compound of formula I in which $(C)_n$ is $(CH_2)_3$, and the quinol moiety is the same as that of Mitoquinone-C10, which is referred to herein as Mitoquinone-C3 (see FIG. 3B). Still a further example of a compound of the invention is a compound of formula I in which $(C)_n$ is $(CH_{12})_{15}$, and the quinol moiety is the same as that of Mitoquinone-C10, herein referred to as Mitoquinone-C15 (see FIG. 3E).

Once prepared, the antioxidant compound of the invention in any pharmaceutically appropriate form and optionally including pharmaceutically-acceptable carriers, excipients, diluents, complexation agents, or additives, will be administered to the patient requiring therapy and/or prophylaxis. Once administered, the compound will target antioxidant activity to the mitochondria within the cells of the patient.

Antioxidant compounds of the present invention may be administered to patients by oral and/or parenteral administration routes.

The antioxidant compound must be formulated into a stable, safe pharmaceutical composition for administration to a patient. The composition can be prepared according to conventional methods by dissolving or suspending an amount of the antioxidant compound ingredient in a diluent. The amount is from between 0.1 mg to 1000 mg per ml of diluent of the antioxidant compound. An acetate, phosphate, citrate or glutamate buffer may be added allowing a pH of the final composition to be from 5.0 to 9.5; optionally a carbohydrate or polyhydric alcohol tonicifier and, a preservative selected from the group consisting of m-cresol, benzyl alcohol, methyl, ethyl, propyl and butyl parabens and phenol may also be added. A sufficient amount of water for injection is used to obtain the desired concentration of solution. Additional tonicifying agents such as sodium chloride, as well as other excipients, may also be present, if desired. Such excipients, however, must maintain the overall tonicity of the antioxidant compound.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydroxyl ion added does not exceed the capacity of the buffer system to neutralize it.

The stability of the parenteral formulation of the present invention is enhanced by maintaining the pH of the formulation in the range of approximately 5.0 to 9.5. Other pH ranges, for example, include, 5.5 to 9.0, or 6.0 to 8.5, or 6.5 to 8.0, or 7.0 to 7.5.

The buffer used in the practice of the present invention is selected from any of the following, for example, an acetate buffer, a phosphate buffer or glutamate buffer, the most preferred buffer being a phosphate buffer.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, polyethylene glycols and physiologically compatible solvents.

A stabilizer may be included in the present formulation but, and importantly, is not needed. If included, however, a stabilizer useful in the practice of the present invention is a carbohydrate or a polyhydric alcohol. The polyhydric alcohols include such compounds as sorbitol, mannitol, glycerol, and polyethylene glycols (PEGs). The carbohydrates include, for example, mannose, ribose, trehalose, maltose, inositol, lactose, galactose, arabinose, or lactose.

Suitable stabilizers include, for example, polyhydric alcohols such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000).

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular agent will be effective in one formulation but not effective in another formulation.

A preservative is, in the common pharmaceutical sense, a substance that prevents or inhibits microbial growth and may be added to a pharmaceutical formulation for this purpose to avoid consequent spoilage of the formulation by microorganisms. While the amount of the preservative is not great, it may nevertheless affect the overall stability of the antioxidant compound. Thus, even selection of a preservative can be difficult.

While the preservative for use in the practice of the present invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

A detailed description of each preservative is set forth in "Remington's Pharmaceutical Sciences" as well as Pharmaceutical Dosage Forms: Parenteral Medications, Vol. 1, 1992, Avis et al. For these purposes, the crystalline trientine dihydrochloride salt may be administered parenterally (including subcutaneous injections, intravenous, intramuscular, intradermal injection or infusion techniques) or by inhalation spray in dosage unit formulations containing conventional non-toxic pharmaceutically-acceptable carriers, adjuvants and vehicles.

It may also be desirable to add sodium chloride or other salt to adjust the tonicity of the pharmaceutical formulation, depending on the tonicifier selected. However, this is optional and depends on the particular formulation selected. Parenteral formulations must be isotonic or substantially isotonic otherwise significant irritation and pain would occur at the site of administration.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Generally, the composition is isotonic with the blood of the subject.

If desired, the parenteral formulation may be thickened with a thickening agent such as methyl cellulose. The formulation may be prepared in an emulsified form, either water in oil or oil in water. Any of a wide variety of pharmaceutically acceptable emulsifying agents may be employed including, for example, acacia powder, a non-ionic surfactant or an ionic surfactant.

It may also be desirable to add suitable dispersing or suspending agents to the pharmaceutical formulation these may include, for example, aqueous suspensions such as synthetic and natural gums i.e. tragacanth, acacia, alginate, dextran, sodium carboxymethylcellulose, methylcellulose, polyvinylpyrrolidone or gelatin.

The vehicle of greatest importance for parenteral products is water. Water of suitable quality for parenteral administration must be prepared either by distillation or by reverse osmosis. Only by these means is it possible to separate adequately various liquid, gas and solid contaminating substances from water. Water for injection is the preferred aqueous vehicle for use in the pharmaceutical formulation of the present invention. The water may be purged with nitrogen gas to remove any oxygen or free radicals of oxygen from the water.

It is possible that other ingredients may be present in the parenteral pharmaceutical formulation of the present invention. Such additional ingredients may include wetting agents, oils (e.g., a vegetable oil such as sesame, peanut or olive), analgesic agents, emulsifiers, antioxidants, bulking agents, tonicity modifiers, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Containers are also an integral part of the formulation of an injection and may be considered a component, for there is no container that is totally insoluble or does not in some way affect the liquid it contains, particularly if the liquid is aqueous. Therefore, the selection of a container for a particular injection must be based on a consideration of the composition of the container, as well as of the solution, and the treatment to which it will be subjected.

In order to permit introduction of a needle from a hypodermic syringe into a multiple-dose vial and provide for resealing as soon as the needle is withdrawn, each vial is sealed with a rubber closure held in place by an aluminum band.

Stoppers for glass vials, such as, West 4416/50, 4416/50 (Teflon faced) and 4406/40, Abbott 5139 or any equivalent stopper can be used as the closure for the dose vial. These stoppers pass the stopper integrity test when tested using patient use patterns, e.g., the stopper can withstand at least about 100 injections.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above formulation involves compounding, sterile filtration and filling steps. The compounding procedure, may for example, involve the dissolution of ingredients in a specific order, such as the preservative first followed by the stabilizer/tonicity agents, buffers and then the antioxidant compound or dissolving all of the ingredients forming the parenteral formulation at the same time. An example of one method of preparing a parenteral formulation for administration is the dissolution of the antioxidant compound form, for example, Mitoquinone-C10 mesylate-β-cyclodextrin (1:2), in water and diluting the resultant mixture in a phosphate buffered saline.

Alternatively, parenteral formulations of the present invention are prepared by mixing the ingredients following generally accepted procedures. For example, the selected components may be mixed in a blender or other standard device to produce a concentrated mixture which may then be adjusted to the final concentration and viscosity by the addition of water, a thickening agent, a buffer, 5% human serum albumin or an additional solute to control tonicity.

Alternatively, the antioxidant compound can be packaged as a dry solid and/or powder to be reconstituted with a solvent to yield a parenteral formulation in accordance with the present invention for use at the time of reconstitution.

In addition the manufacturing process may include any suitable sterilization process when developing the parenteral formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), radiant exposure and aseptic handling.

Suitable routes of parenteral administration include intravenous, intramuscular, subcutaneous, intradermal, sub dermal, intraarticular, intrathecal, intraperitoneal, and the like. The intravenous route of administration is preferred. Mucosal delivery is also permissible. The dose and dosage regimen will depend upon the weight and health of the subject.

Pharmaceutically acceptable carriers, excipients, diluents, complexation agents, or additives may be chosen so as to, for example, enhance the stability of the antioxidant compound, facilitate synthesis or formulation of a pharmaceutical formulation, and/or to enhance the bioavailability of the antioxidant compound.

For example, carrier molecules such as cyclodextrin and derivatives thereof are well known in the art for their potential as complexation agents capable of altering the physicochemical attributes of drug molecules. For example, cyclodextrins may stabilize (both thermally and oxidatively), reduce the volatility of, and alter the solubility of, active agents with which they are complexed. Cyclodextrins are cyclic molecules composed of glucopyranose ring units which form toroidal structures. The interior of the cyclodextrin molecule is hydrophobic and the exterior is hydrophilic, making the cyclodextrin molecule water soluble. The degree of solubility can be altered through substitution of the hydroxyl groups on the exterior of the cyclodextrin. Similarly, the hydrophobicity of the interior can be altered through substitution, though generally the hydrophobic nature of the interior allows accommodation of relatively hydrophobic guests within the cavity. Accommodation of one molecule within another is known as complexation and the resulting product is referred to as an inclusion complex. Examples of cyclodextrin derivatives include sulfobutylcyclodextrin, maltosylcyclodextrin, hydroxypropylcyclodextrin, and salts thereof.

Methods of forming pharmaceutically acceptable composition comprising an inclusion complex of a mitochondrially targeted antioxidant compound, in this case Mitoquinone-C10 in complex with β-cyclodextrin, are disclosed herein in Example 1 and Example 7. Methods of forming pharmaceutically acceptable compositions comprising an inclusion complex of a preferred mitochondrially targeted antioxidant compound Mitoquinone-C10 mesylate in complex with β-cyclodextrin are disclosed herein in Example 9 and Example 10.

The physicochemical properties, including for example the pharmaceutical properties, of the antioxidant compound-cyclodextrin complex can be varied by, for example, variation of the molar ratio of antioxidant compound to cyclodextrin, or variation of the cyclodextrin itself. For example, for the preferred antioxidant compounds of general formula I, the molar ratio of antioxidant compound to cyclodextrin (antioxidant compound:cyclodextrin) may be from about 10:1 to about 1:10, from about 5:1 to about 1:5, from about 4:1 to about 1:4, from about 2:1 to about 1:2, or about 1:1. In a further example, the preferred molar ratio of exemplary antioxidant compound Mitoquinone-C10 to cyclodextrin is 1:2 and the cyclodextrin is β-cyclodextrin.

Alternatively, the pharmaceutically appropriate form of antioxidant compound may be formulated so as to enhance the stability and bioavailability of the antioxidant compound. For example, enteric coatings may be applied to tablets to prevent the release of the antioxidant compound in the stomach either to reduce the risk of unpleasant side effects or to maintain the stability of the antioxidant compound which might otherwise be subject to degradation by exposure to the gastric environment. Most polymers that are used for this purpose are polyacids that function by virtue of the fact that their solubility in aqueous medium is pH-dependent, and they require conditions with a pH higher than normally encountered in the stomach.

One preferable type of oral controlled release structure is enteric coating of a solid dosage form. Enteric coatings promote the compounds remaining physically incorporated in the dosage form for a specified period when exposed to gastric juice, yet the enteric coatings are designed to disintegrate in intestinal fluid for ready absorption. Delay of absorption is dependent on the rate of transfer through the gastrointestinal tract, and so the rate of gastric emptying is an important factor. For some administrations, a multiple-unit type dosage form, such as granules, may be superior to a single-unit type. Therefore, in one embodiment, antioxidant compounds of the invention may be contained in an enterically coated multiple-unit dosage form. In a more preferable embodiment, the antioxidant compound dosage form is prepared by producing particles having an antioxidant compound-enteric coating agent solid on an inert core material. These granules can result in prolonged absorption of the antioxidant compound with good bioavailability.

Typical enteric coating agents include, but are not limited to, hydroxypropylmethylcellulose phthalate, methacrylic acid-methacrylic acid ester copolymer, polyvinyl acetate-phthalate and cellulose acetate phthalate.

Examples of preferred antioxidant compounds of the present invention and/or formulations and/or complexes thereof exhibit advantageous pharmaceutical properties. For example, they are readily formulatable, are chemically and physically stable, are readily water soluble, have low hygroscopicity and exhibit good shelf life.

The invention will now be described in more detail with reference to the following non-limiting experimental section.

Example 1

Synthesis of Mitoquinone-C10

The following describes a preferred method of synthesis of a preferred stable salt form of the exemplary mitochondrially targeted antioxidant compound Mitoquinone-C10, Mitoquinone-C10 mesylate, and a cyclodextrin complex thereof.

Stage 1

Scheme:

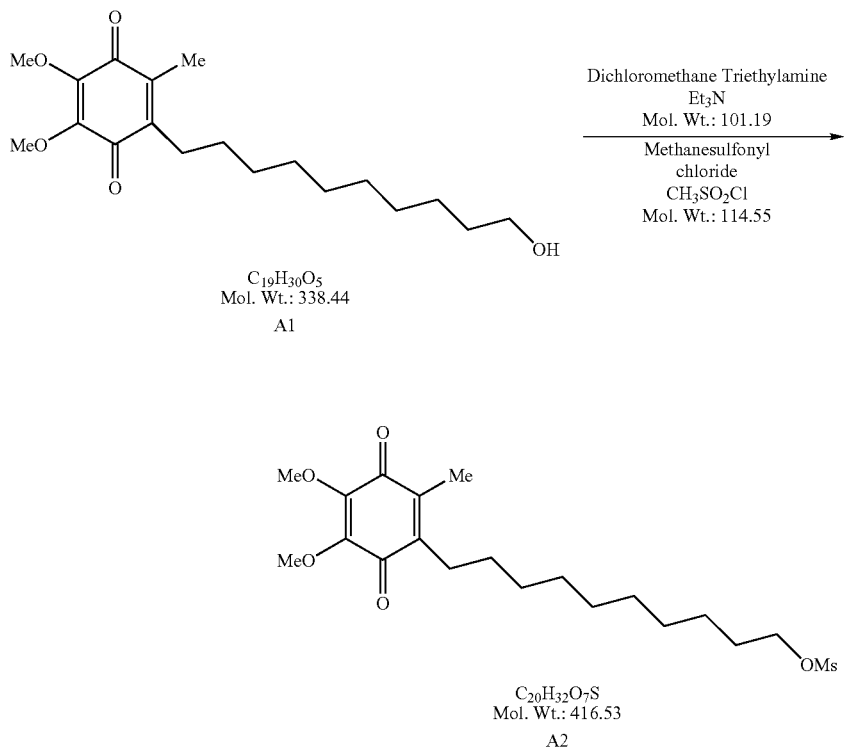

Step:

1. Idebenone (A1, 0.25 kg, 0.74 mol) is dissolved in 2.5 L of reaction grade DCM, and the mixture is then cooled to 10±3° C. under an inert atmosphere.

2. Triethylamine (0.152 kg, 1.5 mol) is added in one portion at ambient temperature and the mixture allowed to re-equilibrate to 10±3° C.

3. A solution of methanesulfonyl chloride (0.094 kg, 0.82 mol) in 0.5 L of DCM is then added gradually at such a rate as to maintain an internal temperature of approx. 10-15° C. (On this scale the addition was complete after 75 minutes).

4. The reaction mixture is agitated for a further 15-30 minutes,

5. IPC checked for completion by TLC($R_f$ 0.65 5% Ethanol/Dichloromethane).

6. The mixture is then washed with water (0.85 L) and saturated aqueous sodium bicarbonate solution (0.85 L).

7. The organic layer is evaporated to a red liquid under reduced pressure at 40-45° C. After drying for an additional 2-4 hours under high vacuum at ambient temperature, the crude A2 so obtained is used directly in the next step. Yield unknown as solvent was trapped in the liquid.

Stage 2

Scheme:

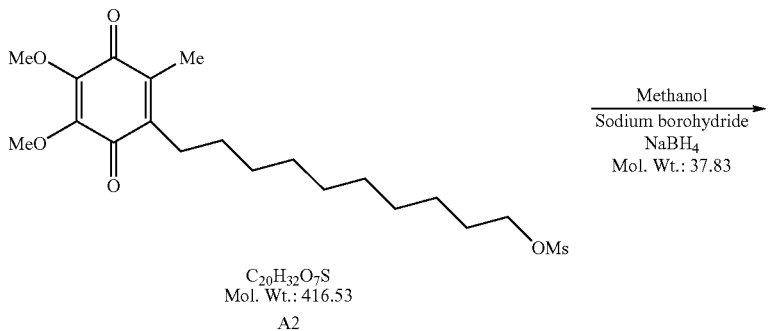

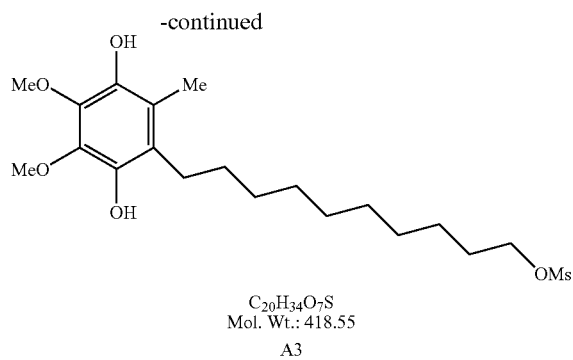

C₂₀H₃₄O₇S
Mol. Wt.: 418.55
A3

Step:
1. Idebenone mesylate (A2, assume 100% yield from last step, 0.31 kg, 0.74 mol) is dissolved in 2 L of methanol and the mixture then cooled to 0-5° C. under an inert atmosphere.
2. Sodium borohydride (0.03 kg, 0.79 mol) is added portionwise at such a rate as to ensure that the internal temperature doe not exceed 15° C. Completion of reaction will be accompanied by a colour change: red yellow (On this scale the addition was complete after 20 minutes).
3. The reaction mixture is agitated for a further 10-30 minutes,
4. IPC checked for completion by TLC (A3 $R_f$ 0.60 5% Ethanol/Dichloromethane, A2 $R_f$ 0.65).

5. The mixture is then quenched with 2 L of 2M hydrochloric acid solution and extracted three times with 1.2 L of dichloromethane.
6. The combined organic phases are then washed once with 1.2 L of water and dried over anhydrous magnesium sulfate (0.24 kg).
7. The organic phase is then evaporated to a yellow/brown syrup under reduced pressure at 40-45° C. After drying for an additional 2-8 hours under high vacuum at ambient temperature, the crude product A3, 0.304 kg 98% yield, so obtained is used directly in the next step.

Stage 3

Scheme:

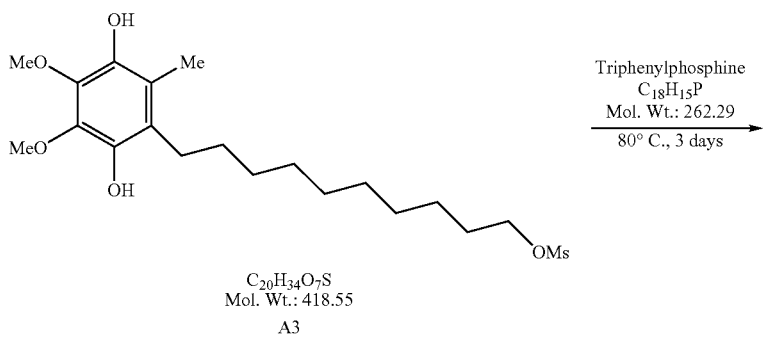

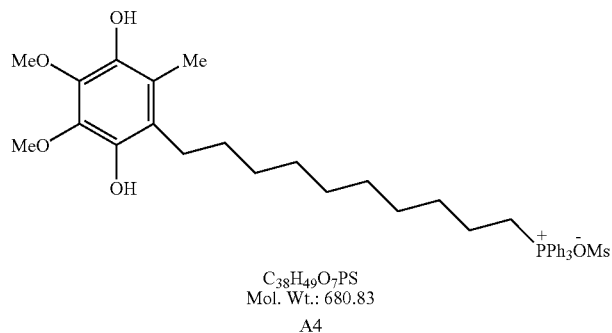

C₃₈H₄₉O₇PS
Mol. Wt.: 680.83
A4

Step:
1. Triphenylphosphine chunks (0.383 kg 1.46 mol) are added to Idebenol mesylate (A3, 0.304 kg, 0.73 mol) in a suitably sized round-bottomed flask.
2. The flask is then attached to a rotary evaporator and the contents heated under vacuum to a bath temperature of 80-85° C.
3. The mixture should form a homogeneous melt at this temperature. Once a melt has formed and degassing is no longer evident, the vacuum is displaced with an inert atmosphere and the mixture is spun gently in a bath set to 80-85° C. for approx. 3 days.
4. IPC check for completion by $^1$H and $^{31}$P NMR. A minimum of 95% conversion is required before workup can take place.
5. The mixture is then cooled to near room temperature and dissolved in 0.8 L of dichloromethane.
6. 3.2 L of ethyl acetate is then added in portions with gentle warming to precipitate the desired product away from excess triphenylphosphine.
7. A small volume of solvent is removed by evaporation under reduced pressure (to remove DCM) and the remaining mixture is then cooled to near ambient temperature and decanted.
8. The remaining syrupy residue is then subjected to the same washing procedure twice more and then finally dried under high vacuum to constant weight to afford a tan foam 0.441 kg 89% yield (NOTE: product still contained some solvent, see nmr). A4 so obtained is used directly in the next step.

Stage 4

Step:
1. The crude mitoQuinol mesylate salt (0.44 kg, assume 0.65 mol) is dissolved in 6 L of anhydrous DCM and the flask is purged with oxygen.
2. The flask contents are vigorously stirred under an oxygen atmosphere for 30 minutes to ensure saturation of the solvent with the gas.
3. A 0.1 L solution of 0.65M $NO_2$ in dry DCM (2 mol % $NO_2$) is added rapidly in one portion and the mixture is vigorously stirred under an oxygen atmosphere for 4-8 hours at ambient temperature.
4. An IPC check for completion (by $^1$H NMR and optionally $^{31}$P NMR) is then carried out.
5. If the oxidation is incomplete a further 2 mol % of $NO_2$ as a solution in DCM is added. This should drive the reaction to completion. IPC check as above. On this scale 8 mol % of $NO_2$ as a solution in DCM was required for the reaction to reach completion.
6. The solvent is then removed by evaporation under reduced pressure to afford a red syrupy residue. This residue is dissolved in 2 L of dichloromethane at 40-45° C.
7. 3.2 L of ethyl acetate is then added in portions with gentle warming to precipitate the desired product. A small volume of solvent is removed by evaporation under reduced pressure (to remove DCM) and the remaining mixture is then cooled to near ambient temperature and decanted.
8. The oily residue is then finally dried under high vacuum to constant weight to afford a red glass (419 g, 94% yield). A5 so obtained is used directly in the next step.

Scheme:

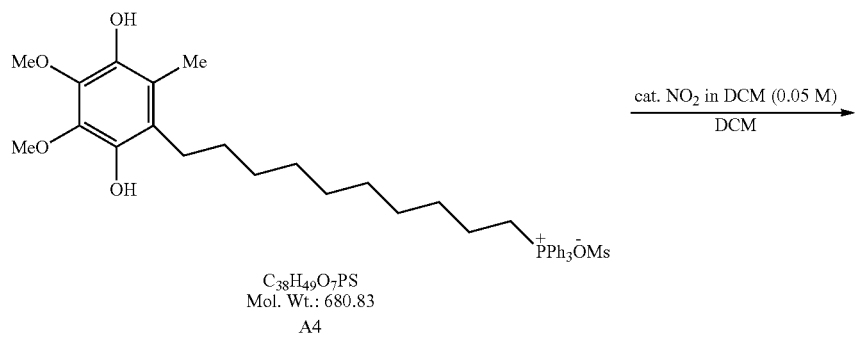

$C_{38}H_{49}O_7PS$
Mol. Wt.: 680.83
A4 cat. $NO_2$ in DCM (0.05 M)
―――――――→
DCM

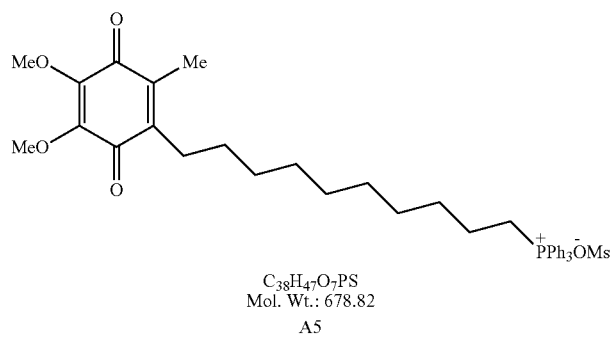

$C_{38}H_{47}O_7PS$
Mol. Wt.: 678.82
A5

Stage 5

Scheme:

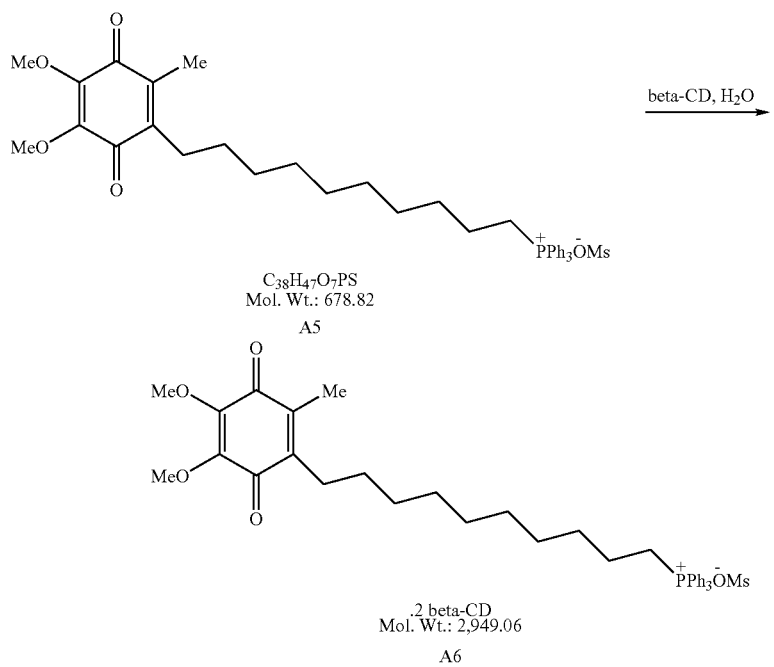

Step:
1. The crude mitoQuinone mesylate salt (A5 0.419 kg) is dissolved in 6 L of water with gentle heating at 40-43° C.
2. The beta-cyclodextrin, 1.24 kg, is separately dissolved in 20 L of water, with heating at 60° C.
3. These two solutions are cooled to approximately room temperature and combined to form a homogeneous mixture. This solution should be stored at <5° C.
4. This orange solution is then frozen at −20° C. and lyophilised in batches to constant weight (at least 48 hours).
5. The resultant solid is then gently crushed to form a uniform free flowing yellow/orange powder (1.433 kg).

An alternative synthetic method has been performed wherein the oxidation step 3 of stage 4 of the synthetic method described above was achieved by bubbling oxygen through the solution, indicating the oxidation reaction may be driven substantially to completion by oxidative means other than oxidation with $NO_2$.

Example 2

Synthesis of Mitochondrially Targeted Antioxidant Compounds

The chemical syntheses of Mitoquinone-C3, Mitoquinone-C5 and Mitoquinone-C15 are outlined in FIG. 2 and are described below. Nuclear magnetic resonance spectra were acquired using a Varian 300 MHz instrument. For $^1$H-NMR tetramethylsilane was the internal standard in $CDCl_3$. For $^{31}$P NMR 85% phosphoric acid was the external standard. Chemical shifts (δ) are in ppm relative to the standard. Elemental analyses were done by the Campbell Microanalytical Laboratory, University of Otago. Electrospray mass spectrometry was done using a Shimadzu LCMS-QP800X liquid chromatography mass spectrometer. Stock solutions were prepared in absolute ethanol and stored at −20° C. in the dark.

Figure 2A:
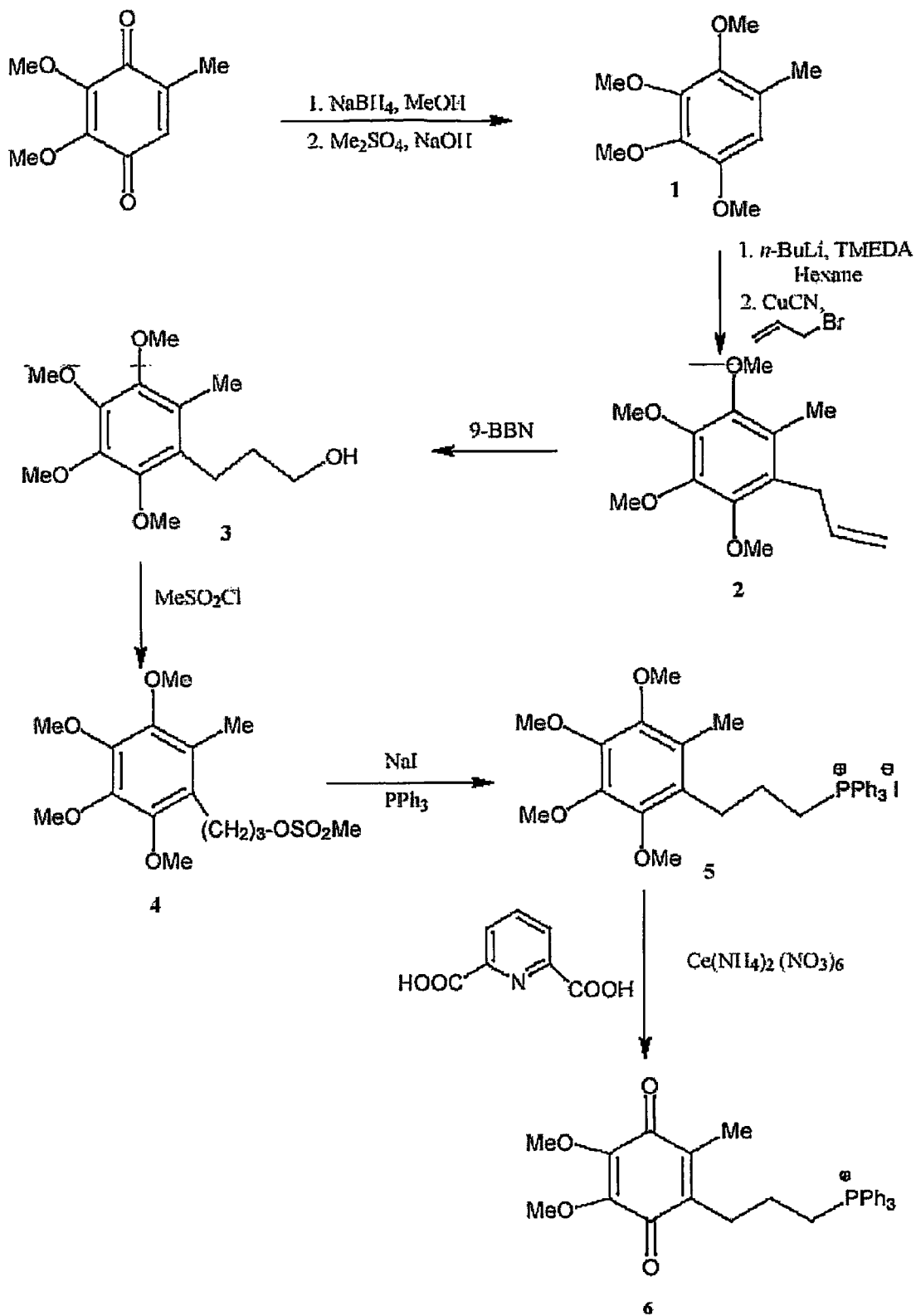
FIG. 2 depicts the synthetic pathways for A: Mitoquinone-C3; B: Mitoquinone-C5; C: Mitoquinone-C15.

Mitoquinone-C3 (6). The synthetic route to Mitoquinone-C3 is shown in FIG. 2A. The starting material, 2,3,4,5-tetramethoxytoluene (1) (Lipshutz, B. H., Kim, S.-k., Mollard, P. and Stevens, K. L. (1998) Tetrahedron 54, 1241-1253) was prepared by reducing 2,3-dimethoxy-5-methyl-1,4-benzoquinone ($CoQ_0$) to the hydroquinol (Carpino, L. A., Triolo, S. A. and Berglund, R. A. (1989) J. Org. Chem. 54, 3303-3310) followed by methylation to give 1 (Lipshutz, B. H., Kim, S.-k., Mollard, P. and Stevens, K. L. (1998) Tetrahedron 54, 1241-1253). A solution of 1 (6.35 g, 29.9 mmol) in dry hexane (80 mL) and N,N,N',N'-tetramethylethylenediamine (8.6 mL) was placed with a flame-dried stirrer bar in a flame-dried Schlenk tube under nitrogen. A hexane solution of n-butyl lithium (1.6 M, 26.2 mL) was slowly added at room temperature and the mixture was cooled and stirred at 0° C. for 1 hr. After being cooled to −78° C., dry tetrahydrofuran (THF; 250 mL) was added, and a small aliquot of the reaction mixture was removed, quenched with $D_2O$ and examined by $^1$H NMR to assure complete metallation. The yellow suspension was then transferred to a second flame-dried Schlenk tube containing CuCN (0.54 g, 6.03 mmol) under nitrogen at −78° C. The mixture was warmed to 0° C. for 10 mins, then cooled to −78° C. and allyl bromide (3.62 mL) was added and the reaction was stirred overnight (19 hrs) and allowed to warm to room temperature. The reaction was quenched with 10% aqueous $NH_4Cl$ (75 mL), and extracted with ether (2×200 mL). The combined ethereal extracts were washed with $H_2O$ (2×150 mL), 10% aqueous $NH_4OH$ (200 mL) and saturated aqueous NaCl (200 mL). The organic solvents were dried over $MgSO_4$, filtered and the solvent removed by rotary evaporation in vacuo to give a crude product (7.25 g). Column chromatography on silica gel and elution with 20% ether/ hexane gave pure 1,2,3,4-tetramethoxy-5-methyl-6-(2-propenyl)benzene (2) (Yoshioka, T., Nishi, T., Kanai, T., Aizawa, Y., Wada, K., Fujita, T. and Horikoshi, H. (1993), Eur. Pat. Appl. EP 549366 A1) (6.05 g, 83.5%). $^1$H NMR δ 5.84-5.98 (1H, m, —CH=C), 4.88-5.03 (2H, m, =CH$_2$), 3.78, 3.80, 3.90, 3.92 (12H, s, OMe), 3.38 (2H, d, J=7.0 Hz, Ar—CH$_2$), 2.14 (3H, s, Ar-Me) ppm.

A solution of 2 (8.0 g, 33.05 mmol) in dry THF (45 mL) was added dropwise over 20 mins under argon to a stirred suspension of 9-borabicyclo[3,3,1]nonane in THF (79 mL, 39.67 mmol, 0.5 M) at 25° C. The resulting solution was stirred overnight at room temperature and for a further 2 hrs at 65° C. under argon. The mixture was then cooled to 0° C. and 3 M NaOH (53 mL) was then added dropwise followed by 30% aqueous H$_2$O$_2$ (53 mL). After 30 mins stirring at room temperature, the water phase was saturated with NaCl and extracted 3 times with THF. The combined organic fractions were washed with saturated aqueous NaCl, dried (Na$_2$SO$_4$), filtered and evaporated to give an oily residue (11.5 g) which was purified by column chromatography on silica gel (200 g, packed with ether/hexane 1:9). Elution with ether/hexane 1:4 gave pure 3-(2,3,4,5-tetramethoxy-6-methyl-phenyl)-propan-1-ol (3) as a viscous, colourless oil (6.85 g, 80%). $^1$H NMR δ 3.91, 3.90, 3.84, 3.79 (12H, s, OMe), 3.56 (2H, t, J=7.0 Hz, —CH$_2$—OH), 2.72 (2H, t, J=7.0 Hz, Ar—CH$_2$), 2.17 (3H, s, Ar-Me), 1.74 (2H, quintet, J=7.0 Hz, —CH$_2$—) ppm. Anal. calcd. for C$_{14}$H$_{22}$O$_5$: C, 62.2; H, 8.2. Found: C, 62.2; H, 8.4%.

A solution of 3 (3.88 g, 15 mmol) and triethylamine (3.0 g, 30 mmol, 4.2 mL) in CH$_2$Cl$_2$ (50 mL) was stirred at room temperature for 10 mins. Methanesulfonyl chloride (1.8 g, 1.20 mL, 15.75 mmol) in CH$_2$Cl$_2$ (50 mL) was added dropwise over 20 mins and the reaction mixture stirred at room temperature for 1 hr. The mixture was then diluted with CH$_2$Cl$_2$ (50 mL) and the organic layer was washed with H$_2$O (5×100 mL), 10% aqueous NaHCO$_3$ (100 mL), dried (MgSO$_4$), filtered and the solvent removed in vacuo by rotary evaporation to afford 1-(3-methanesulfonyloxypropyl)-2-methyl-3,4,5,6-tetramethoxybenzene (4) as a liquid (4.8 g, 95%). $^1$H NMR δ4.277 (2H, t, J=7.0 Hz, —CH$_2$—O—SO$_2$-Me), 3.91, 3.89, 3.82, 3.78 (12H, s, OMe), 3.03 (3H, s, —O—SO$_2$-Me), 2.70 (2H, t, J=7.0 Hz, Ar—CH$_2$—), 2.17 (3H, s, Ar-Me), 1.9 (2H, m, —CH$_2$—) ppm.

The crude methanesulfonate 4 (3.30 g, 9.8 mmol) was used directly in the following reaction by mixing with a freshly ground mixture of triphenylphosphine (4.08 g, 15.6 mmol) and NaI (7.78 g, 51.9 mmol) in a Kimax tube and sealed under argon. The mixture was then held at 70-74° C. with magnetic stirring for 3 hrs during which time the mixture changed from a molten thick liquid into a glassy solid. The tube was cooled to room temperature and the residue stirred with CH$_2$Cl$_2$ (30 mL). The suspension was then filtered and the filtrate evaporated in vacuo. The residue was dissolved in a minimum amount of CH$_2$Cl$_2$ and triturated with excess ether (250 mL) to precipitate the white solid. The solid was filtered and washed with ether, dried in vacuo to give pure [3-(2,3,4,5-tetramethoxy-6-methyl-phenyl)-propyl]triphenylphosphonium iodide (5) (5.69 g, 90%). $^1$H NMR δ 7.82-7.65 (15H, m, Ar—H), 3.88, 3.86, 3.74, 3.73 (12H, s, OMe), 3.76-3.88 (2H, m, CH$_2$—P$^+$), 2.98 (2H, t, J=7.0 Hz, CH$_2$—Ar), 2.13 (3H, s, Ar-Me), 1.92-1.78 (2H, m, —CH$_2$—) ppm. $^{31}$P NMR (121.4 MHz) δ 25.32 ppm. Anal. calcd. for C$_{32}$H$_{36}$IO$_5$P: C, 59.8; H, 5.7; P, 4.8. Found: C, 59.8; H, 5.8; P, 4.5%.

A solution of the iodide form of 5 (4.963 g, 7.8 mmol) in CH$_2$Cl$_2$ (80 mL) was shaken with 10% aqueous NaNO$_3$ (50 mL) in a separatory funnel for 5 mins. The organic layer was separated, dried (Na$_2$SO$_4$), filtered and evaporated in vacuo to give the nitrate salt of 5 (4.5 g, 7.8 mmol, 100%), which was dissolved in a mixture of CH$_3$CN and H$_2$O (7:3, 38 mL) and stirred at 0° C. in an ice bath. Pyridine-2,6-dicarboxylic acid (6.4 g, 39 mmol) was then added followed by dropwise addition of a solution of ceric ammonium nitrate (21.0 g, 39 mmol) in CH$_3$CN/H$_2$O (1:1, 77 mL) over 5 mins. The reaction mixture was stirred at 0° C. for 20 mins and then at room temperature for a further 10 mins. The reaction mixture was then poured into H$_2$O (200 mL) and extracted with CH$_2$Cl$_2$ (200 mL), dried (Na$_2$SO$_4$), filtered and evaporated in vacuo to give a crude [3-(4,5-dimethoxy-2-methyl-3,6-dioxo-1,4-cyclohexadien-1-yl)propyl]triphenylphosphonium (6) nitrate. The total product was dissolved in CH$_2$Cl$_2$ (100 mL) and shaken for 10 mins with 20% aqueous KBr (50 mL). The organic layer was separated, dried and evaporated in vacuo to give the bromide salt of 6 (4.1 g, 93.6%). $^1$H NMR δ 7.90-7.65 (15H, m, Ar—H), 4.15-4.05 (2H, m, CH$_2$—P$^+$), 3.96, 3.95, (6H, s, OMe), 2.93 (2H, t, J=7.0 Hz, CH$_2$—Ar), 2.15 (3H, s, Ar-Me), 1.85-1.70 (2H, m, —CH$_2$—) ppm. $^{31}$P NMR δ 25.29 ppm.

A solution of 6 bromide (3.65 g, 6.5 mmol) in CH$_2$Cl$_2$ (75 mL) was shaken with a 10% w/v aqueous solution of sodium methanesulfonate (100 mL) in a separatory funnel for 5 mins. The CH$_2$Cl$_2$ layer was separated, dried (Na$_2$SO$_4$), filtered and evaporated in vacuo to give [3-(4,5-dimethoxy-2-methyl-3,6-dioxo-1,4-cyclohexadien-1-yl)propyl]triphenylphosphonium methanesulfonate salt (6) (3.7 g, 98%). $^1$H NMR δ 7.88-7.60 (15H, m, Ar—H), 3.93, 3.92, (6H, s, OMe), 3.90-3.78 (2H, m, CH$_2$—P$^+$), 2.85 (2H, t, J=7.0 Hz, CH$_2$—Ar), 2.70 (3H, s, OSO$_2$CH$_3$), 2.09 (3H, s, Ar-Me), 1.82-1.68 (2H, m, —CH$_2$—) ppm. $^{31}$P NMR (121.4 MHz) δ 25.26 ppm. Anal. calcd. for C$_{31}$H$_{33}$O$_7$PS: C, 64.1; H, 5.7; P, 5.3; S, 5.5. Found: C, 63.8; H, 5.9; S, 5.3; P, 5.2%.

Figure 2B:
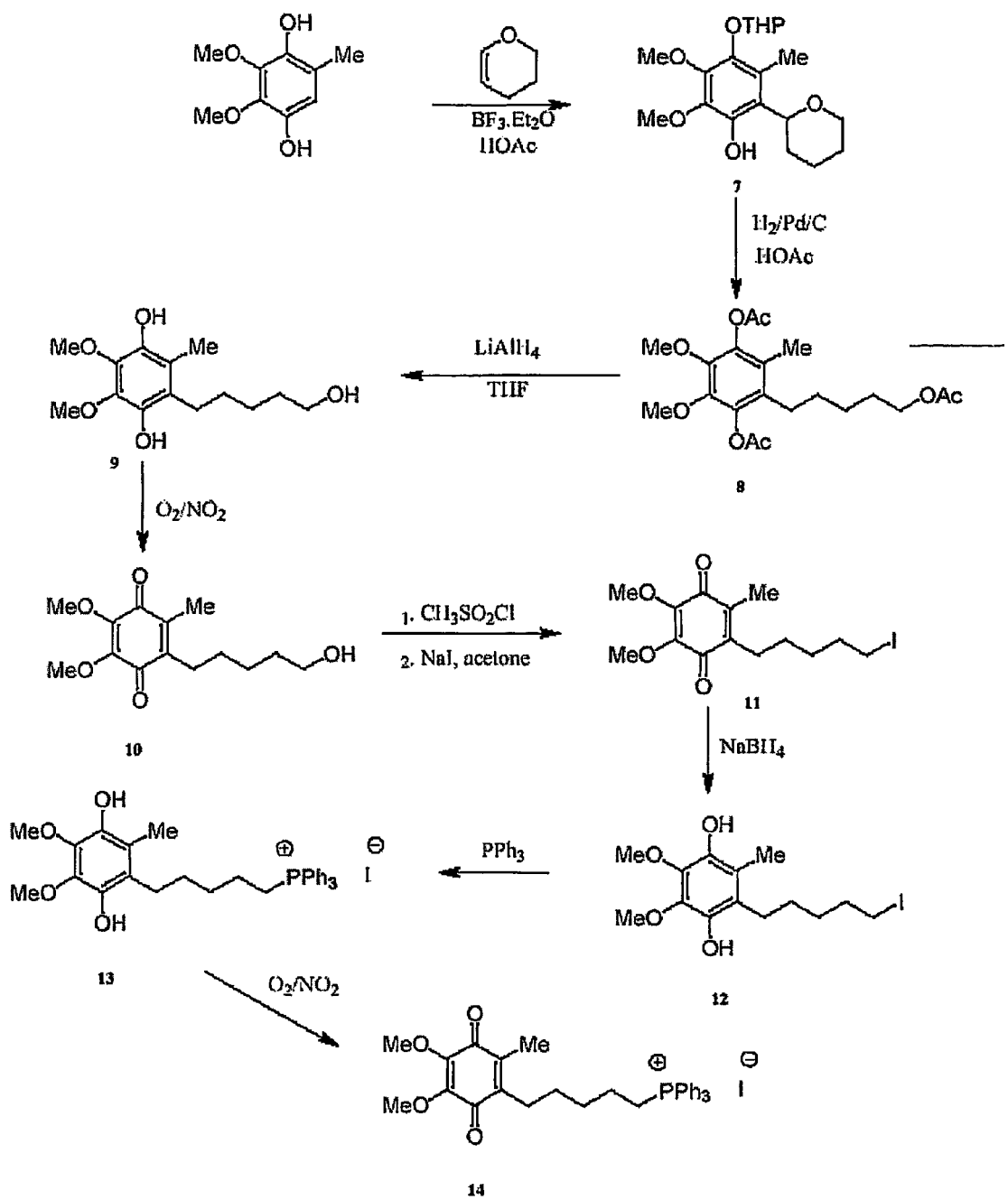

Mitoquinone-C5 (14). The synthetic route to Mitoquinone-C5 is shown in FIG. 2B. Dihydropyran (46.83 g, 0.55 mol) was added to 2,3-dimethoxy-5-methyl-1,4-benzohydroquinone (CoQ$_0$) (50 g, 0.275 mol) dissolved in acetic acid (500 mL) and stirred at room temperature for 10 minutes. To this solution was added BF$_3$.Et$_2$O (38.57 g, 0.271 mol). The resulting solution was stirred for 18 hours at room temperature. After this time the crude reaction mixture was poured into iced water (500 mL) and extracted with chloroform (1000 mL). The organic extract was washed with brine (500 mL) and dried (MgSO$_4$). The solvent was removed in vacuo to give the crude 2,3-dimethoxy-5-methyl-6-(tetrahydro-pyran-2-yl)-4-(tetrahydro-pyran-2-yloxy)-phenol (7) as a red oil (115 g) which was used without further purification. A solution of crude 7 (110 g) in a mixture of acetic acid/perchloric acid (97.5:2.5, 500 mL) was hydrogenated over 5% palladium/charcoal (5.42 g) at atmospheric pressure and room temperature until hydrogen uptake ceased (three days). The reaction mixture was then filtered through a pad of Celite, and the solid residue washed with ethanol (500 mL). The combined filtrate was divided into three equal portions and each portion added to distilled water (1000 mL) and extracted with CH$_2$Cl$_2$ (2×200 mL). The combined organic extracts were washed with brine (500 mL), saturated sodium bicarbonate (500 mL), brine (300 mL) and then dried (NgSO$_4$). The mixture was then filtered and solvents were removed in vacuo to give crude 4-acetoxy-3-(5-acetoxy-pentyl)-5,6-dimethoxy-2-methyl-phenyl acetate (8) as a red oil (110 g) which was used in the subsequent step without further purification. $^1$H NMR δ4.0-4.15 (2H, m, —CH$_2$—O), 3.86 (6H, s, 2×OMe), 2.58 (2H, t, J=7.0 Hz, —CH$_2$—Ar), 2.12 (3H, s, Ar-Me), 2.06 (6H, s, 2×CH$_3$—C=O), 2.02 (3H, s, CH$_3$—C=O), 1.35-1.70 (6H, m, —CH$_2$CH$_2$CH$_2$—) ppm.

Lithium aluminium hydride (8.0 g, 0.21 mol) was added to dry THF (500 mL) in a 1 L round bottomed flask equipped with a magnetic stirrer, reflux condenser and surrounded by a room temperature water bath. A solution of crude 8 (74 g) in dry freshly distilled THF (100 mL) and was added dropwise to the THF/LiALH$_4$ mixture over a period of 25-30 minutes. Additional dry THF (200 mL) was added, to facilitate stirring, and the reaction was left stirring for 3 hours at room temperature. The reaction was then quenched by the dropwise addition of 3 M HCl (20 mL) followed by the slow addition of distilled water (70 mL). The reaction mixture was then filtered and the filtrate was washed with brine (2×300 mL), dried (MgSO$_4$), filtered and the solvent removed in vacuo. The green residue remaining in the filter funnel was dissolved in 15% HCl (500 mL) and extracted with CH$_2$Cl$_2$ (1×300 ml, 2×200 ml). The organic fractions were combined and washed with brine (400 ml), dried (MgSO$_4$), filtered and evaporated in vacuo. This extract was combined with the material from the filtrate workup to give crude 2-(5-hydroxypentyl)-5,6-dimethoxy-3-methyl-benzene-1,4-diol (9)(68.3 g) as a red oil. This product 9 was purified using column chromatography on silica gel, (600 g, packed in 10% ether/CH$_2$Cl$_2$). Elution with 10% ether/CH$_2$Cl$_2$ gave some unreacted 8 and 2,3-dimethoxy-5-methyl-1,4-benzohydroquinone starting material. Elution with 20% ether/CH$_2$Cl$_2$, gave a mixture of 9 and the quinone 10 (14.14 g, 19% from 2,3-dimethoxy-5-methyl-1,4-benzoquinol). Compound 9 was slowly converted to the quinone 10 on standing in air and satisfactory elemental analysis could not be obtained. $^1$H NMR δ 5.41 (1H, s, Ar—OH), 5.38 (1H, s, Ar—OH), 4.88 (6H, s, 2×Ar—OMe), 3.65 (2H, t, J=6.3 Hz, CH$_2$—OH), 2.61 (2H, t, J=6.4 Hz, Ar—CH$_2$), 2.14 (3H, s, Ar-Me), 1.42-1.68 (6H, m, 3×-CH$_2$—) ppm.

A solution of the quinol 9 (7.5 g, 27.7 mmol) in CH$_2$Cl$_2$ (150 mL) was saturated with oxygen gas at atmospheric pressure and a solution of NO$_2$ in CH$_2$Cl$_2$ (1 ml, 1.32 M) was added. The reaction was stirred at room temperature under an oxygen atmosphere for 18 hours by which time TLC (40% ether/CH$_2$Cl$_2$) showed the formation of the quinone 2-(5-hydroxypentyl)-5,6-dimethoxy-3-methyl-[1,4]benzoquinone (10) was complete. The solvent was then removed in vacuo to afford the product 10 (Yu, C. A. and Yu, L. (1982) Biochemistry 21, 4096-4101)(7.40 g) as a red oil. $^1$H NMR δ 3.99 (6H, s, 2×Ar—OMe), 3.65 (2H, t, J=6.3 Hz, CH$_2$—OH), 2.47 (2H, t, J=6.3 Hz, Ar—CH$_2$), 2.01 (3H, s, Ar-Me), 1.52-1.60 (2H, m, —CH$_2$—), 1.37-1.43 (4H, m, —CH$_2$CH$_2$—) ppm.

A solution of 10 (7.40 g, 27.3 mmol) in CH$_2$Cl$_2$ (150 mL) and triethylamine (5.46 g, 5.46 mmol) was prepared and a solution of methanesulfonyl chloride (2.48 g, 30 mmol) in CH$_2$Cl$_2$ (50 mL) was added over 30 minutes with stirring. After stirring for an additional 1.5 hours at room temperature the reaction mixture was washed with distilled water (5×100 mL), saturated sodium bicarbonate (150 mL) and dried (MgSO$_4$). The mixture was filtered and solvent removed in vacuo to give the crude methanesulfonate (9.03 g) as a red oil. $^1$H NMR δ 4.19 (2H, t, J=7.5 Hz, —CH$_2$—OMs), 3.95 (6H, s, 2×Ar—OMe), 2.98 (3H, s, OSO$_2$CH$_3$), 2.44 (2H, t, J=7.5 Hz, Ar—CH$_2$—), 1.98 (3H, s, Ar-Me), 1.75 (2H, quintet, J=7.5 Hz, —CH$_2$—), 1.38-1.48 (4H, m, —CH$_2$—CH$_2$—) ppm. The methanesulfonate was dissolved in 10% (w/v) NaI in acetone (100 mL) and stirred for 44 hours at room temperature. The mixture was then concentrated in vacuo and H$_2$O (100 mL) was added to the residue. The mixture was extracted with CH$_2$Cl$_2$ (3×70 mL) and the combined organic extracts were washed with brine, dried (MgSO$_4$), filtered and the solvent was removed in vacuo to give crude 2-(5-iodopentyl)-5,6-dimethoxy-3-methyl-[1,4]benzoquinone (11). This product was purified by column chromatography on silica gel (150 g). Elution with CH$_2$Cl$_2$ and 10% ether/CH$_2$Cl$_2$ gave pure 11 (7.05 g, 69%) as a red oil. $^1$H NMR δ 3.99 (6H, s, 2×Ar—OMe), 3.18 (2H, t, J=6.9 Hz, CH$_2$—I), 2.47 (2H, t, J=7.2 Hz, Ar—CH$_2$), 2.02 (3H, s, Ar-Me), 1.85 (2H, quintet, J=7.5 Hz, —CH$_2$—), 1.38-1.48 (4H, m, —CH$_2$—CH$_2$—) ppm. Anal. calcd. For C$_{14}$H$_{19}$IO$_4$: C, 44.5; H, 5.1; I, 33.6. Found: C, 44.6; H, 5.1; I, 33.4%.

A solution of 11 (1.14 g, 2.87 mmol) in methanol (20 ml) was treated with NaBH$_4$ (0.16 g, 4.3 mmol) and the mixture turned colourless within 1 minute. After 5 minutes at room temperature 5% aqueous HCl (100 mL) was added and the solution was extracted with CH$_2$Cl$_2$ (2×50 mL). The organic fractions were combined, dried (MgSO$_4$), filtered and the solvent removed in vacuo to give 12 (1.15 g, 100%) as an oxygen sensitive yellow oil which was used without delay. $^1$H NMR δ 5.36, 5.31 (2H, s, Ar—OH), 3.89 (6H, s, 2×Ar—OMe), 3.20 (2H, t, J=7.5 Hz, —CH$_2$—I), 2.62 (2H, t, J=7.5 Hz, —CH$_2$—Ar), 2.15 (3H, s, Me), 1.82-1.92 (2H, m, —CH$_2$—), 1.45-1.55 (4H, m, —CH$_2$—CH$_2$—) ppm. A mixture of 12 (1.15 g, 2.87 mmol) and triphenylphosphine (1.2 g, 4.31 mmol) was placed in a Kimax tube with a stirrer bar. The tube was flushed with argon, firmly sealed and heated and stirred for 14 hrs at 70° C. A dark solid was formed which dissolved in CH$_2$Cl$_2$ (10 mL) and triturated in ether (200 mL) and the white precipitate formed was filtered rapidly. The precipitate, which became sticky on exposure to air, was re-dissolved in CH$_2$Cl$_2$ and evaporated in vacuo to give the crude product [5-(2,5-dihydroxy-3,4-dimethoxy-6-methyl-phenyl)-pentyl]triphenylphosphonium iodide (13) (2.07 g, 115%) as a brown oil. The material was not stable on storage for extended periods and was used as soon as practicable for subsequent reactions. $^1$H NMR δ 7.84-7.68 (15H, m, Ar—H), 5.45 (1H, s, Ar—OH), 5.35 (1H, s, Ar—OH), 3.89 (3H, s, Ar—OMe), 3.87 (3H, s, Ar—OMe), 3.65 (2H, m, —CH$_2$-+ PPh$_3$), 2.54 (2H, t, J=7.0 Hz, Ar—CH$_2$), 2.08 (3H, s, Ar-Me), 1.65-1.75 (2H, m, —CH$_2$—), 1.45-1.55 (4H, m, —CH$_2$CH$_2$—) ppm. $^{31}$P NMR δ 25.43 ppm.

A solution of 13 (2.07 g) in CH$_2$Cl$_2$ (50 mL) was saturated with oxygen gas and a solution of NO$_2$ in CH$_2$Cl$_2$ (0.5 mL, 1.32 M) was added. The reaction was then stirred at room temperature under an oxygen atmosphere for 18 hrs. The solvent was removed in vacuo to afford the crude product [5-(4,5-dimethoxy-2-methyl-3,6-dioxo-1,4-cyclohexadien-1-yl)pentyl]triphenylphosphonium iodide (14) as a red oil. This residue was re-dissolved in CH$_2$Cl$_2$ (10 mL) and triturated in ether (200 mL) to give an initial yellow precipitate which congealed into a red oil in a few minutes. The solvents were decanted and the precipitate dissolved in CH$_2$Cl$_2$ and the solvent removed in vacuo to give the product (14) (1.866 g) as a red oil. An aliquot (0.880 g) of 14 was purified by column chromatography on silica gel (20 g). Elution with CH$_2$Cl$_2$ gave some unidentified purple coloured material. Elution with 5% ethanol/CH$_2$Cl$_2$ gave the pure iodide product 14 (0.606 g) as a red oil. $^1$H NMR δ 7.84-7.68 (15H, m, Ar—H) 3.98 (6H, s, 2×Ar—OMe), 3.65 (2H, m, CH$_2$—P$^+$), 2.40 (2H, t, J=7.5 Hz, Ar—CH$_2$), 2.00 (3H, s, Ar-Me), 1.71 (4H, m, —CH$_2$—), 1.43 (2H, m, —CH$_2$—) ppm. $^{31}$P NMR (121.4 MHz) δ 25.47 ppm. Anal. calcd. for C$_{32}$H$_{36}$IO$_4$P: C, 59.8; H, 5.7; I, 19.8; P, 4.8. Found: C, 60.0; H, 5.3; I, 19.7; P, 4.7%.

Figure 2C:
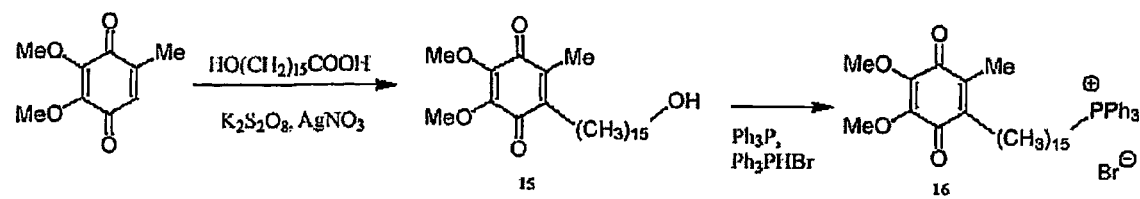

Mitoquinone-C15 (16). The synthetic route to Mitoquinone-C15 is shown in FIG. 2C; A solution of K$_2$S$_2$O$_8$ (0.450 g, 1.66 mmol) in H$_2$O (25 mL) was added dropwise over 2.5 hours to a stirred suspension of AgNO$_3$ (0.262 g, 1.54 mmol), 16-hydroxyhexadecanoic acid (0.408 g, 1.50 mmol), and 2,3-dimethoxy-5-methyl-1,4-benzoquinone (0.271 g, 1.49 mmol) in $H_2O:CH_3CN$ (1:1, 36 mL) held at 75° C. After stirring for 30 minutes the mixture was cooled and extracted with ether (4×30 mL). The combined organic phase was washed with $H_2O$ (2×100 mL), $NaHCO_3$ (1 M, 2×50 mL) and saturated NaCl (2×50 mL). The organic phase was dried ($Na_2SO_4$), filtered and concentrated in vacuo to give a red oil (0.444 g). Column chromatography of the crude oil (silica gel, 15 g) and elution with mixtures of $CH_2Cl_2$ and ether (O %, 5% 20%) gave 2-(15-hydroxypentadecyl)-5,6-dimethoxy-3-methyl-[1,4]benzoquinone (15) (0.192 g, 33%) as a red oil. $^1H$ NMR δ 3.99, 3.98 (6H, s, OMe), 3.64 (2H, t, J=6.5 Hz, —$CH_2OH$), 2.45 (2H, t, J=7.5 Hz, —$CH_2$-ring), 1.4-1.2 (26H, m, —$(CH_2)_{13}$—). Anal. Calcd. for $C_{24}H_{40}O_5$: C, 70.6; H, 9.9. Found: C, 70.5; H, 9.8%.

A mixture of triphenylphosphine (0.066 g, 0.25 mmol), $Ph_3PHBr$ (0.086 g, 0.25 mmol) and 15 (00.101 g, 0.25 mmol) was stirred under argon in a sealed Kimax tube at 70° C. for 24 hours, by which time it had turned into a viscous red oil. The residue was dissolved in minimum $CH_2Cl_2$ (0.5 mL) and poured into ether (10 mL) to produce a red oily precipitate. The solvents were then decanted the residue was dissolved in $CH_3OH$ (0.5 mL) and diluted with $H_2O$ (10 mL) containing 48% HBr (1 drop). A red precipitate formed and after the precipitate had settled the supernatant was poured off and the residue was washed with $H_2O$ (5 mL). The residue was then dissolved in ethanol (5 mL) and the solvent removed in vacuo. The residue was redissolved in $CH_2Cl_2$ (0.5 mL), diluted with ether (5 mL) and the solvent was decanted and the residue placed in a vacuum system (0.1 mbar) for 24 hours to give [15-(4,5-dimethoxy-2-methyl-3,6-dioxo-1,4-cyclohexadien-1-yl)pentadecyl]triphenylphosphonium bromide (16) (0.111 g, 61%) as a yellow foam which turned to a red oil on contact with air. $^1H$ NMR (299 MHz) δ 7.6-8.0 (15H, m, Ar—H), 3.89 (6H, s, OMe), 3.9 (2H, m, —$CH_2$—P), 2.6 (2H, m, —$CH_2$-ring), 1.7-1.1 (26H, m, —$(CH_2)_{13}$—) ppm. $^{31}P$ NMR (121.4 MHz) δ 25.71 ppm. Electrospray mass spectrometry found ($M^+$) 653, calculated for $C_{42}H_{54}O_4P^+$ 653. Combustion analytical results were unsatisfactory due to inconsistent levels of solvent inclusion.

Example 3

Properties of Exemplary Mitochondrially Targeted Antioxidant Compounds

The present invention recognises that, in order to be suitable in a wide variety of applications, for example the formulation of dosage forms such as tablets, there is advantage in being able to form a crystalline or solid form of the mitochondrially targeted antioxidant compound. Similarly, it is believed, without wishing to be bound by any theory, that the antioxidant functionality of the compounds of the present invention are at least in part determined by their physicochemical properties.

The partition coefficients for a variety of antioxidant compounds are shown in Table 1. Octan-1-ol/PBS partition coefficients were determined by adding 400 nmol of the compound to 2 ml PBS-saturated octan-1-ol and mixing for 30 min at 37° C. with 2 ml octan-1-ol saturated PBS. The concentrations of the compound in the two phases were measured by UV absorption at 268 nm and quantitated from standard curves of the compound in octan-1-ol saturated PBS, or PBS-saturated octan-1-ol (Kelso, G. F., Porteous, C. M., Coulter, C. V., Hughes, G., Porteus, W. K., Ledgerwood, E. C., Smith, R. A. J., and Murphy, M. P., 2001, *J Biol Chem* 276, 4588; Smith, R. A. J., Porteous, C. M., Coulter, C. V., and Murphy, M. P. 1999 *Eur J Biochem* 263, 709). Stock solutions of compounds were prepared in absolute ethanol and stored at −20° C. in the dark. [$^3H$]TPMP was from American Radiolabelled Chemicals Inc, (MO, USA).

Of particular note is the low partition coefficient of compounds with small numbers of carbon atoms bridging the antioxidant moiety and the phosphonium. For example, a compound within the present invention, herein referred to as Mitoquinone-C3, which has a 3 carbon bridge has a partition coefficient approximately 50-fold lower than that observed for the related compound, Mitoquinone-C10 (Table 1).

TABLE I

Partition coefficients of antioxidants and related compounds

| Compound | Partition coefficient |
| --- | --- |
| Methyltriphenylphosphonium (TPMP) | [a]0.35 ± 0.02 |
| MitoVit E | [b]7.4 ± 1.6 |
| 4-Bromobutyltriphenylphosphonium | [b]3.83 ± 0.22 |
| 4-Iodobutyltriphenylphosphonium | [c]4.0 ± 0.4 |
| Mitoquinone-C15 | |
| Mitoquinone-C10 | [a]160 ± 9 |
| Mitoquinone-C5 | 13.9 ± 1.9 |
| Mitoquinone-C3 | [c]2.8 ± 0.3 |
| α-Tocopherol | [b]27.4 ± 1.9 |
| Bromodecylubiquinone | [d]310 ± 60 |
| Idebenone | [d]3.1 × 10$^3$ |
| Decylubiquinone | [d]3.1 × 10$^5$ |
| Coenzyme $Q_0$ | [d]1.33 |
| Coenzyme $Q_1$ | [d]409 |
| Coenzyme $Q_2$ | [d]4.44 × 10$^4$ |
| Ubiquinone (Coenzyme $Q_{10}$) | [d]1.82 × 10$^{20}$ |
| Ubiquinol | [d]4.53 × 10$^{20}$ |
| Decylubiquinol | [d]7.91 × 10$^5$ |
| Idebenol | [d]7.82 × 10$^3$ |

Data[a-c] are octan-1-ol/phosphate buffered saline partition coefficients determined at 25° C. or 37° C. as described above, or octanol/water partition coefficients[d] calculated using Advanced Chemistry Development (ACD) Software Solaris V4.67 as described in Jauslin, M. L., Wirth, T., Meier, T., and Schoumacher, F., 2002, *Hum Mol Genet* 11, 3055.
[a]Kelso, G. F., Porteous, C. M., Coulter, C. V., Hughes, G., Porteus, W. K., Ledgerwood, E. C., Smith, R. A. J., and Murphy, M. P., 2001, *J Biol Chem* 276, 4588.
[b]Smith, R. A. J., Porteous, C. M., Coulter, C. V., and Murphy, M. P. 1999 *Eur J Biochem* 263, 709.
[c]Smith, R. A. J., Porteous, C. M., Gane, A. M., and Murphy, M. P. 2003 *Proc Nat Acad Sci* 100, 9, 5407.

Figure 3:
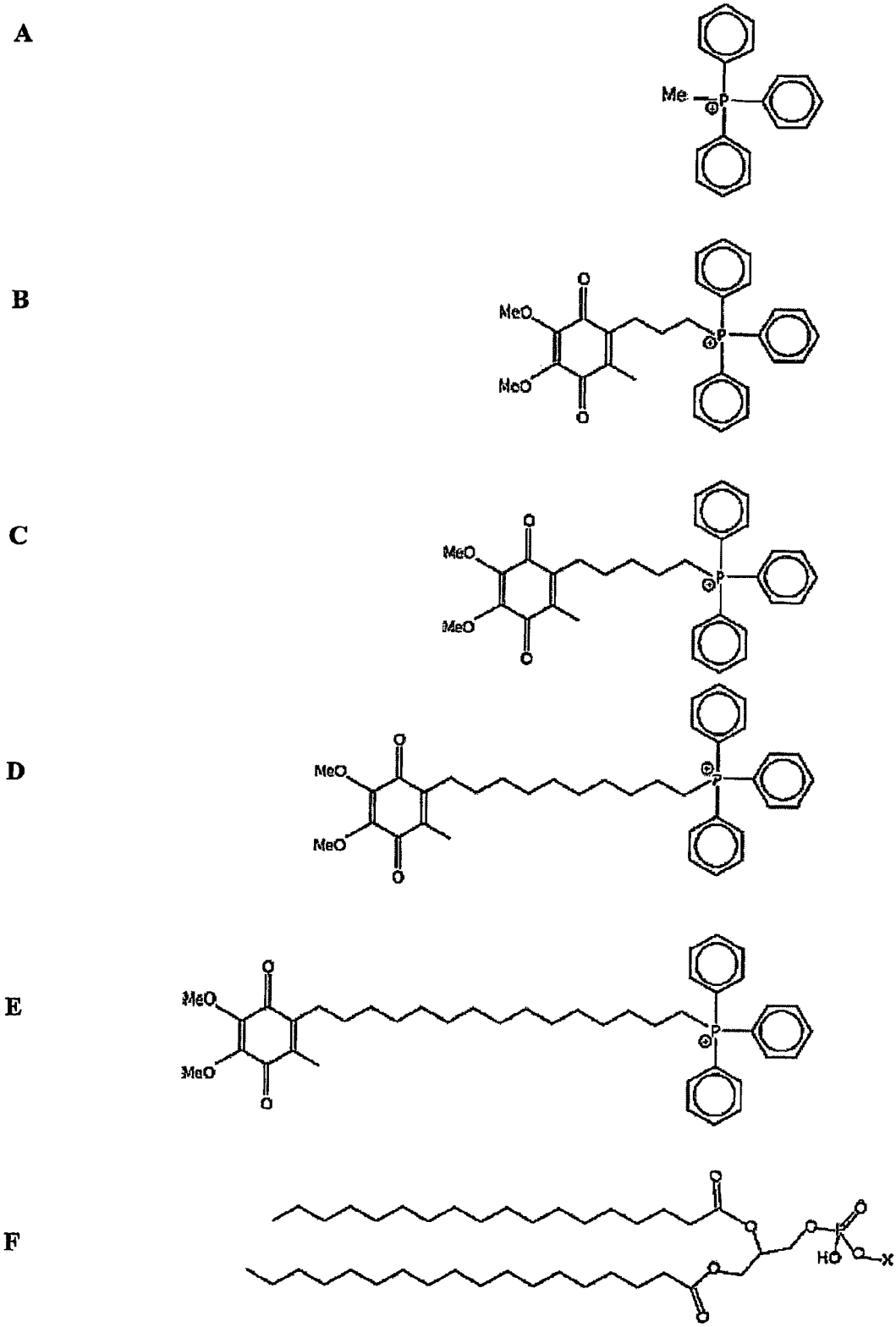
FIG. 3 depicts the structure of Mitoquinone antioxidant compounds and the related compound TPMP. A phospholipid drawn to the same scale is aligned with the Mitoquinone antioxidant compounds to indicate potential maximum depths of penetration of the ubiquinol side chain into one leaflet of a phospholipid bilayer. A: TPMP. B: Mitoquinone-C3. C: Mitoquinone-C5. D: Mitoquininone-C10. E: Mitoquinone-C15. F: phospholipid.

From their octan-1-ol/PBS partition coefficients it is clear that Mitoquinone-C3, Mitoquinone-C5, Mitoquinone-C10 and Mitoquinone-C15 span a wide range of hydrophobicities. That of Mitoquinone-C3 is similar to the simple, relatively water soluble TPMP cation, while that of Mitoquinone-C15 indicates that it has very low water solubility. Alkyltriphenylphosphonium cations such as Mitoquinone are reported to adsorb onto phospholipid bilayers with the cation at the level of the carboxylic acid groups while the hydrophobic alkyl group penetrates into the hydrophobic core of the membrane. It is believed that the longer the methylene bridge the deeper the antioxidant ubiquinol will penetrate into the hydrophobic core of membrane. The maximum extent to which penetration into one leaflet of the membrane we believe will occur for these compounds is illustrated in FIG. 3, which shows the Mitoquinone variants aligned with a typical phospholipid. This modelling indicates that the ubiquinol moiety of Mitoquinone-C3 only penetrates close to the membrane surface while those of Mitoquinone-C10 and Mitoquinone-C15 penetrate close to the core of the phospholipid bilayer.

We have synthesised a series of antioxidant compounds with a range of hydrophobicities and depths of penetration into the phospholipid bilayer.

Example 4

Mitochondrial Uptake of Mitochondrially Targeted Compounds

To demonstrate that mitochondrial targeting is effective, the uptake by mitochondria in response to the membrane potential of exemplary antioxidant compounds Mitoquinone-C3, Mitoquinone-C5, Mitoquinone-C10, and Mitoquinone-C15 was determined.

To measure the uptake of antioxidant compounds by energised mitochondria, an ion-selective electrode was constructed (Smith, R. A., Kelso, G. F., James, A. M. and Murphy, M. P. (2004) Meth. Enzymol. 382, 45-67; Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The electrode and a Ag/AgCl reference electrode were inserted through the air-tight Perspex lid of a stirred and thermostatted 3 ml incubation chamber at 30° C., provided with an injection port for the addition of substrates. To measure antioxidant compound uptake, rat liver mitochondria (1 mg protein/ml) were incubated at 30° C. in KCl medium (120 mM KCl, 10 mM HEPES, pH 7.2, 1 mM EGTA) and nigericin (1 μg/ml) and rotenone (8 μg/ml). Succinate (10 mM) and FCCP (500 nM) were added where indicated. The output from the ion-selective electrode was passed to a PowerLab Data acquisition system via a front-end pH amplifier and analysed using Chart software, all from ADInstruments.

Rat liver mitochondria were prepared by homogenisation followed by differential centrifugation in ice-cold buffer containing 250 mM sucrose, 5 mM Tris-HCl, 1 mM EGTA, pH 7.4 (Chappell, J. B. and Hansford, R. G. (1972) in: Subcellular components: preparation and fractionation, pp. 77-91 (Birnie, G. D., Ed.) Butterworths, London). The protein concentration was determined by the biuret assay using BSA as a standard (Gornall, A. G., Bardawill, C. J. and David, M. M. (1949) J. Biol. Chem. 177, 751-766). Mitochondrial membrane potential was measured by adding 500 nM TPMP supplemented with 50 nCi [$^3$H]TPMP to mitochondria suspended in KCl medium (120 mM KCl, 10 mM HEPES, pH 7.2, 1 mM EGTA) at 25° C. (Brand, M. D. (1995) in: Bioenergetics—a practical approach, pp. 39-62 (Brown, G. C. and Cooper, C. E., Eds.) IRL, Oxford). After incubation, the mitochondria were pelleted by centrifugation and the amounts of [$^3$H]TPMP in the supernatant and pellets were quantitated by scintillation counting and the membrane potential calculated assuming a mitochondrial volume of 0.5 μl/mg mitochondrial protein and a TPMP binding correction of 0.4 (Brown, G. C. and Brand, M. D. (1985) Biochem. J. 225, 399-405).

We constructed ion-selective electrodes to measure their steady-state concentrations (Smith, R. A., Kelso, G. F., James, A. M. and Murphy, M. P. (2004) Meth. Enzymol. 382, 45-67; Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The response of these electrodes to simple triphenylphosphonium cations such as TPMP is Nernstian, with a linear response of electrode voltage to $\log_{10}$-[cation concentration] and a slope of ~60 mV at 30° C. (Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The most hydrophilic compound, Mitoquinone-C3, also gave a Nernstian electrode response with a slope close to 60 mV at concentrations above 10 μM. This is illustrated in FIG. 4A, right hand side, by the logarithmic electrode response to sequential additions of 1 μM Mitoquinone-C3 in the absence of mitochondria. For Mitoquinone-C5, Mitoquinone-C10 and Mitoquinone-C15 the electrode also responded rapidly and stably to sequential additions in the absence of mitochondria (FIGS. 4B, 4C, and 4D, respectively, right hand side panels). However in these cases the electrode responses were not Nernstian, we believe due to the greater hydrophobicity of these compounds. Even so, for all four antioxidant compounds the ion-selective electrode enabled the measurement of the free concentrations of the compounds and thus their uptake by mitochondria in real time.

Figure 4:
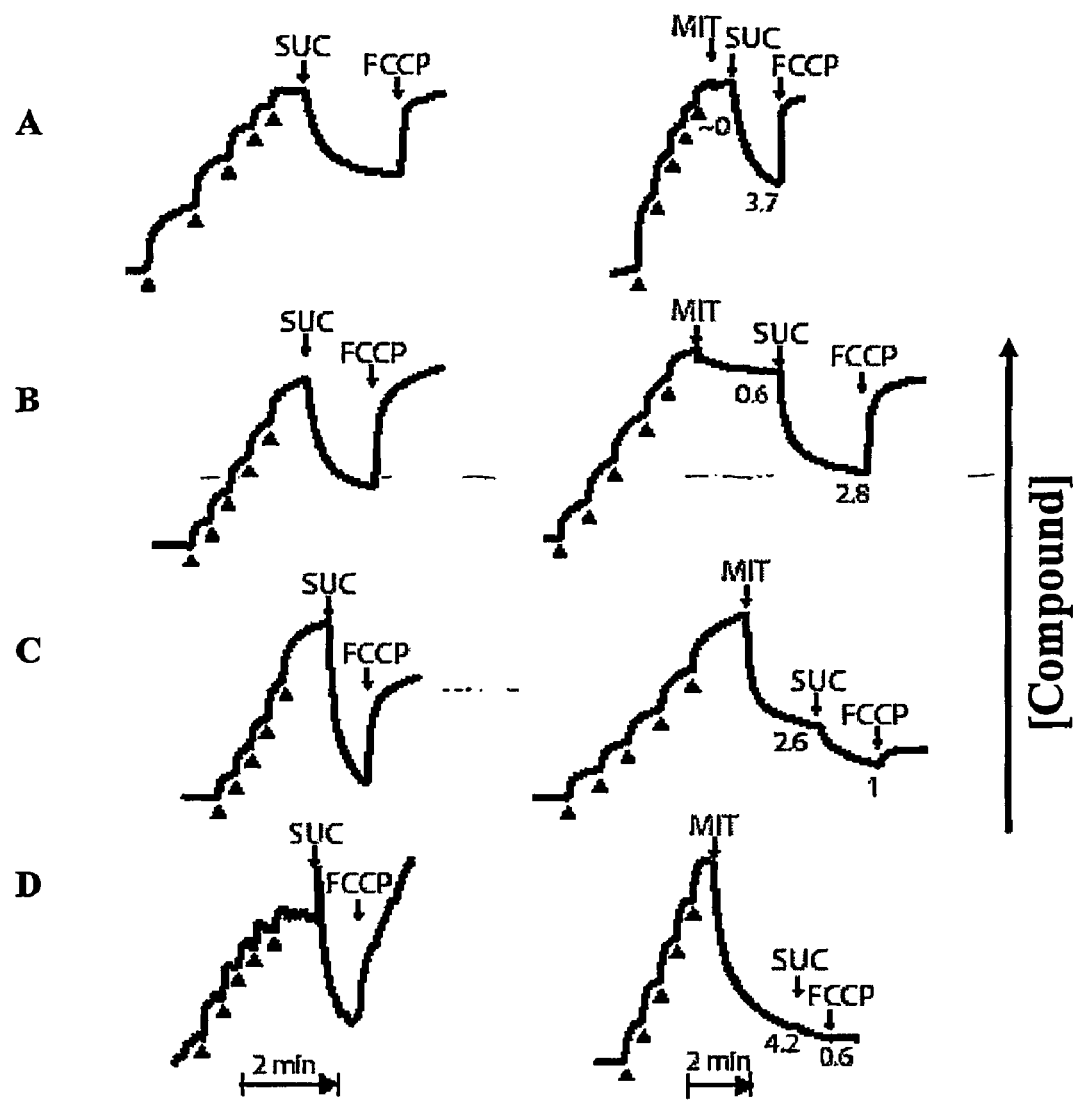
FIG. 4 presents graphs showing the uptake and binding of antioxidant compounds by mitochondria measured using an ion selective electrode. A: Mitoquinone-C3. B: Mitoquinone-C5. C: Mitoquinone-C10. D: Mitoquinone-C15. In the left hand panels mitochondria (1 mg protein/ml) in the presence of rotenone were present and then the antioxidant compounds were added as five sequential 1 μM additions (black arrowheads) to calibrate the electrode response. For the right hand panels the electrodes were first calibrated by five sequential 1 μM additions (black arrowheads) and mitochondria (1 mg protein/ml) were then added. In all cases succinate was added to generate a membrane potential, and FCCP was added to dissipate it. Data are typical traces of experiments repeated at least 2-3 times.

To measure antioxidant compound uptake, mitochondria were added to the electrode chamber in the presence of rotenone to prevent formation of a membrane potential (left side of FIG. 4). We then made five sequential 1 μM additions of antioxidant compound to calibrate the electrode response, followed by the respiratory substrate succinate to generate a membrane potential. Mitochondrial energisation led to the rapid uptake of all the antioxidant compound variants by the mitochondria, and subsequent addition of the uncoupler FCCP abolished the membrane potential and led to their rapid release from the mitochondria (FIG. 4A-D, left side). These experiments clearly show mitochondrial membrane potential-dependent uptake of Mitoquinone-C3, Mitoquinone-C5, and Mitoquinone-C10. While Mitoquinone-C15 was also taken up by mitochondria on induction of a membrane potential, the electrode response to Mitoquinone-C15 in the presence of mitochondria was weaker, noisier and more prone to drift. This contrasts with the electrode response to Mitoquinone-C15 in the absence of mitochondria (cf. right hand panels), and is due to its low free concentrations in the presence of mitochondria.

The extent of antioxidant compound binding to deenergised mitochondria was then determined (FIG. 4, right hand side). For these experiments the antioxidant compound variants were first added to the electrode chamber and then mitochondria were added in the presence of rotenone to prevent formation of a membrane potential. The decrease in antioxidant compound concentration on adding mitochondria is due to binding of antioxidant compound to the deenergised mitochondria. The subsequent addition of succinate to generate a membrane potential indicates the membrane potential dependent uptake of the compounds, which is then reversed by addition of FCCP to abolish the membrane potential.

The free concentration of Mitoquinone-C3 was unaffected by addition of mitochondria, indicating that negligible amounts of Mitoquinone-C3 bound to deenergised mitochondria (FIG. 4A, right hand side). The FCCP-sensitive uptake of mitoquinone-C3 on energisation with succinate was about 3.7 nmol mitoquinone-C3/mg protein, corresponding to an accumulation ratio of ~2×10$^3$. This is consistent with that expected from the Nernst equation and a mitochondrial membrane potential of about 180 mV, allowing for corrections for intramitochondrial binding.

For Mitoquinone-C5 there was some binding of the compound to the deenergised mitochondria (~0.6 nmol/mg protein), however this was negligible compared to its subsequent uptake on energisation with succinate, of about 2.8 nmol Mitoquinone-C57 μm protein, corresponding to an accumulation ratio of about 1.4×10$^3$ (FIG. 4B, right hand side).

For Mitoquinone-C10 there was significant binding to deenergised mitochondria of about 2.6 mmol Mitoquinone- C10, and this was followed by further uptake of about 1 nmol/mg protein on addition of succinate (FIG. 4C, right hand side).

Nearly all of the free Mitoquinone-C15 was bound to the deenergised mitochondria, but there was some further uptake on energisation with succinate. The membrane potential-dependent uptake of Mitoquinone-C15 was clear on the left hand panel of FIG. 4D, where the electrode response was highly sensitive to enable measurement of the small amount of free Mitoquinone-C15 when the electrode was calibrated in the presence of mitochondria. In contrast, the uptake of Mitoquinone-C15 is difficult to see on the right hand side of FIG. 4D, where the electrode response was far less sensitive to enable measurement of Mitoquinone-C15 in the absence of mitochondria.

These experiments show that the length of the methylene bridges of the antioxidant compounds at least in part determines their extents of adsorption to mitochondrial membranes (right hand side of FIG. 4). The adsorption ranges from negligible for Mitoquinone-C3, to almost complete binding for Mitoquinone-C15. On addition of Mitoquinone-C15 to deenergised mitochondria essentially all the compound binds, distributed across both surfaces of the inner and outer membranes. When a membrane potential is induced we believe there will be significant redistribution of the compound to the matrix-facing surface of the inner membrane from the outer surface of the inner membrane and from the outer membrane. In summary, all the antioxidant compound variants are taken up into mitochondria driven by the membrane potential, and the longer the methylene bridge the greater their adsorption to phospholipid bilayers.

Example 5

Antioxidant Efficacy of Exemplary Mitochondrially Targeted Compounds

Figure 5:
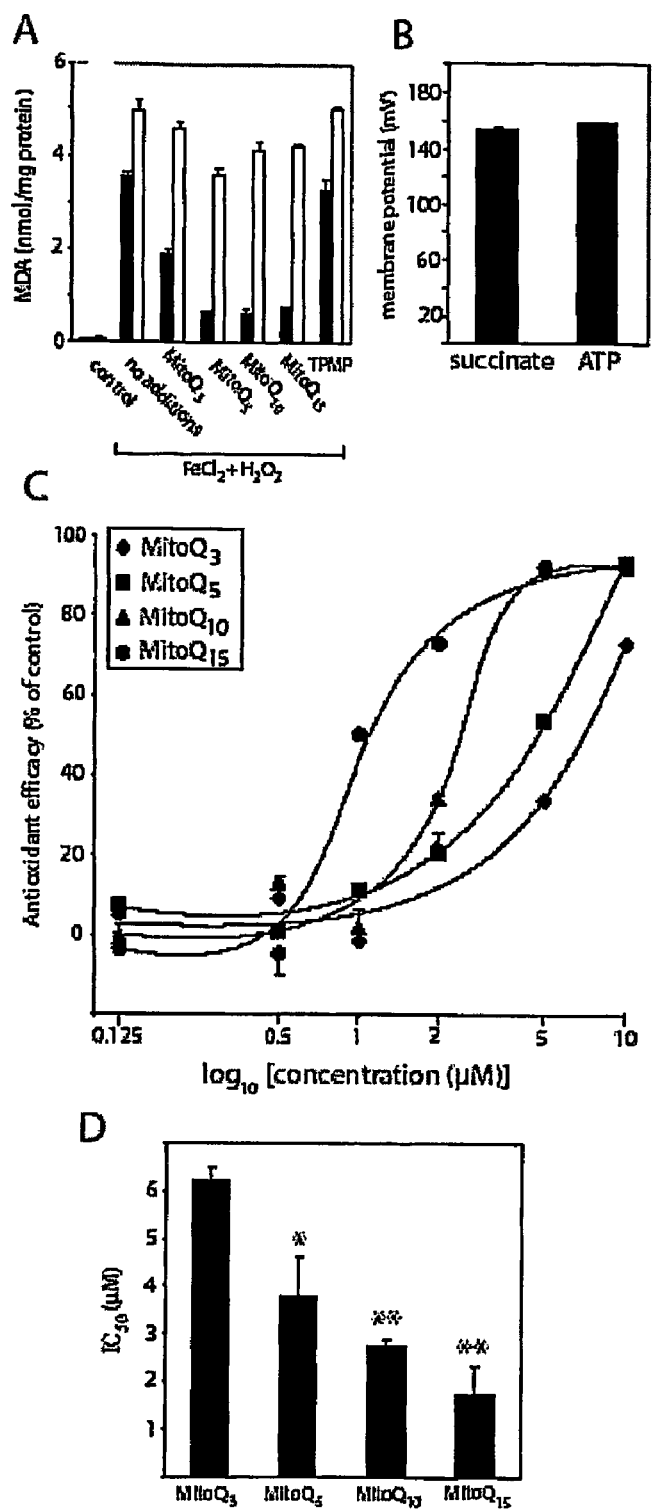
FIG. 5 presents graphs showing the antioxidant efficacy of antioxidant compounds. A: Mitochondria were energised with succinate (black bars) or by incubation with an ATP regenerating system consisting of ATP, phosphoenol pyruvate and pyruvate kinase (white bars). After a 30 sec preincubation with the various Mitoquinone analogues, TPMP or carrier, oxidative stress was induced by addition of 50 μM $FeCl_2$ and 300 µM $H_2O_2$. After 15 min incubation at 37° C., lipid peroxidation was estimated by measuring TBARs. Data are means±range of two independent experiments. The slight protective effect of Mitoquinone-C5 on lipid peroxidation in the presence of ATP is due to some of the Mitoquinone-C5 added from the stock solution being in the ubiquinol form. B: The mitochondrial membrane potential induced with succinate or with the ATP regenerating system was measured from the accumulation of [$^3$H]TPMP. Data are means±range of duplicate determinations of a 25 minute incubation. The membrane potentials after a 5 minute incubation were the same (data not shown). C: The concentration dependence of the prevention of the accumulation of TBARs by the antioxidant compounds was measured. All incubations were carried out in the presence of succinate as described for A. Results are expressed as % inhibition of TBARS formation, taking the value of a sample exposed to $FeCl_2/H_2O_2$ in the absence of Mitoquinone analogues as 0% inhibition, and a control sample (no $FeCl_2/H_2O_2$ added) as 100%. The data shown are a typical titration with each concentration determined in triplicate±SD. D: The $IC_{50}$ concentrations for prevention of lipid peroxidation. Data are means±sem, estimated from three independent titrations as shown in C. The statistical significance relative to the $IC_{50}$ for Mitoquinone-C3 was determined using Student's two tailed t test: *$p<0.05$; **$p<0.005$.

The compounds of the invention are also highly effective against oxidative stress. To measure antioxidant efficacy, the ability of the antioxidant compounds to prevent lipid peroxidation in mitochondria, measured from the accumulation of TBARS in mitochondria exposed to ferrous iron and hydrogen peroxide (FIG. 5).

To quantitate lipid peroxidation, the TBARS assay was used. Rat liver mitochondria (2 mg protein/ml) were incubated in 0.8 ml medium containing 100 mM KCl, 10 mM Tris-HCl, pH 7.6 at 37° C., supplemented with either 10 mM succinate and 8 mg/ml rotenone, or an ATP regenerating system of 2.5 mM ATP, 1 mM phosphoenolpyruvate and 4 U/ml pyruvate kinase. The mitochondria were then exposed to oxidative stress by addition of 50 mM $FeCl_2$/300 mM $H_2O_2$ for 15 min at 37° C. After the incubation, 64 ml 2% (w/v) butylated hydroxytoluene in ethanol was added, followed by 200 ml 35% (v/v) $HClO_4$ and 200 ml 1% (w/v) thiobarbituric acid. Samples were then incubated for 15 min at 100° C., centrifuged (5 min at 12,000×g) and the supernatant transferred to a glass tube. After addition of 3 ml water and 3 ml butan-1-ol, samples were vortexed, and the two phases allowed to separate. 200 ml aliquots of the organic layer were then analysed in a fluorometric plate reader ($\lambda_{Ex}$=515 nm; $\lambda_{Em}$=553 nm) for thiobarbituric acid reactive species (TBARS) and compared with a malondialdehyde (MDA) standard curve prepared from 0.01-5 mM 1,1,3,3-tetraethoxypropane (Kelso, G. F., Porteous, C. M., Coulter, C. V., Hughes, G., Porteous, W. K., Ledgerwood, E. C., Smith, R. A. J. and Murphy, M. P. (2001) J. Biol. Chem. 276, 4588-4596).

For mitochondria energised with succinate, the background level of TBARS was negligible, but it increased to about 3.75 nmol MDA/mg protein on exposure to oxidative stress (FIG. 5A; filled bars). High concentrations (5 μM) of any of the antioxidant compounds largely prevented the accumulation of TBARS, while the simple cation TPMP did not. This confirms that it was the ubiquinol side chain of the Mitoquinone antioxidant compounds that was responsible for the antioxidant action, and not any non-specific interactions of the cation with mitochondria.

In these experiments, succinate will both maintain a membrane potential to drive the uptake of the cations into mitochondria, and also recycle the ubiquinone form of the Mitoquinone antioxidant compounds to the active antioxidant ubiquinol form (Kelso, G. F., Porteous, C. M., Coulter, C. V., Hughes, G., Porteous, W. K., Ledgerwood, E. C., Smith, R. A. J. and Murphy, M. P. (2001) J. Biol. Chem. 276, 4588-4596). To see if reduction by the respiratory chain was required for the antioxidant efficacy of the Mitoquinone antioxidant compounds, we incubated mitochondria in the presence of ATP and an ATP regenerating system. ATP hydrolysis and reversal of the mitochondrial ATP synthase led to extensive proton pumping which built up a membrane potential similar to that generated by succinate (FIG. 5B). This will lead to the same Mitoquinone antioxidant compound uptake as for mitochondria energised by succinate, but now the Mitoquinone antioxidant compounds will no longer be recycled to their active ubiquinol forms by the respiratory chain. The Mitoquinone antioxidant compounds were ineffective at preventing lipid peroxidation in mitochondria energised by ATP hydrolysis (FIG. 5a, white bars), compared with the dramatic protection seen in mitochondria energised by succinate (FIG. 5b, black bars). Therefore reduction of Mitoquinone antioxidant compounds by the respiratory chain, as well as accumulation by the mitochondrial membrane potential are required for the antioxidant efficacy of the Mitoquinone antioxidant compounds.

Lower levels of lipid peroxidation were observed in the control samples of mitochondria energised with succinate, compared to those energised with ATP (FIG. 5A). This is due to the protective antioxidant effect of the endogenous mitochondrial Coenzyme Q pool which is held reduced by in the presence of succinate but oxidised in the presence of ATP (James, A. M., Smith, R. A. and Murphy, M. P. (2004) Arch. Biochem. Biophys. 423, 47-56; Ernster, L., Forsmark, P. and Nordenbrand, K. (1992) Biofactors 3, 241-8). In summary, all the Mitoquinone antioxidant compounds require activation by the respiratory chain to be effective antioxidants.

For FIG. 5A a single concentration of 5 μM was used for all the Mitoquinone antioxidant compounds. To compare their relative antioxidant efficacies we titrated the compounds in the presence of succinate: a typical titration is shown in FIG. 5C. This experiment suggests that the antioxidant efficacy of these compounds correlates with the length of the methylene bridge. To quantitate this we calculated the $IC_{50}$ values for the prevention of lipid peroxidation by the four exemplary Mitoquinone antioxidant compounds (FIG. 4D). These measurements confirmed that the order of antioxidant efficacy was: Mitoquinone-C15>Mitoquinone-C10>Mitoquinone-C5>Mitoquinone-C3.

All the Mitoquinone antioxidant compounds were accumulated into mitochondria driven by the mitochondrial membrane potential. For the most hydrophobic compound, Mitoquinone-C15, this effect was largely masked by extensive binding to phospholipid bilayers. All of the compounds were effective antioxidants and for persistent antioxidant activity over 15 minutes all required the action of the respiratory chain to recycle the Mitoquinone antioxidant compound to its active antioxidant form after having detoxified lipid peroxidation intermediates.

Example 6

Effect of Mitochondrially Targeted Antioxidant Compounds on Cardiac Haemodynamics and Mitochondrial Function The effect of administration of mitochondrially targeted antioxidant compounds, in particular Mitoquinone-C10 and Mitoquinone-C3, on cardiac function was assessed using the Langendorf isolated heart perfusion model. Rats were assigned to the following four administration groups: Control placebo), TPMP (methyltriphenyl phosphonium), Mitoquinone-C10, and Mitoquinone-C3. Following the treatment period, rats were humanely sacrificed and the isolated hearts were connected to the Langendorf isolated perfusion system. This system uses retro-perfusion through the aorta to maintain the heart while cardiac function is measured. Left ventricular pressure was measured with a left ventricular balloon. Coronary flow was also measured.

Figure 6:
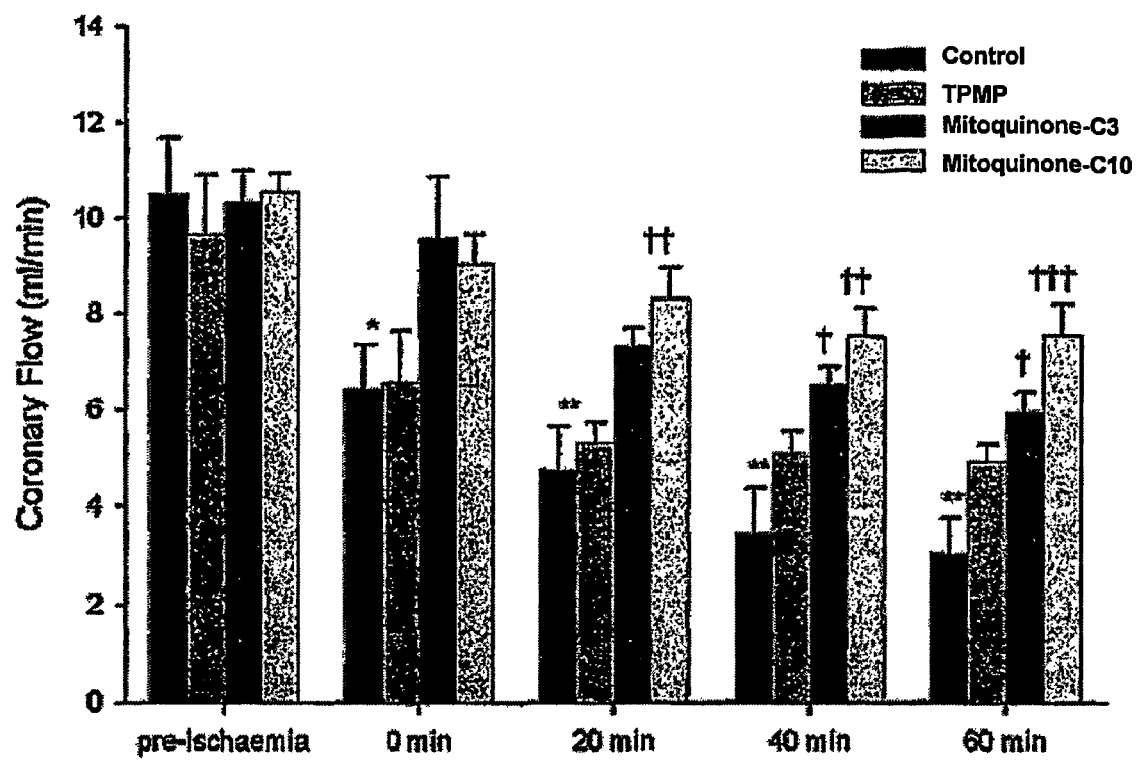
FIG. 6 presents a graph showing the effect of Mitoquinone-C10 and Mitoquinone-C3 on sinus coronary flow.

FIG. 6 depicts the coronary flow at 10 mmHg left ventricular pressure for each of the treatment groups. Coronary flow was measured pre-ischaemia and again at zero minutes, 20 minutes, 40 minutes and 60 minutes following induction of ischaemia. A one way ANOVA with bonferroni post hoc test was performed. Significance versus pre-ischaemic control: * $P<0.05$;  $P<0.01$; * $P<0.001$. Significance versus respective time control: † $P<0.05$; † $P<0.01$; ††† $P<0.001$.

The results show that treatment with Mitoquinone-C10 significantly reduces the ischaemia-induced reduction in coronary flow. Mitoquinone-C3 has a lesser but still significant effect at the later time points. The absence of any effect with administration of TPMP indicate that it is the antioxidant moiety of Mitoquinone-C10 and Mitoquinone-C3, and not the triphenylphosphonium cation, that is responsible for the effects observed with the mitochondrially targeted antioxidant compounds.

Figure 7:
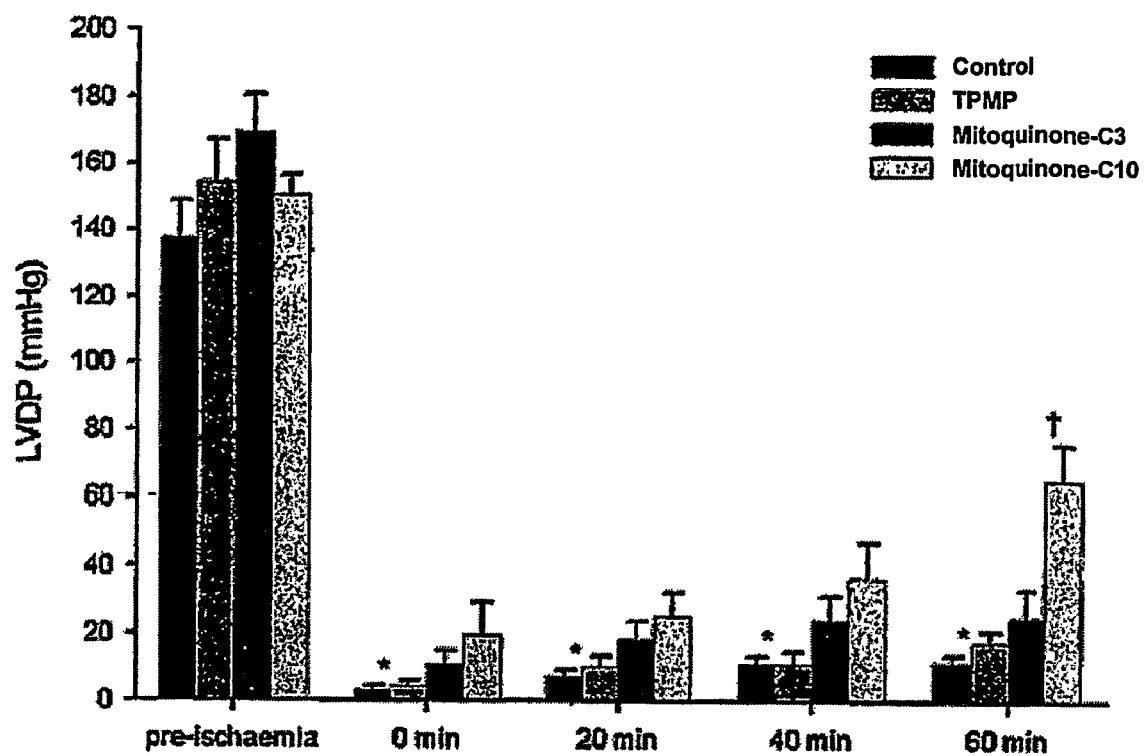
FIG. 7 presents a graph showing the effect of Mitoquinone-C10 and Mitoquinone-C3 on left ventricular diastolic pressure.

FIG. 7 depicts the effects of treatment on left ventricular diastolic pressure at 10 mmHg. Left ventricular diastolic pressure was measured prior to induction of ischaemia and again at zero minutes, 20 minutes, 40 minutes and 60 minutes following the induction of ischaemia. Statistical analysis was an ANOVA on ranks with Dunns post hoc test. Significance verses pre-ischaemic control: * $P<0.05$. † represents $P<0.05$ versus 60 min post ischaemic control. The results show that treatment with Mitoquinone-C10 results in a statistically significant increase in left ventricular diastolic pressure verses untreated rats, reducing the ischaemia-induced reduction in left ventricular diastolic pressure. The absence of any effect with administration of TPMP indicate that it is the antioxidant moiety of Mitoquinone-C10, and not the triphenylphosphonium cation, that is responsible for the effects observed with the mitochondrially targeted antioxidant compounds.

Figure 8:
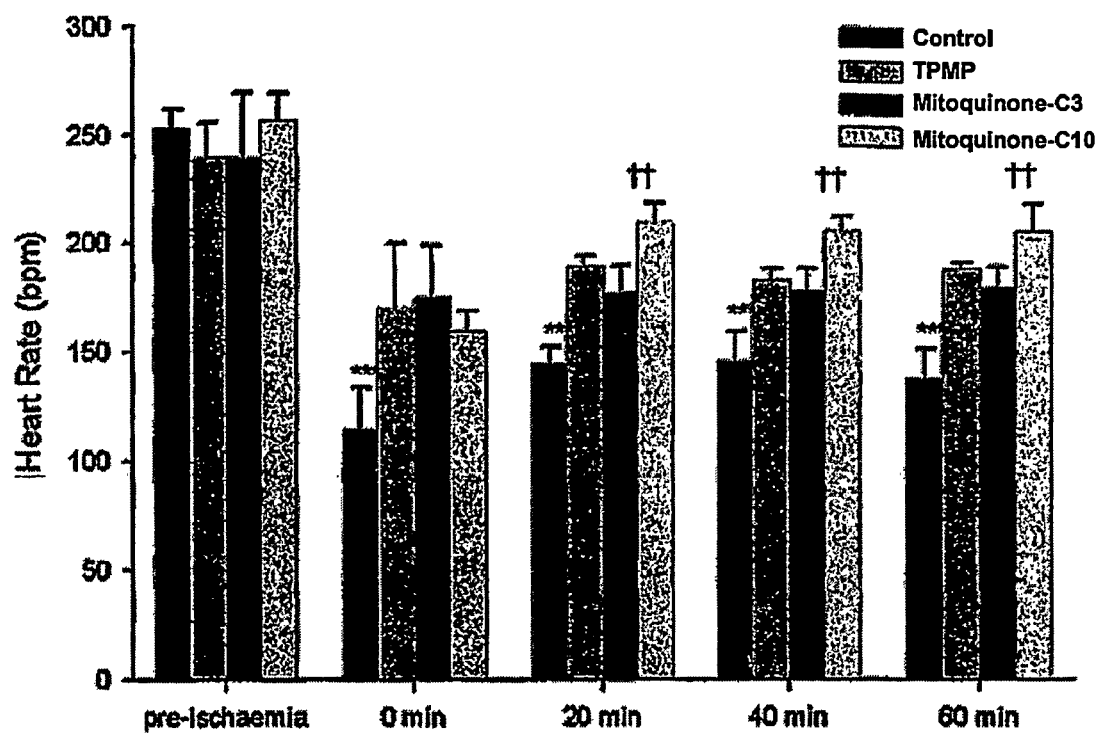
FIG. 8 present a graph which shows the effect of Mitoquinone-C10 and Mitoquinone-C3 on heart rate.

The effect of administration of Mitoquinone-C10 and Mitoquinone-C3 on heart rate was then determined. FIG. 8 depicts the heart rate for each of the treatment groups pre-ischaemia, and zero minutes, 20 minutes, 40 minutes and 60 minutes following the induction of ischaemia. Results shown are one way ANOVA followed by bonferroni post hoc test. *** represents $P<0.001$ versus pre-ischaemic control. † represents $P<0.05$ versus respective post ischaemic control. The results show that treatment with Mitoquinone-C10 significantly reduces the ischaemia induced reduction in heart rate compared to control rats. The absence of any effect with administration of TPMP indicate that it is the antioxidant moiety of Mitoquinone-C10, and not the triphenylphosphonium cation, that is responsible for the effects observed with the mitochondrially targeted antioxidant compounds.

Figure 9:
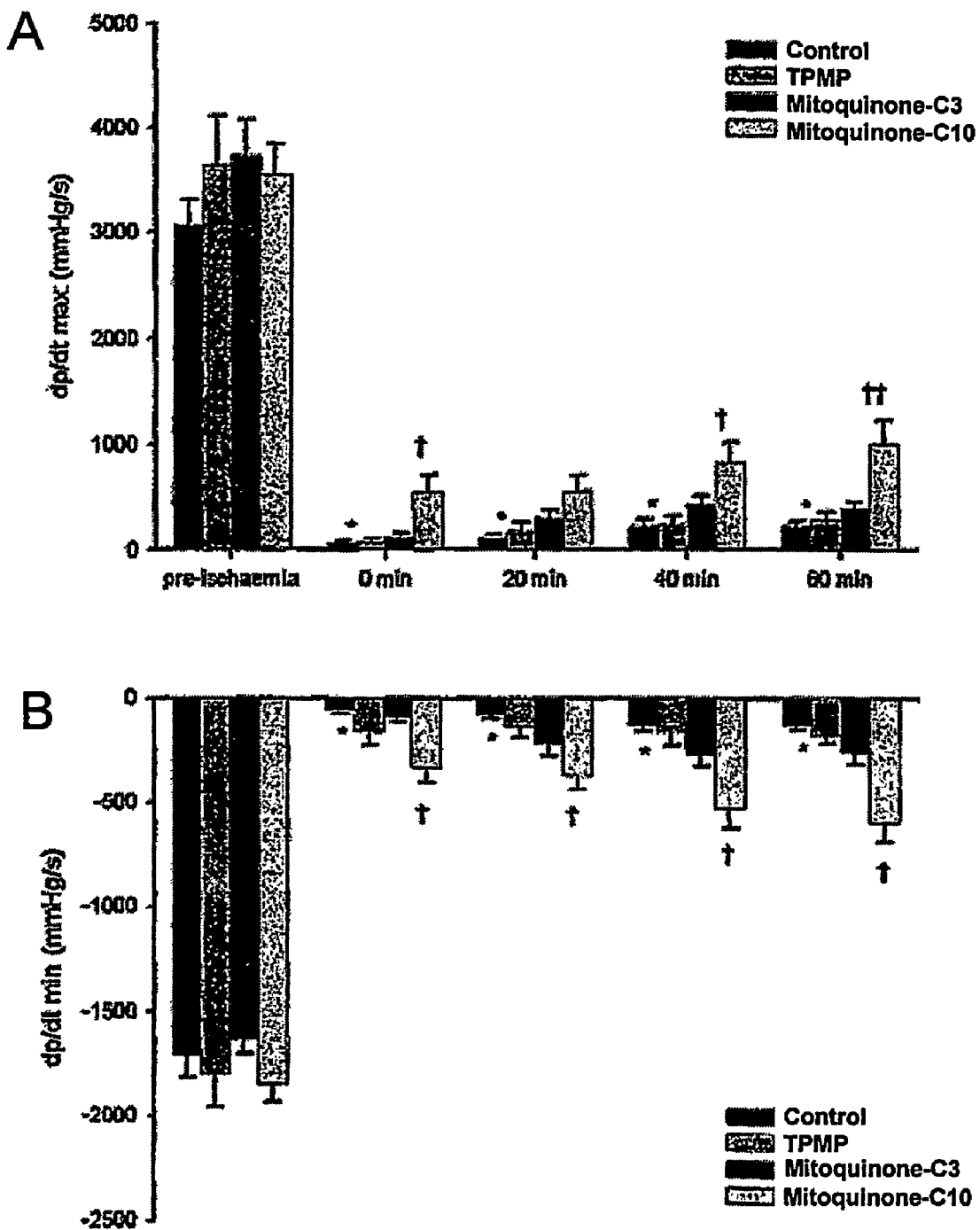
FIG. 9 presents graphs showing the rate of left ventricular change.

Cardiac function was further assessed by determining the effect of administration of mitochondrially targeted antioxidant compounds on the rate of contraction and relaxation of the heart. FIG. 9A depicts the rate of contraction in each of the four treatment groups pre-ischaemia, and zero minutes, 20 minutes, 40 minutes and 60 minutes following induction of ischaemia. FIG. 9B depicts the rate of relaxation in each of the four treatment groups pre-ischaemia, and zero minutes, 20 minutes, 40 minutes and 60 minutes following induction of ischaemia. In each case ANOVA was performed on ranks with Dunns post hoc test performed. * represents significance with $P<0.05$ verses pre-ischaemia control. † represents significance with $P<0.05$ versus respective post ischaemic time controls. †\ represents significance with $P<0.01$ versus respective post ischaemic time control.

The results show that administration of Mitoquinone-C10 has a statistically significant effect, reducing the ischaemia-induced reduction in the rate of contraction and relaxation of the left ventricle when compared to control rats.

Figure 10:
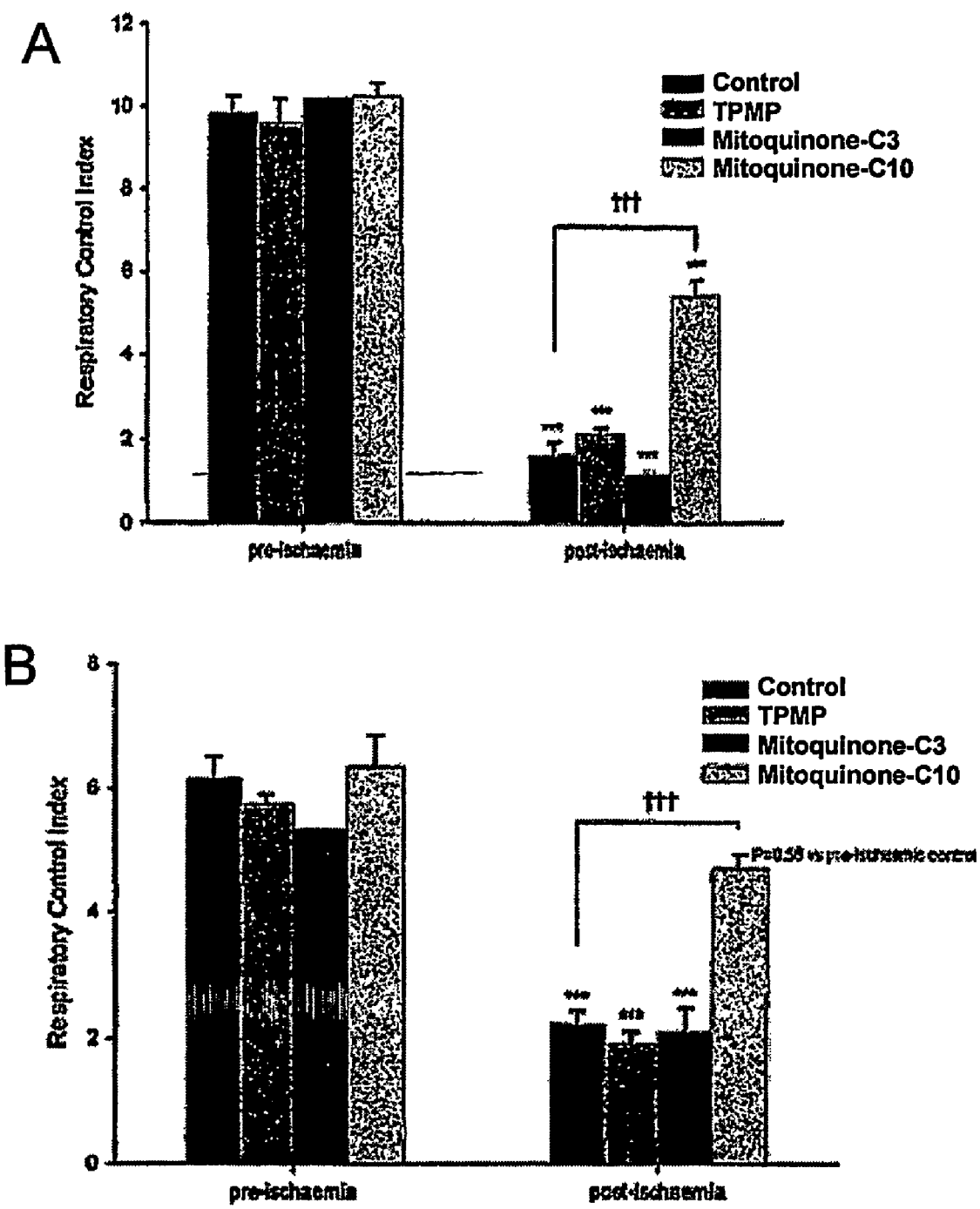
FIG. 10 depicts graphs showing the effect of Mitoquinone-C10 and Mitoquinone-C3 on post ischaemia mitochondrial respiratory function.

The above data clearly show the beneficial effect of administration of mitochondrially targeted antioxidant compounds on cardiac function. In order to determine whether the observed effects on cardiac function were due to the effect of the mitochondrial targeted antioxidant compound on mitochondrial function, mitochondrial activity pre-ischaemia and post-ischaemia was assessed for each of the treatment groups. FIG. 10A depicts NAD$^+$ linked respiratory function of mitochondria pre and post-ischaemia for each of the four treatment groups. FIG. 10B presents FAD linked respiratory function pre and post-ischaemia for each of the four treatment groups. *** represents significance with $P<0.001$ versus pre-ischaemic control. ††† represents significance with $P<0.001$ versus post ischaemic control.

These data show that Mitoquinone-C10 has a statistically significant beneficial effect on mitochondrially respiratory function following ischaemia compared to control rats. These results support the conclusion that the effects of administration of mitochondrially targeted antioxidant compounds on cardiac function is due to a protective effect on mitochondrial function.

Example 7

Stability of Mitoquinone-C10 Complexes with β-Cyclodextrin

In preformulation studies Mitoquinone-C10 as the bromide salt was found to degrade over time in the solid state when stored at 25° C., 50% RH and 40° C., 75% RH. The objective of the present study was to establish whether the solid state stability of Mitoquinone-C10 could be improved by complexing with β-cyclodextrin.

Mitoquinone-C10 batch no. 6 and idebenone were supplied by Industrial Research Limited (New Zealand). β-cyclodextrin (lot no. 70P225) was purchased from ISP technologies Inc. NaCl, NaH PU and methanol (HPLC) were purchased from BDH.

Solid State Stability Study of Pure Mitoquinone-C10

Samples of Mitoquinone-C10 (approximately 5 mg) were accurately weighed into clear bottles and exposed to 25° C., 50% RH, 40° C., 75% RH and 4° C. over silica. The bottles were removed after 1, 2, 4, 8, 16, 32 and 64 days and analysed for Mitoquinone-C10 by a validated HPLC method using Mitoquinone-C10 stored at −20° C. over silica as control.

Preparation of Mitoquinone-C10: β-Cyclodextrin Complexes

Three complexes with different molar ratios (Mitoquinone-C10 bromide: β-cyclodextrin 1:1, 1:2 and 1:4) were prepared using Mitoquinone-C10 batch no. 6.

Preparation of β-Cyclodextrin Solution in Water

β-cyclodextrin (1.1397 g, equal to 1.0361 g after correction for moisture content) was accurately weighed and dissolved in double distilled water by sonicating for 10 min. The volume was made up to 100 ml with water.

Preparation of Mitoquinone-C10: β-Cyclodextrin (1:1 Molar Ratio) Complex

An ethanolic solution of Mitoquinone-C10 bromide (90 mg equal to 59.95 mg of Mitoquinone-C10) was evaporated under nitrogen on a hot plate maintained at 40-50° C. for 8 min. β-cyclodextrin solution (10 ml) and double distilled water (30 ml) were added to the beaker which was then sonicated for 40 min.

Preparation of Mitoquinone-C10: β-Cyclodextrin (1:2 Molar Ratio) Complex

An ethanolic solution of Mitoquinone-C10 bromide (89.8 mg equal to 59.82 mg of Mitoquinone-C10) was evaporated under nitrogen on a hot plate maintained at 37-45° C. for 10 min followed by 3 min at 50° C. β-cyclodextrin solution (20 ml) and double distilled water (20 ml) were added to the beaker which was then sonicated for 30 min.

Preparation of Mitoquinone-C10: β-Cyclodextrin (1:4 Molar Ratio) Complex

An ethanolic solution of Mitoquinone-C10 bromide (90 mg equal to 59.95 mg of Mitoquinone-C10) was evaporated under nitrogen on a hot plate maintained at 37-50° C. for 12 min. β-cyclodextrin solution (40 ml) was added to the beaker which was then sonicated for 20 min.

All the above solutions were frozen by storing at −18° C. overnight. The frozen solutions were freeze-dried for 2 days using the LABCONO freeze drier. The lyophilized compounds were stored at −20° C.

Differential Scanning Calorimetry of the Freeze-Dried Mitoquinone-C10: β-Cyclodextrin Complexes Differential scanning calorimetry (DSC) of the three freeze-dried complexes was carried out using a Perkin Elmer Differential Scanning Calorimeter PYRIS-1. A Mitoquinone-C10 sample was prepared by evaporating an ethanolic solution under nitrogen gas at 35-50° C. for 10 min.

Aluminium pans (No. 0219-0041, supplied by Perkin-Elmer) were used. The analysis was carried out under nitrogen purge. Empty pans were used to set the baseline.

Scanning temperature range was 50-160° C. with an initial hold at 50° C. for 1 min followed by an increase of 10° C./min up to 160° C.

HPLC Assay

An HPLC method for Mitoquinone-C10 was developed using methanol and 0.01M sodium dihydrogen phosphate (85:15) as mobile phase at a flow rate of 1 ml/min and using UV-VIS detection at 265 μm. The internal standard was idebenone. The column was Prodigy ODS3100A (Phenomenex) with particle size 5μ. Later this method was modified after the arrival of a new column. The mobile phase used in the modified method was methanol and 0.01M sodium dihydrogen phosphate (80:20). This method was validated. Interference by β-cyclodextrin in the HPLC method was checked before analysing the Mitoquinone-C10: β-cyclodextrin complexes. It was shown that β-cyclodextrin does not interfere in the Mitoquinone-C10 HPLC assay.

Stability Study of Mitoquinone-C10: β-Cyclodextrin Complexes

As there were three complexes of Mitoquinone-C10 with β-cyclodextrin, the amount of Mitoquinone-C10 in 5 mg samples from the different complexes was different. In order to expose equal amounts of Mitoquinone-C10 in all three complexes, different weights of complexes were taken: 4 mg of 1:1 complex containing 1.473 mg of Mitoquinone-C10; 6.5 mg of 1:2 complex containing 1.469 mg of Mitoquinone-C10; and 11.5 mg of 1:4 complex containing 1.467 mg of Mitoquinone-C10 were taken and used in the stability study as per the Standard Operating Procedure.

Aliquots of HPLC water (1.5 ml) were added to each sample bottle to completely dissolve the Mitoquinone-C10: β-cyclodextrin complexes. Aliquots (50 μl) of these solutions were diluted to 1 ml with water. Aliquots (100 μl) of these diluted solutions of Mitoquinone-C10: β-cyclodextrin complexes were vortexed with 200 μl of a 10 μg/ml solution of internal standard in methanol. The samples were centrifuged for 10 min at 10000 rpm and 50 μl of the supernatants injected into the HPLC system. A standard curve was prepared using solutions of Mitoquinone-C10 in the concentration range 2.5 to 120 μg/ml containing 5 mg/ml solutions of β-cyclodextrin.

All the compounds were slightly orange-yellow in colour and very fluffy in appearance. The colour was not uniform and was more concentrated towards the bottom of the freeze drying flasks.

The results of DSC are given as follows:

Mitoquinone-C10: When a pure sample of Mitoquinone-C10 was analyzed, peaks were observed above 120° C. With one sample of Mitoquinone-C10, two prominent peaks were observed between 130° C. and 140° C. When another sample was analyzed, no such prominent peaks were observed but small peaks were observed above 120° C. After analysis, the pans were cut and the samples examined. The samples were dark green to black in colour in both cases.

β-cyclodextrin: There was a broad peak between 70° C. and 85° C.

Mitoquinone-C10: β-cyclodextrin (1:1) complex: No significant peaks were observed. After analysis the pan was cut and examined. The sample colour had undergone a slight change to light brown (not a significant change).

Mitoquinone-C10: β-cyclodextrin (1:2) complex: No significant peaks were observed. After analysis, no colour change in the sample was observed.

Mitoquinone-C10: β-cyclodextrin (1:4) complex: No significant peaks were observed but a very small exothermic peak was observed at 120° C. After analysis, no colour change in the sample was observed.

The appearance of peaks in the Mitoquinone-C10 pure sample indicates that changes in the compound are taking place with temperature. However, as there were many peaks and also colour changes in the sample, these could have arisen due to degradation. When a second sample of Mitoquinone-C10 was analyzed, it gave a different thermogram to the first sample. In the case of the complexes, there were no significant peaks or any colour changes.

Figure 11:
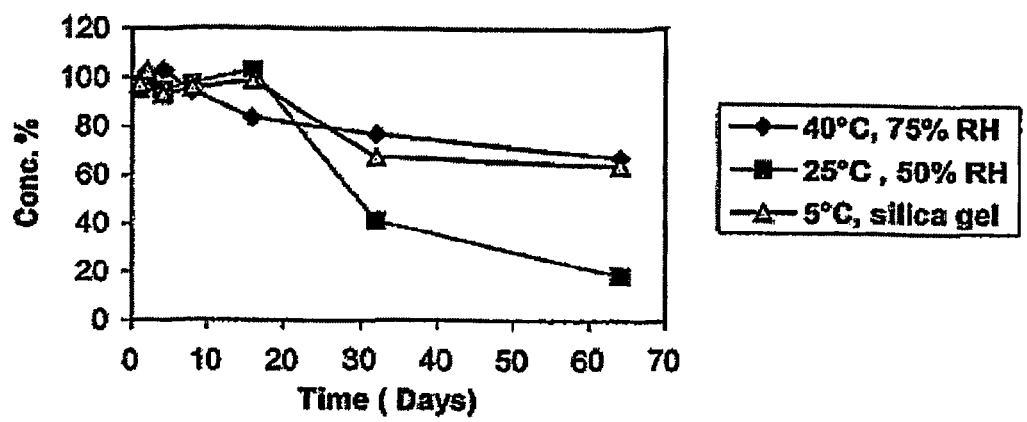
FIG. 11 is a graph depicting the stability of pure Mitoquinone-C10 (batch no. 3) in clear glass bottles at 40° C., 75% RH; 25° C., 50% RH and 5° C. over silica gel.

The results of the solid state stability study of pure Mitoquinone-C10 (batch no. 3) are given in Table 2 and FIG. 11.

TABLE 2

Solid state stability of Mitoquinone-C10 (batch no. 3).

| Clear Glass Bottles | Day 1 | Day 2 | Day 4 | Day 8 | Day 16 | Day 32 | Day 64 |
|---|---|---|---|---|---|---|---|
| 40° C., 75% RH | 98.90 | 101.9 | 102.8 | 94.07 | 83.22 | 76.70 | 67.25 |
| 25° C., 50% RH | 95.11 | 97.46 | 95.06 | 97.52 | 102.8 | 40.76 | 18.37 |
| 5° C., silica gel | 97.04 | 102.8 | 92.97 | 95.67 | 98.37 | 67.36 | 63.70 |

Solid state stability of Mitoquinone-C10 (batch no. 3) in the absence of light at 40° C., 75% RH; 25° C., 50% RH and 5° C. over blue silica gel. Data are means of two values expressed as percentage of original content.

Figure 12:
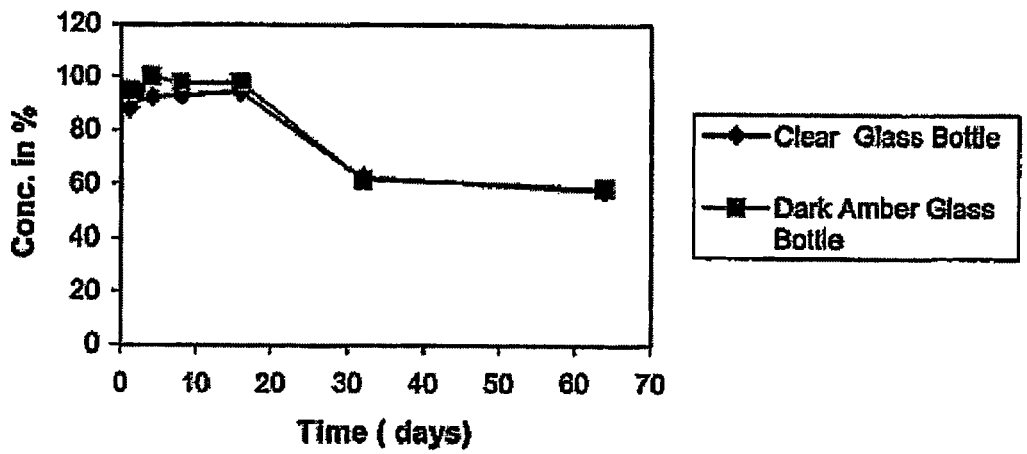
FIG. 12 is a graph depicting the stability of Mitoquinone-C10 (batch no. 4) at 25° C., 50% RH.

Due to the significant instability at 25° C., 50% RH compared to 40° C., 75% RH, the stability study was repeated at 25° C., 50% RH with Mitoquinone-C10 batch no. 4. The second stability study was conducted both in clear and amber bottles and the results are given in Table 3 and FIG. 12.

TABLE 3

Solid state stability of Mitoquinone-C10 (batch no. 4)

| | Time (days) | | | | | | |
|---|---|---|---|---|---|---|---|
| | 1 | 2 | 4 | 8 | 16 | 32 | 64 |
| Clear Glass Bottles | 88.21 | 93.19 | 92.65 | 93.10 | 94.47 | 62.05 | 57.94 |
| Dark Amber Glass Bottles | 94.84 | 94.52 | 100.28 | 97.65 | 98.03 | 61.48 | 58.66 |

Solid state stability of Mitoquinone-C10 (batch no. 4) was measured in the absence of light at 25° C., 50% RH. Data are means of three values expressed as percentage of the initial content.

Both batches (batches no. 3 and 4) of Mitoquinone-C10 supplied by the Chemistry Department showed a sudden drop in content after 16 days. However, for batch no. 4 the degradation was not as great after 32 to 64 days compared to batch no. 3. Also it was observed whether the bottles were clear or amber had no effect on Mitoquinone-C10 stability.

Figure 13:
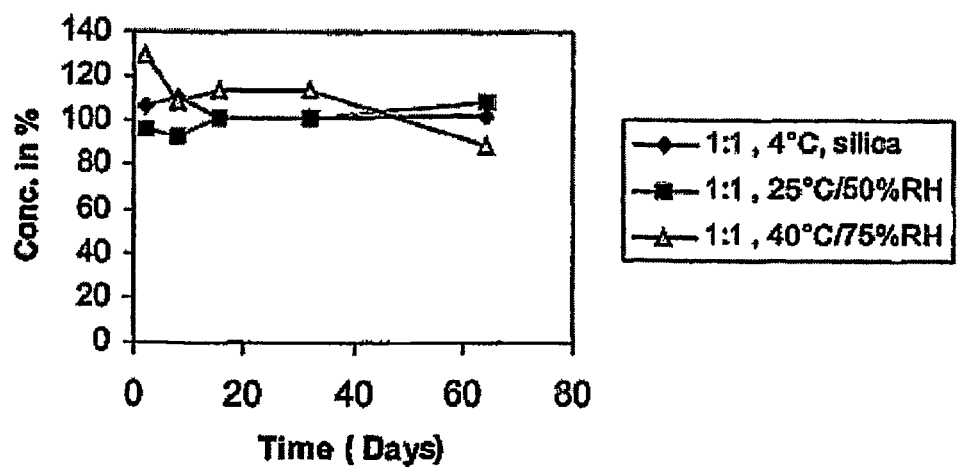
FIG. 13 is a graph depicting the stability of Mitoquinone-C10 β-cyclodextrin complex (1:1) at 4° C. over silica, 25° C., 50% RH and 40° C., 75% RH.
Figure 14:
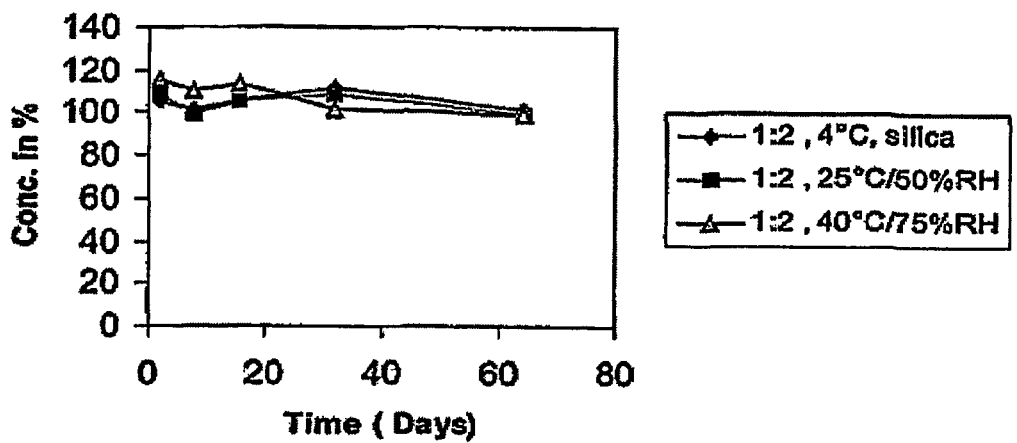
FIG. 14 is a graph depicting the stability of Mitoquinone-C10'-cyclodextrin complex (1:2) at 4° C. over silica, 25° C., 50% RH and 40° C., 75% RH.
Figure 15:
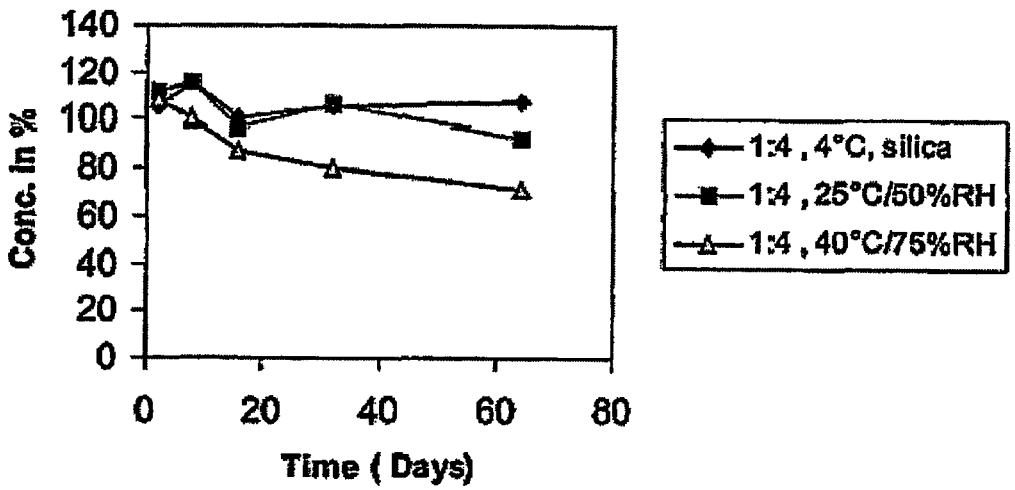
FIG. 15 is a graph depicting the stability of Mitoquinone-C10 β-cyclodextrin complex (1:4) at 4° C. over silica, 25° C., 50% RH and 40° C., 75% RH.
Figure 16:
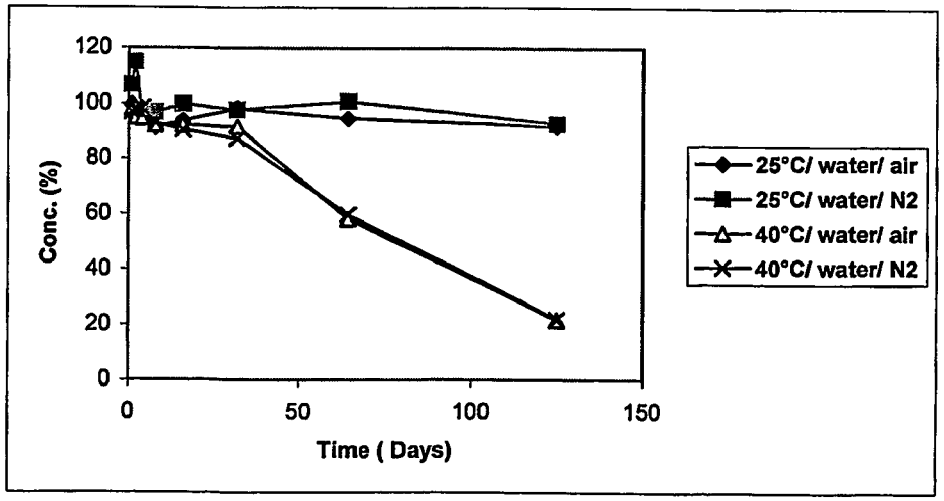
FIG. 16 presents a graph showing the stability of Mitoquinone-C10 mesylate in water.
Figure 17:
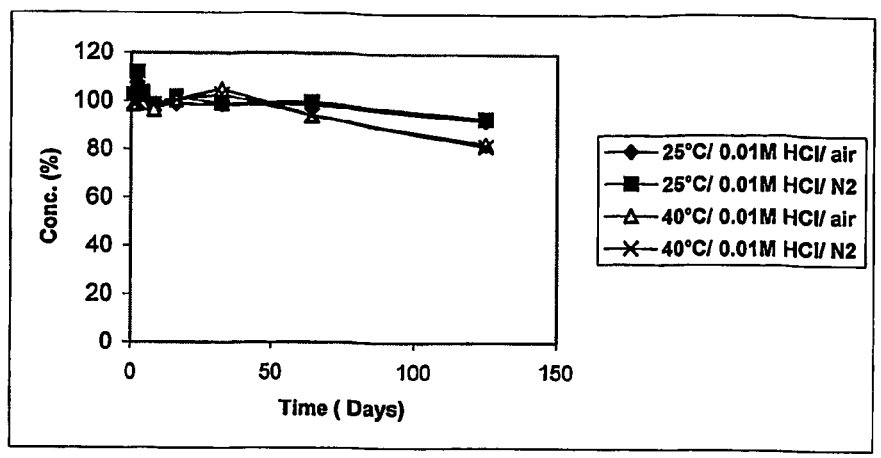
FIG. 17 presents a graph showing stability of Mitoquinone-C10 mesylate in 0.01M HCl.
Figure 18:
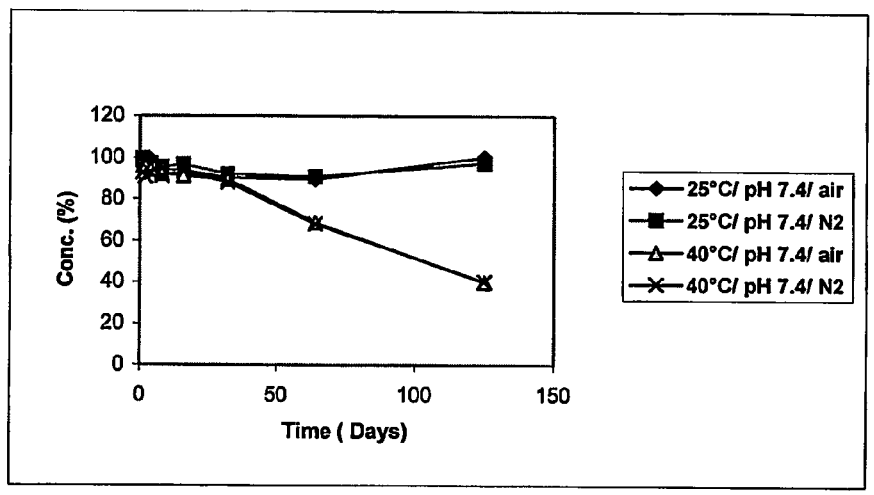
FIG. 18 presents a graph showing the stability of Mitoquinone-C10 mesylate in IPB, pH 7.4.
Figure 19:
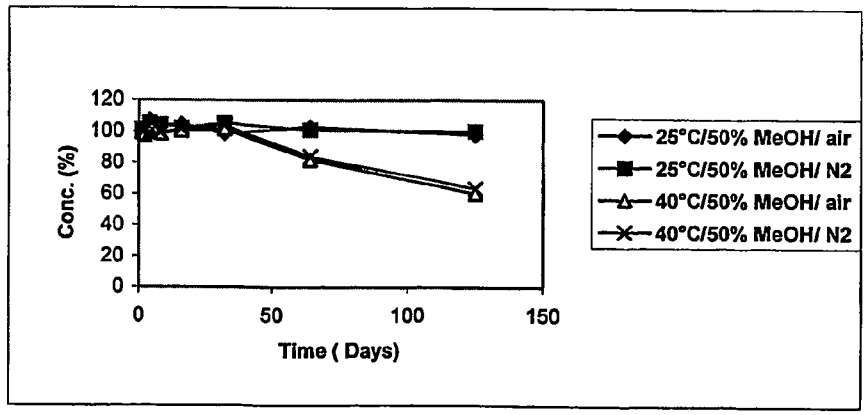
FIG. 19 presents a graph showing the stability of Mitoquinone-C10 mesylate in 50% MeOH

The Mitoquinone-C10 supplied from IRL was used for the preparation of the Mitoquinone-C10: β-cyclodextrin complexes. The Mitoquinone-C10 supplied from IRL was a reddish-yellow syrup in ethyl alcohol. The stability of the Mitoquinone-C10: β-cyclodextrin complexes is given in Table 4 and in FIGS. 13, 14 and 15. Because of the small amounts of Mitoquinone-C10: β-cyclodextrin complexes available for study, there are no results for day 1 and day 4.

TABLE 4

Solid state stability of Mitoquinone-C10:
β-cyclodextrin complexes

| | Time (days) | | | | |
|---|---|---|---|---|---|
| | 2 | 8 | 16 | 32 | 64 |
| 1:1 complex | | | | | |
| 4° C., silica | 106.38 | 110.97 | 101.71 | 101.71 | 102.68 |
| 25° C., 50% RH | 95.65 | 93.00 | 101.15 | 101.15 | 108.89 |
| 40° C., 75% RH | 129.22 | 108.77 | 113.48 | 113.49 | 89.25 |

TABLE 4-continued

Solid state stability of Mitoquinone-C10:
β-cyclodextrin complexes

| | Time (days) | | | | |
|---|---|---|---|---|---|
| | 2 | 8 | 16 | 32 | 64 |
| 1:2 complex | | | | | |
| 4° C., silica | 105.48 | 101.23 | 105.08 | 111.21 | 101.16 |
| 25° C., 50% RH | 108.16 | 95.46 | 105.41 | 108.55 | 99.78 |
| 40° C., 75% RH | 115.99 | 110.22 | 114.03 | 101.50 | 99.44 |
| 1:4 complex | | | | | |
| 4° C., silica | 105.10 | 115.86 | 100.25 | 107.63 | 107.63 |
| 25° C., 50% RH | 111.46 | 116.03 | 96.61 | 92.40 | 92.40 |
| 40° C., 75% RH | 108.85 | 100.01 | 87.34 | 71.13 | 71.13 |

Solid state stability of Mitoquinone-C10: β-cyclodextrin complexes in the absence of light at 40° C., 75% RH; 25° C., 50% RH and 5° C. over blue silica gel. Data are means of two values expressed as percentage.

The results show that Mitoquinone-C10 can effectively form complexes with β-cyclodextrin, and can be stabilized by complexing with β-cyclodextrin. The results show that Mitoquinone-C10 in the 1:1 and 1:2 β-cyclodextrin complexes was stable under various conditions. The results also show that the stability of Mitoquinone-C10 in the 1:4 complex was decreased relative to the stability of Mitoquinone-C10 in the 1:1 and 1:2 β-cyclodextrin complexes.

Example 8

Stability Studies of Mitoquinone-C10 Mesylate

Solution stability of Mitoquinone-C10 Mesylate

The solution stability of Mitoquinone-C10 mesylate was determined in five solvents; water, 0.01M HCl, 0.01M NaOH, IPB (pH 7.4) and 50% MeOH at two temperatures 25° C. and 40° C., under two atmospheric conditions, air and nitrogen, for 125 days as per the Applicant's standard operating procedure.

Mitoquinone-C10 mesylate solutions (100 μg/ml) in the five solvents were prepared by dilution of a stock solution of 1 mg/ml Mitoquinone-C10 mesylate in water. Solutions (5 ml) were placed in glass vials, flushed with air or nitrogen, sealed and placed on storage. Aliquots (0.25 ml) were collected at 0, 1, 2, 4, 8, 16, 32, 64 and 125 days and the concentration of Mitoquinone-C10 determined by HPLC.

The results are given in Table 5. The stability of Mitoquinone-C10 mesylate in 0.01M NaOH is not included because Mitoquinone-C10 mesylate decomposed in this solvent within 15 minutes. The results show that (a) solution stability is independent of the atmosphere above the solution and (b) temperature has a significant effect on the stability of Mitoquinone-C10 in all solvents except HCl.

TABLE 5

Solution stability of Mitoquinone-C10 mesylate in
4 different solvents under different conditions.

| Conditions | Time (Days) | | | | | | | |
|---|---|---|---|---|---|---|---|---|
| | 1 | 2 | 4 | 8 | 16 | 32 | 64 | 125 |
| Water, Air, 25° C. | 99.6 | 98.3 | 98.1 | 91.2 | 93.8 | 98.0 | 94.7 | 91.7 |
| Water, Air, 40° C. | 98.1 | 95.0 | 94.6 | 92.1 | 92.1 | 91.5 | 58.3 | 21.8 |
| 0.01M HCl, Air, 25° C. | 103.7 | 107.6 | 102.8 | 98.3 | 98.8 | 98.6 | 98.6 | 92.5 |
| 0.01M HCl, Air, 40° C. | 98.4 | 98.8 | 99.2 | 96.5 | 100.6 | 104.9 | 94.0 | 82.6 |
| IPB, Air, 25° C. | 95.6 | 95.8 | 98.6 | 94.5 | 93.7 | 90.4 | 89.6 | 100.3 |
| IPB, Air, 40° C. | 95.7 | 95.5 | 94.1 | 92.3 | 91.2 | 89.5 | 68.7 | 40.0 |
| 50% MeOH, Air, 25° C. | 97.7 | 97.1 | 106.9 | 103.6 | 104.5 | 98.6 | 102.8 | 98.0 |
| 50% MeOH, Air, 40° C. | 99.2 | 98.8 | 99.4 | 98.5 | 100.5 | 101.5 | 81.9 | 60.5 |
| Water, $N_2$, 25° C. | 106.7 | 114.9 | 96.8 | 96.7 | 99.7 | 97.6 | 100.8 | 92.7 |
| Water, $N_2$, 40° C. | 97.0 | 97.5 | 98.3 | 93.0 | 90.4 | 87.3 | 59.8 | 22.0 |
| 0.01M HCl, $N_2$, 25° C. | 102.7 | 112.0 | 103.6 | 98.8 | 101.7 | 98.9 | 99.6 | 93.1 |
| 0.01M HCl, $N_2$, 40° C. | 99.3 | 99.6 | 100.2 | 98.3 | 100.4 | 102.9 | 94.1 | 88.8 |
| IPB, $N_2$, 25° C. | 99.6 | 96.5 | 96.9 | 95.3 | 96.6 | 91.9 | 90.9 | 97.5 |
| IPB, $N_2$, 40° C. | 92.8 | 90.9 | 92.7 | 91.2 | 93.3 | 88.1 | 68.0 | 40.3 |
| 50% MeOH, $N_2$, 25° C. | 101.2 | 97.3 | 105.1 | 104.2 | 102.0 | 105.0 | 101.0 | 100.2 |
| 50% MeOH, $N_2$, 40° C. | 99.8 | 100.5 | 99.3 | 98.9 | 101.5 | 103.6 | 83.8 | 63.6 |

Data are the mean of two values expressed as percentage of the time zero value.

The solution stability of Mitoquinone-C10 mesylate in four solvents is also shown in FIGS. 16, 17, 18, and 19.

Solid State Stability of Mitoquinone-C10 Mesylate

Solid state stability of Mitoquinone-C10 mesylate was studied in the absence of light under three different conditions; 40° C., 75% RH; 25° C., 50% RH; and 4° C. over blue silica gel as per the Applicant's standard operating procedure.

Figure 20:
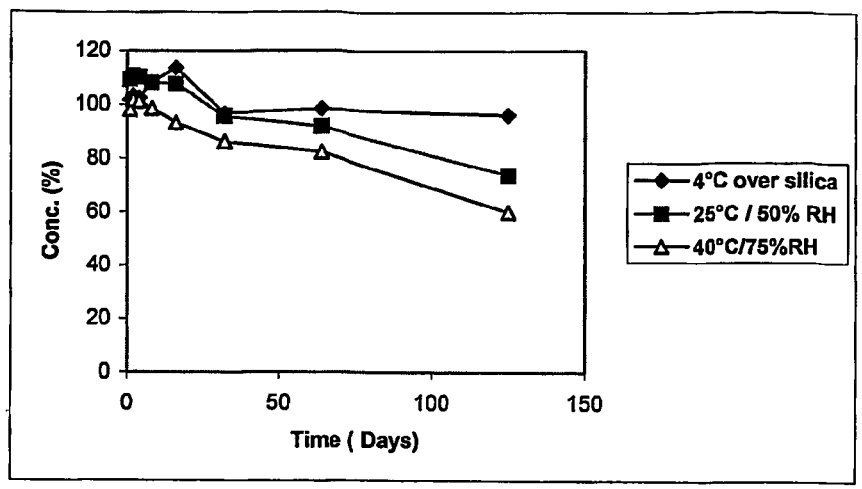
FIG. 20 presents a graph showing the solid state stability of Mitoquinone-C10 mesylate at 40° C., 75% RH; and 25° C., 50% RH and 4° C. over blue silica gel.
Figure 21:
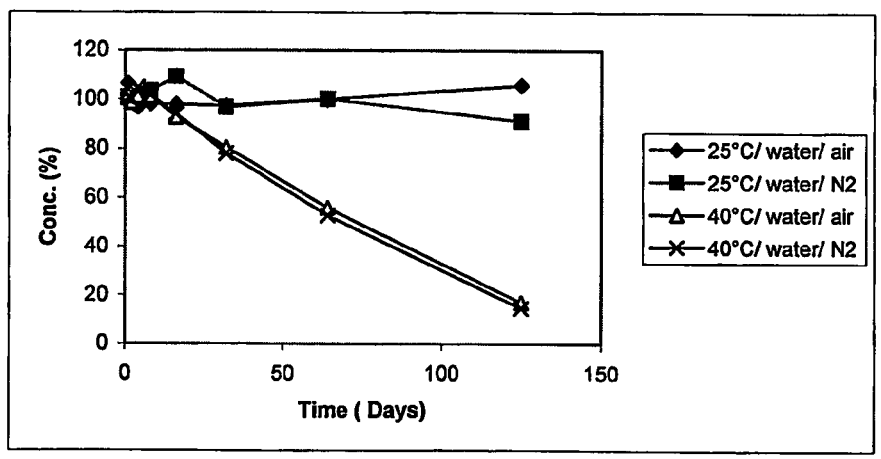
FIG. 21 presents a graph showing the stability of Mitoquinone-C10 mesylate-β-cyclodextrin (1:2) complex in water.
Figure 22:
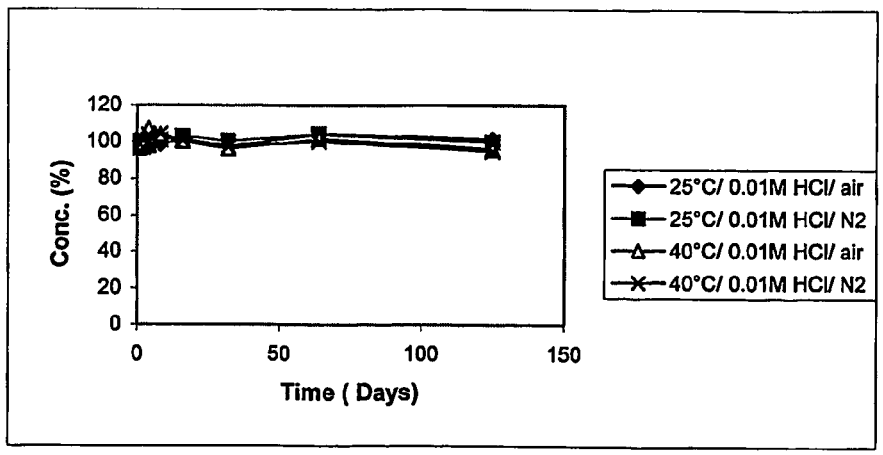
FIG. 22 presents a graph showing the stability of Mitoquinone-C10 mesylate-β-cyclodextrin (1:2) complex in 0.01M HCl.
Figure 23:
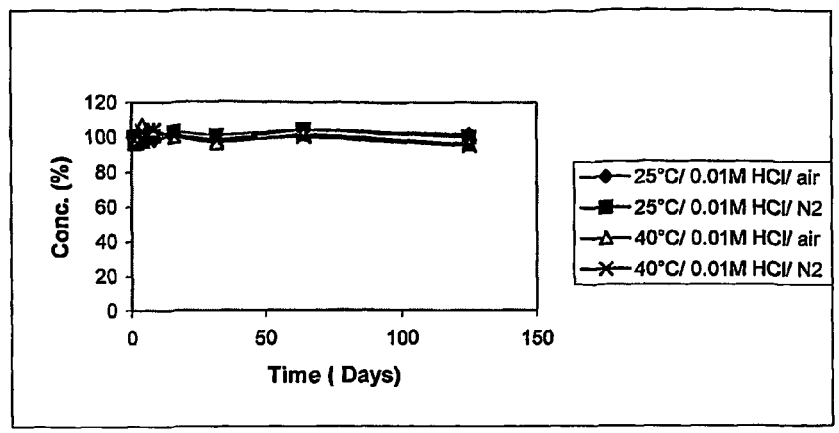
FIG. 23 presents a graph showing the stability of Mitoquinone-C10 mesylate-α-cyclodextrin (1:2) complex in IPB, pH7.4.
Figure 24:
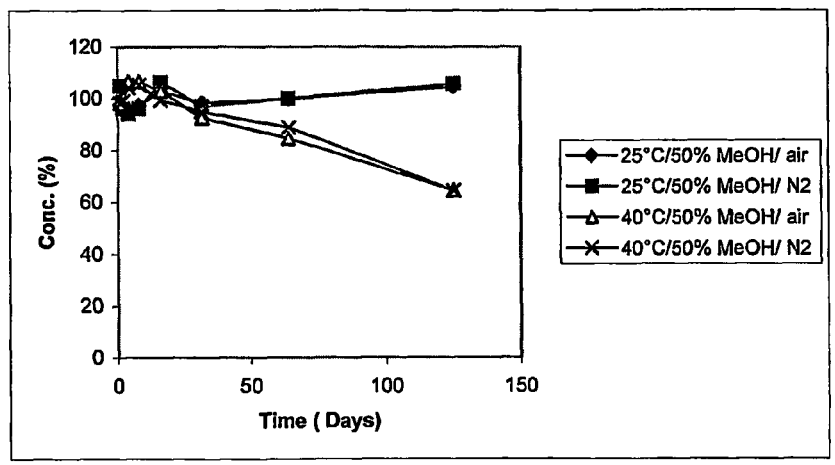
FIG. 24 presents a graph showing the stability of Mitoquinone-C10 mesylate-α-cyclodextrin (1:2) complex in 50% MeOH.

A known weight of Mitoquinone-C10 mesylate was put in clear glass bottles and stored under different conditions. Duplicate samples were withdrawn at 1, 2, 4, 8, 16, 32, 64 and 125 days and the concentration of Mitoquinone-C10 mesylate determined by HPLC after dissolving the samples in water. The results are given in Table 6 and in FIG. 20.

Mitoquinone-C10 mesylate was stable (<10% decomposition) at 4° C. over silica gel for 125 days and at 25° C./50% RH for 60 days.

TABLE 6

Solid state stability of Mitoquinone-C10 mesylate at 40° C.,
75% RH; 25° C., 50% RH; and 4° C. over blue silica gel.

| | Time (Days) | | | | | | | |
|---|---|---|---|---|---|---|---|---|
| | 1 | 2 | 4 | 8 | 16 | 32 | 64 | 125 |
| 4° C. over silica | 101.6 | 103.4 | 102.4 | 108.2 | 113.5 | 96.6 | 98.2 | 96.0 |
| 25° C./50% RH | 109.2 | 110.7 | 110.2 | 108.1 | 107.6 | 95. | 91.6 | 73.7 |
| 40° C./75% RH | 98.0 | 101.7 | 101.3 | 98.5 | 93.1 | 86.1 | 82.1 | 59.9 |

The data are the mean of two values expressed as percentage of the time zero value.

Example 9

Stability Studies of Mitoquinone-C10 Mesylate-β-Cyclodextrin (1:2) Complex

Solution Stability of Mitoquinone-C10 Mesylate-β-Cyclodextrin (1:2) Complex

The solution stability of Mitoquinone-C10 mesylate-β-cyclodextrin (1:2) complex was determined in five solvents; water, 0.01M HCl, 0.01M NaOH, IPB (pH7.4) and 50% MeOH at two temperatures 25° C. and 40° C., under two atmospheric conditions, air and nitrogen, for 64 days as per the Applicant's standard operating procedure.

Mitoquinone-C10 mesylate-β-cyclodextrin (1:2) complex solutions (100 μg/ml as Mitoquinone-C10 mesylate) in the five solvents were prepared by dilution of a stock solution of Mitoquinone-C10 mesylate-β-cyclodextrin (1:2) complex (1 mg/ml as Mitoquinone-C10 mesylate) in water. Solutions (5 ml) were placed in glass vials, flushed with air or nitrogen, sealed and placed on storage. Aliquots (0.25 ml) were collected at 0, 1, 2, 4, 8, 16, 32, 64 and 125 days and the concentration determined by HPLC.

The results are given in Table 7 and in FIGS. 21, 22, 23, and 24. The stability of Mitoquinone-C10 mesylate-β-cyclodextrin (1:2) complex in 0.01M NaOH is not included because Mitoquinone-C10 mesylate-β-cyclodextrin (1:2) complex decomposed in this solvent within 15 minutes. The results show that (a) solution stability is independent of the atmosphere above the solution and (b) temperature has a significant effect on the stability of Mitoquinone-C10 mesylate in the 1:2 complex with β-cyclodextrin in all solvents except HCl.

TABLE 7

Solution stability of Mitoquinone-C10 mesylate-β-cyclodextrin
(1:2) complex in 4 different solvents under different conditions.

| Conditions | Time (Days) | | | | | | | |
|---|---|---|---|---|---|---|---|---|
| | 1 | 2 | 4 | 8 | 16 | 32 | 64 | 125 |
| Water, Air, 25° C. | 106.5 | 103.3 | 96.7 | 98.1 | 97.9 | 97.5 | 100.0 | 105.8 |
| Water, Air, 40° C. | 102.0 | 98.7 | 101.3 | 101.4 | 92.8 | 80.5 | 55.9 | 17.2 |
| 0.01M HCl, Air, 25° C. | 96.4 | 100.5 | 99.9 | 98.6 | 101.5 | 97.6 | 104.5 | 101.6 |
| 0.01M HCl, Air, 40° C. | 96.6 | 98.4 | 107.1 | 104.0 | 100.4 | 96.4 | 101.0 | 96.2 |
| IPB, Air, 25° C. | 97.4 | 94.3 | 98.3 | 96.1 | 107.5 | 97.3 | 97.3 | 99.5 |
| IPB, Air, 40° C. | 95.2 | 93.2 | 97.8 | 98.8 | 91.7 | 87.5 | 74.2 | 55.9 |
| 50% MeOH, Air, 25° C. | 97.8 | 96.2 | 95.8 | 97.5 | 102.8 | 98.3 | 99.7 | 104.5 |
| 50% MeOH, Air, 40° C. | 99.5 | 98.1 | 106.5 | 106.5 | 102.9 | 92.6 | 84.6 | 64.6 |
| Water, $N_2$, 25° C. | 101.1 | 98.3 | 102.4 | 103.5 | 109.3 | 96.8 | 100.3 | 91.3 |
| Water, $N_2$, 40° C. | 100.6 | 100.3 | 104.8 | 101.6 | 94.1 | 78.1 | 52.8 | 14.9 |
| 0.01M HCl, $N_2$, 25° C. | 100.1 | 100.7 | 97.9 | 101.0 | 103.0 | 100.6 | 104.3 | 100.0 |
| 0.01M HCl, $N_2$, 40° C. | 98.6 | 96.8 | 103.7 | 104.2 | 100.6 | 97.8 | 100.3 | 95.14 |
| IPB, $N_2$, 25° C. | 102.0 | 97.9 | 99.6 | 95.6 | 104.6 | 93.9 | 96.9 | 98.7 |
| IPB, $N_2$, 40° C. | 92.1 | 93.7 | 95.2 | 93.1 | 90.3 | 86.6 | 73.9 | 54.8 |
| 50% MeOH, $N_2$, 25° C. | 105.0 | 96.0 | 94.1 | 96.1 | 106.4 | 97.0 | 100.0 | 105.7 |
| 50% MeOH, $N_2$, 40° C. | 98.3 | 98.9 | 104.2 | 105.3 | 99.4 | 94.9 | 88.8 | 64.4 |

Data are the mean of two values expressed as percentage of the time zero value.

Solid State Stability of Mitoquinone-C10 Mesylate-β-Cyclodextrin (1:2) Complex

Solid state stability of Mitoquinone-C10 mesylate-β-cyclodextrin (1:2) complex was studied in the absence of light under three different conditions; 40° C., 75% RH; 25° C., 50% RH; and 4° C. over blue silica gel as per the Applicant's standard operating procedure.

Figure 25:
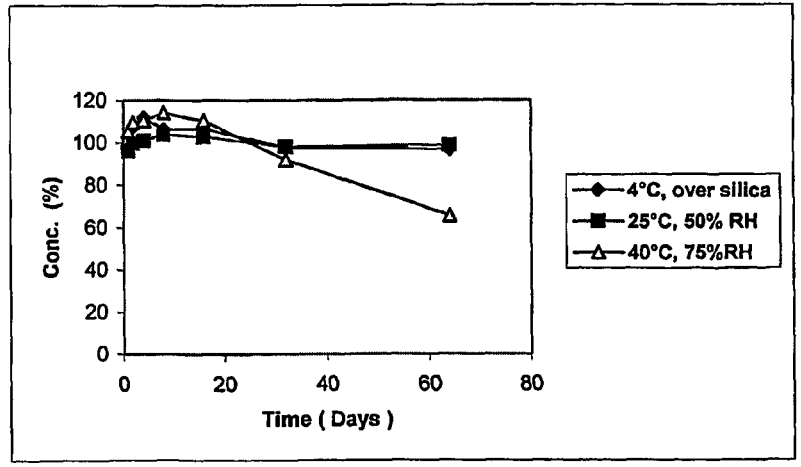
FIG. 25 presents a graph showing the solid state stability of Mitoquinone-C10 mesylate-β-cyclodextrin (1:2) complex at 40° C., 75% RH; at 25° C., 50% RH, and 4° C. over blue silica gel.
Figure 26:
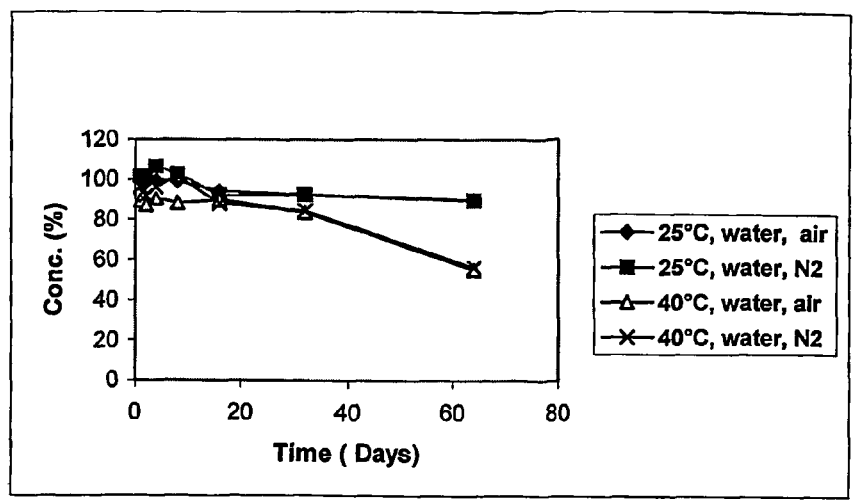
FIG. 26 presents a graph showing the stability of Mitoquinone-C10 mesylate-β-cyclodextrin (1:1) complex in water.
Figure 27:
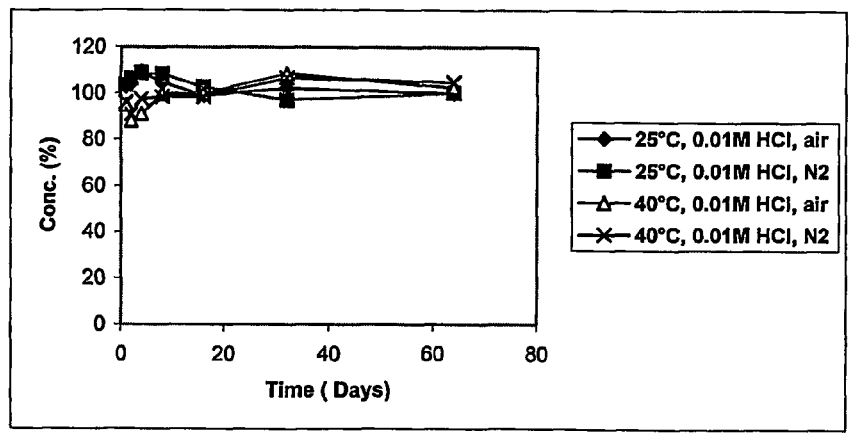
FIG. 27 presents a graph showing the stability of Mitoquinone-C10 mesylate-β-cyclodextrin (1:1) complex in 0.01M HCl.
Figure 28:
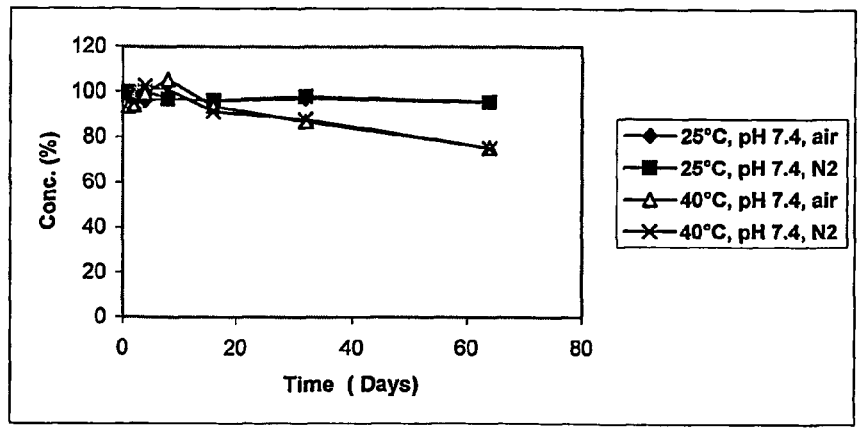
FIG. 28 presents a graph showing the stability of Mitoquinone-C10 mesylate-β-cyclodextrin (1:1) complex in IPB pH 7.4.
Figure 29:
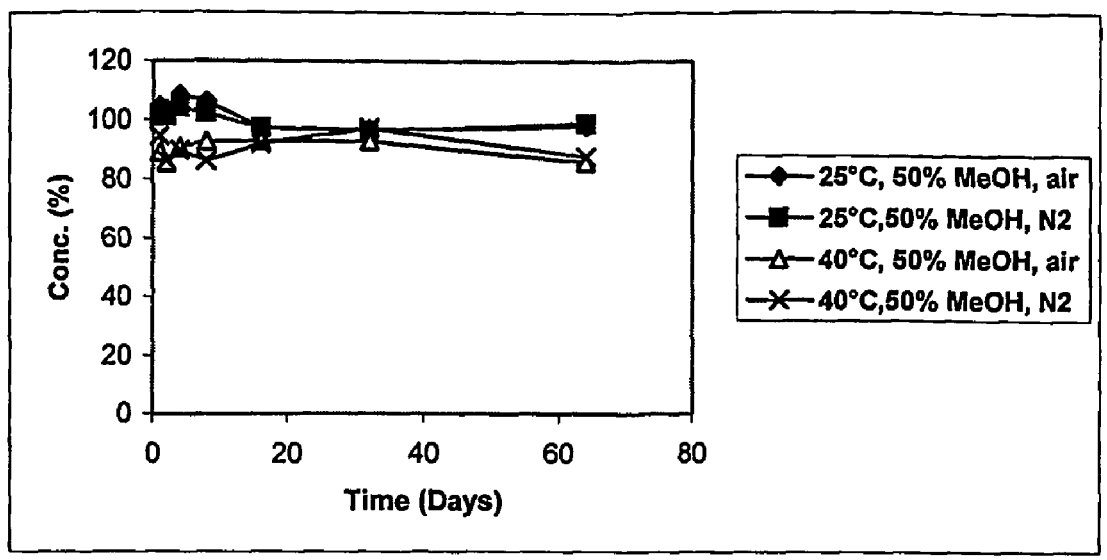
FIG. 29 presents a graph showing the stability of Mitoquinone-C10 mesylate-β-cyclodextrin (1:1) complex in 50% methanol.

A known weight of Mitoquinone-C10 mesylate-β-cyclodextrin (1:2) complex was put in clear glass bottles and stored under different conditions. Duplicate samples were withdrawn at 1, 2, 4, 8, 16, 32, 64 and 125 days and the concentration of Mitoquinone-C10 mesylate determined by HPLC after dissolving the samples in water. The results are given in Table 8 and in FIG. 25. The results show that Mitoquinone-C10 mesylate was stable in Mitoquinone-C10 mesylate-β-cyclodextrin (1:2) complex at 4° C. over blue silica gel and at 25° C., 50% RH. At 40° C., 75% RH, 37% of the Mitoquinone-C10 mesylate was degraded in Mitoquinone-C10 mesylate-β-cyclodextrin (1:2) complex on storage for 64 days.

TABLE 8

Solid state stability of Mitoquinone-C10 mesylate-
β-cyclodextrin (1:2) complex at 40° C., 75% RH;
25° C., 50% RH and 4° C. over blue silica gel.

| | Time (Days) | | | | | | | |
|---|---|---|---|---|---|---|---|---|
| | 1 | 2 | 4 | 8 | 16 | 32 | 64 | 125 |
| 4° C. over silica | 97.6 | 107.6 | 111.8 | 106.3 | 106.8 | 97.7 | 96.8 | 99.9 |
| 25° C./50% RH | 96.0 | 99.7 | 101.0 | 104.1 | 102.9 | 98.1 | 98.7 | 99.6 |

TABLE 8-continued

Solid state stability of Mitoquinone-C10 mesylate-
β-cyclodextrin (1:2) complex at 40° C., 75% RH;
25° C., 50% RH and 4° C. over blue silica gel.

| | Time (Days) | | | | | | | |
|---|---|---|---|---|---|---|---|---|
| | 1 | 2 | 4 | 8 | 16 | 32 | 64 | 125 |
| 40° C./75% RH | 105.5 | 109.7 | 110.6 | 114.3 | 110.5 | 92.0 | 65.5 | 51.5* |

The data are the mean of two values expressed as percentage of the time zero value.
*Mean of two very different values (71.9 and 31.1%).

Example 10

Stability Studies of Mitoquinone-C10 Mesylate—β-Cyclodextrin (1:1) Complex

Solution Stability

The solution stability of Mitoquinone-C10 mesylate-β-cyclodextrin (1:1) complex was determined in five solvents; water, 0.01M HCl, 0.01M NaOH, IPB (pH7.4) and 50% MeOH at two temperature 25° C. and 40° C., under two atmospheric conditions, air and nitrogen, for 64 days as per the Applicant's standard operating procedure.

Mitoquinone-C10 mesylate-1-cyclodextrin (1:1) complex solutions (100 μg/ml in Mitoquinone-C10 mesylate) in the five solvents were prepared by dilution of a stock solution of Mitoquinone-C10 mesylate-β-cyclodextrin (1:1) complex (1 mg/ml as Mitoquinone-C10 mesylate) in water. Solutions (5 ml) were placed in glass vials flushed with air or nitrogen, sealed and placed on storage. Aliquots (0.25 ml) were collected at 0, 1, 2, 4, 8, 16, 32, 64 and 125 days and the concentration determined by HPLC.

The results are given in Table 9 and in FIGS. 26, 27, 28, and 29. The stability of Mitoquinone-C10 mesylate-β-cyclodextrin (1:1) in 0.01M NaOH is not included because Mitoquinone-C10 mesylate decomposed in this solvent within 15 minutes. The results show that (a) solution stability is independent of the atmosphere above the solution and (b) temperature has a significant effect on the stability of Mitoquinone-C10 mesylate in the 1:1 complex with β-cyclodextrin in water and IPB but not in HCl or 50% MeOH.

TABLE 9

Solution stability of Mitoquinone-C10 mesylate-β-cyclodextrin
(1:1) in 4 different solvents under different conditions.

| Conditions | Time (Days) | | | | | | |
|---|---|---|---|---|---|---|---|
| | 1 | 2 | 4 | 8 | 16 | 32 | 64 |
| Water, Air, 25° C. | 101.3 | 98.2 | 99.5 | 99.0 | 94.0 | 92.7 | 89.8 |
| Water, Air, 40° C. | 89.4 | 87.2 | 90.4 | 88.1 | 89.8 | 83.9 | 55.2 |
| 0.01M HCl, Air, 25° C. | 103.0 | 104.3 | 109.4 | 104.6 | 99.1 | 102.2 | 100.0 |
| 0.01M HCl, Air, 40° C. | 94.9 | 88.22 | 91.17 | 99.76 | 99.74 | 108.5 | 102.6 |
| IPB, Air, 25° C. | 97.9 | 95.7 | 96.1 | 97.1 | 96.1 | 97.1 | 95.5 |
| IPB, Air, 40° C. | 93.5 | 94.1 | 99.4 | 105.4 | 93.6 | 86.9 | 75.3 |
| 50% MeOH, Air, 25° C. | 104.8 | 103.7 | 108.7 | 106.4 | 97.6 | 96.9 | 98.1 |
| 50% MeOH, Air, 40° C. | 89.3 | 85.68 | 91.01 | 93.0 | 93.1 | 92.9 | 85.9 |
| Water, $N_2$, 25° C. | 101.7 | 101.3 | 106.4 | 102.7 | 92.0 | 92.4 | 89.6 |
| Water, $N_2$, 40° C. | 96.2 | 91.7 | 95.9 | 101.6 | 88.0 | 84.5 | 56.5 |
| 0.01M HCl, $N_2$, 25° C. | 103.7 | 106.5 | 108.7 | 108.2 | 102.7 | 97.2 | 100.3 |
| 0.01M HCl, $N_2$, 40° C. | 96.2 | 90.9 | 97.5 | 98.5 | 98.5 | 106.7 | 104.8 |
| IPB, $N_2$, 25° C. | 100.1 | 99.2 | 100.4 | 97.1 | 96.4 | 98.2 | 95.5 |
| IPB, $N_2$, 40° C. | 98.4 | 95.3 | 102.7 | 101.0 | 91.4 | 87.9 | 75.7 |
| 50% MeOH, $N_2$, 25° C. | 101.2 | 101.4 | 104.5 | 102.4 | 97.6 | 96.4 | 99.0 |
| 50% MeOH, $N_2$, 40° C. | 94.7 | 86.4 | 90.0 | 86.4 | 92.1 | 97.4 | 87.7 |

Data are the mean of two values expressed as percentage of the time zero value.

Solid State Stability

Solid state stability of Mitoquinone-C10 mesylate-β-cyclodextrin (1:1) complex was studied in the absence of light under three different conditions; 40° C., 75% RH; 25° C., 50% RH; and 4° C. over blue silica gel as per the Applicant's standard operating procedure.

Figure 30:
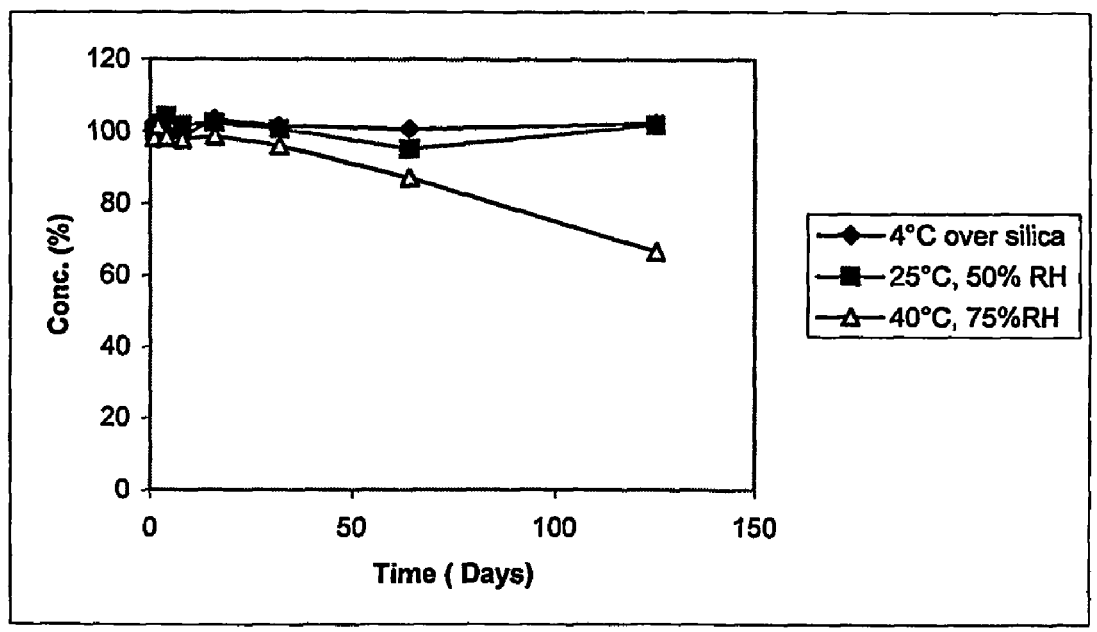
FIG. 30 presents a graph showing the solid state stability of Mitoquinone-C10 mesylate-β-cyclodextrin (1:1) complex at 40° C., 75% RH; 25° C., 50% RH and 4° C. over blue silica gel.

A known weight of Mitoquinone-C10 mesylate-β-cyclodextrin (1:1) complex was put in clear glass bottles and stored under different conditions. Duplicate samples were withdrawn at 1, 2, 4, 8, 16, 32, 64 and 125 days and the concentration of Mitoquinone-C10 mesylate determined by HPLC after dissolving the samples in water. The results are given in Table 10 and in FIG. 30. The results show that Mitoquinone-C10 mesylate was stable at 4° C. over silica gel and at 25° C., 50% RH but 37% of the Mitoquinone-C10 mesylate was degraded in Mitoquinone-C10 mesylate-β-cyclodextrin (1:1) on storage for 125 days at 40° C., 75% RH.

TABLE 10

Solid state stability of Mitoquinone-C10 mesylate-
β-cyclodextrin (1:1) complex at 40° C., 75% RH;
25° C., 50% RH and 4° C. over blue silica gel.

| | Time (Days) | | | | | | | |
|---|---|---|---|---|---|---|---|---|
| | 1 | 2 | 4 | 8 | 16 | 32 | 64 | 125 |
| 4° C. over silica | 102.1 | 97.7 | 100.0 | 98.5 | 103.4 | 101.4 | 100.6 | 102.3 |
| 25° C./50% RH | 99.7 | 101.6 | 104.2 | 101.8 | 102.4 | 100.7 | 95.2 | 101.9 |
| 40° C./75% RH | 98.2 | 101.6 | 98.3 | 97.8 | 98.8 | 96.0 | 87.2 | 66.7 |

The data are the mean of two values expressed as percentage of the time zero value.

Example 11

Pharmacokinetic Study of a Single IV and Oral Dose of Mitoquinone-C10 Mesylate-β-Cyclodextrin (1:2) Complex in Rat (P2 & P3)

Based on the results of a previous pharmacokinetic study of Mitoquinone-C10 bromide and an acute oral toxicity study of Mitoquinone-C10 mesylate-β-cyclodextrin (1:2) complex, doses of Mitoquinone-C10 mesylate-β-cyclodextrin (1:2) complex for the pharmacokinetic study were 50 mg/kg Mitoquinone-C10 mesylate for the oral dose and 10 mg/kg Mitoquinone-C10 mesylate for the IV dose.

Ten female Wistar rats (mean weight approximately 236 g) were cannulated with Silastic tubing in the right jugular vein under halothane anaesthesia 48 h before an experiment. An aqueous Mitoquinone-C10 mesylate-β-cyclodextrin (1:2) complex solution (10 mg/ml as Mitoquinone-C10 mesylate) was freshly prepared and administered by either the oral (n=5) or IV route (n=5). Blood samples (0.2 ml) were collected at 0, 5, 10, 20, 30, 45, 60, 90, 120, 180, 240, 360, 720, and 1440 (24 h) min after the IV dose and at 0, 15, 30, 60, 90, 120, 150, 180, 240, 300, 420, 540, 720, and 1440 (24 h) min after the oral dose. Blood samples were centrifuged and plasma samples (0.1 ml) were stored in the −20° C. freezer. Samples of 24 h urine and feces were also collected.

The Mitoquinone-C10 mesylate concentration in plasma was determined by ESR using LC/MS (Table 12).

Pharmacokinetic Analysis

The pharmacokinetics of Mitoquinone-C10 were analysed by iterative unweighted non-linear least-squares regression analysis using MINIM. The IV data were fitted using one-, two- and three-compartment models. The model giving the best fit was the one with the minimum value according to Akaike's information criterion (A.I.C). The plasma drug concentration-time curves after drug administration were found to be best and adequately fitted by a three-compartment open model described by the following equation $$C = Ae^{-\alpha t} + Be^{-\beta t} + Ee^{31\gamma t}$$

where C is the plasma drug concentration, A, B and E are mathematical coefficients, α is the rate constant for the distribution phase, β is the rate constant for an intermediate phase (distribution or elimination) and γ is the rate constant for a terminal, slower elimination phase. Drug elimination half-life ($t^{1/2}$) in the terminal phase was calculated as $t_{1/2}=0.693/\gamma$. Oral data (post 4 h) were fitted with a one-compartment model. The peak concentration ($C_{max}$) and time to reach $C_{max}$ ($t_{max}$) were obtained directly from the concentration-time profile. The area under the plasma concentration-time curve (AUC) was estimated using the linear trapezoidal rule, with extrapolation from the last measured concentration to infinity determined by use of the terminal elimination rate constant (γ). The total plasma clearances after intravenous (CL) and oral (CL/F) administration were estimated as CL=dose/AUC. Volumes of distribution were calculated as $V_\beta$=dose/(AUC·β) and Vγ=dose/(AUC·γ). Absolute bioavailability (F) was calculated as: F=$AUC_{po} \times Dose_{iv}/AUC_{iv} \times Dose_{po}$. Mean residence time (MRT) was calculated as AUMC/AUC. Apparent volume of distribution at steady state (Vss) was calculated as $dose_{iv} \times AUMC/(AUC)^2$.

Results and Discussion

Figure 31:
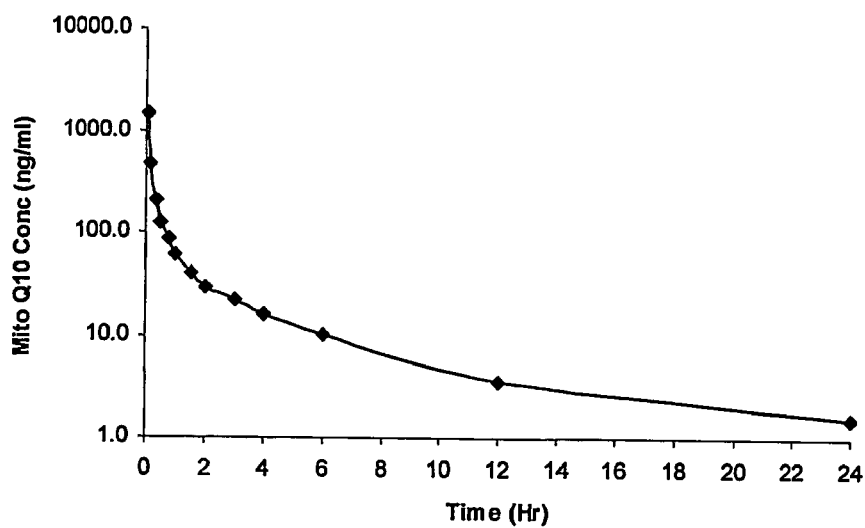
FIG. 31 presents graphs of Rat plasma concentration-time profiles of Mitoquinone-C10 after single IV (A) (10 mg/kg) and oral (B) (50 mg/kg) administration to rats of Mitoquinone-C10 mesylate in Mitoquinone-C10 mesylate-β-cyclodextrin (1:2) complex (n=5). Pharmacokinetic parameters derived from these data are given in Table 11.
Figure 31:
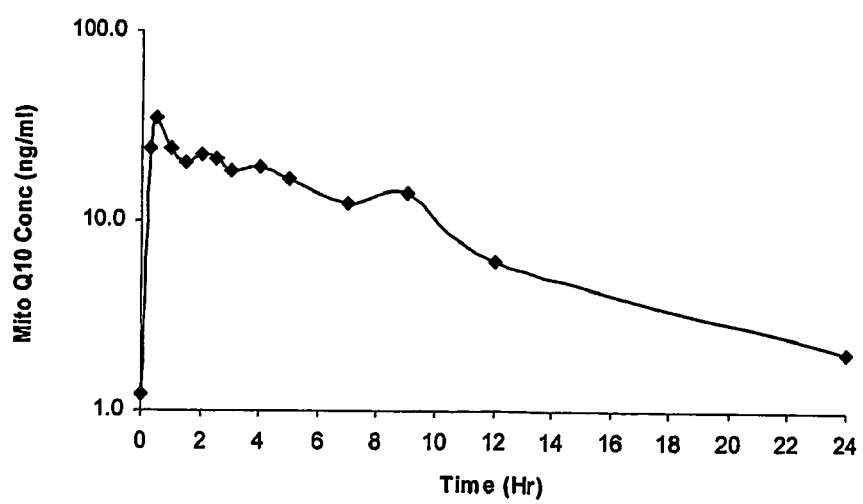

The mean plasma concentration-time profiles of Mitoquinone-C10 mesylate after IV and oral administration of Mitoquinone-C10 mesylate-β-cyclodextrin (1:2) complex are shown in FIG. 31 and the mean pharmacokinetic parameters are listed in Table 11. Original data of plasma levels of Mitoquinone-C10 mesylate are attached (Table 12).

TABLE 11

Pharmacokinetic parameters of Mitoquinone-C10 mesylate administered as Mitoquinone-C10 mesylate-β-cyclodextrin (1:2) complex in rat after single IV (10 mg/kg) and oral (50 mg/kg) doses

|  | IV Mitoquinone-C10 (n = 5) | Oral Mitoquinone-C10 (n = 5) |
|---|---|---|
| Body Weight (g) | 236.8 ± 21.0 | 236.8 ± 22.9 |
| $C_{max}$ (ng/ml) | — | 35.1 |
| $t_{max}$ (min) | — | 30 |
| $t_{1/2\alpha}$ (min) | 1.6 ± 0.3 | — |
| $t_{1/2\beta}$ (min) | 10.4 ± 3.2 | — |
| $t_{1/2\gamma}$ (h) | 1.83 ± 0.44 | — |
| $t_{1/2}$ (h) | 14.3* | 13.9** |
| AUC (μg · min/ml) | 47.3 ± 11.1 | 29.3 ± 2.7 |
| AUMC (μg · min²/ml) | 5292 ± 831 | 7477 ± 365 |
| F (%) | 100 | 12.4 |
| CL (l/min/kg) | 0.22 ± 0.04 | — |
| CL/F (l/min/kg) | — | 13.7 ± 1.3 |
| $V_\beta$ (l/kg) | 3.33 ± 1.46 | — |
| $V_\gamma$ (l/kg) | 24.04 ± 18.3 | — |
| MRT (h) | 4.2 ± 0.5 | 9.5 ± 2.2 |
| Vss (l/kg) | 25.2 ± 6.5 | — |

*$t_{1/2}$ value obtained from mean concentrations at times >4 h
**$t_{1/2}$ value obtained from mean concentrations at times >4 h

TABLE 12

Mitoquinone-C10 concentration in Rat Plasma for the P2-IV and P3-PO study

| Time (min) | 01 IV (ng/ml) | 2 IV (ng/ml) | 3 IV (ng/ml) | 4 IV (ng/ml) | 5 IV (ng/ml) | Time (Hr) | Mean |
|---|---|---|---|---|---|---|---|
| 0 | 0.495 | 0.348 | 30.4 | 1.39 | 1.39 | 0 | |
| 5 | 1010 | 867 | 1550 | 2300 | 1640 | 0.1 | 1473.4 |
| 10 | 306 | 391 | 572 | 641 | 476 | 0.2 | 477.2 |
| 20 | 199 | 186 | 221 | 251 | 192 | 0.3 | 209.8 |
| 30 | 132 | 111 | 117 | 158 | 111 | 0.5 | 125.8 |
| 45 | 90.5 | 87.5 | 70 | 113 | 72.3 | 0.8 | 86.7 |
| 60 | 62.1 | 59.4 | 56.4 | 72.5 | 48.7 | 1.0 | 59.8 |
| 90 | 36.4 | 37.9 | 38.9 | 57.4 | 29.4 | 1.5 | 40.0 |
| 120 | 23.2 | 25.3 | 24.2 | 54.8 | 18.8 | 2.0 | 29.3 |
| 180 | 17.8 | 21.3 | 20.7 | 30.2 | 22 | 3.0 | 22.4 |
| 240 | 13.1 | 12.9 | 16.4 | 27.4 | 9.63 | 4.0 | 15.9 |
| 360 | 7.01 | 8.89 | 11.5 | 16.7 | 7.46 | 6.0 | 10.3 |
| 720 | 2.8 | 3.44 | 5.66 | 4.07 | 2.19 | 12.0 | 3.6 |
| 1440 | 1.49 | 1.63 | 1.47 | 1.37 | 1.96 | 24.0 | 1.6 |
| Urine | 19.3 | 52.6 | 48.5 | 10.1 | 12.9 | | |

| Time (min) | 06 PO (ng/ml) | 07 PO (ng/ml) | 08 PO (ng/ml) | 09 PO (ng/ml) | 10 PO (ng/ml) | Time (Hr) | Mean |
|---|---|---|---|---|---|---|---|
| 0 | 0.878 | 2.15 | 1.35 | 1.39 | 0.279 | 0 | 1.2 |
| 15 | 18.3 | 21.2 | 17.5 | 18.3 | 44.8 | 0.3 | 24.0 |
| 30 | 29.9 | 36.9 | 26.7 | 28 | 54 | 0.5 | 35.1 |
| 60 | 16 | 25.4 | 19.5 | 20.3 | 40.8 | 1.0 | 24.4 |
| 90 | 10.7 | 25.3 | 20.2 | 21.1 | 25.3 | 1.5 | 20.5 |
| 120 | 24.3 | 23.2 | 24.5 | 25.6 | 13.5 | 2.0 | 22.2 |
| 150 | 20.1 | 23.8 | 25.7 | 26.9 | 10.4 | 2.5 | 21.4 |
| 180 | 21 | 22.4 | 19.2 | 20.1 | 8.72 | 3.0 | 18.3 |
| 240 | 33.9 | 20.9 | 12 | 22 | 7.67 | 4.0 | 19.3 |
| 300 | 22.4 | 17.4 | 13 | 13.5 | 17.3 | 5.0 | 16.7 |
| 420 | 9.19 | 21.8 | 5.03 | 5.24 | 21.4 | 7.0 | 12.5 |
| 540 | 6.27 | 20.1 | 14.5 | 15.1 | 15.2 | 9.0 | 14.2 |
| 720 | 8.25 | 7.31 | 4.38 | 4.57 | 6.08 | 12.0 | 6.1 |
| 1440 | 2.12 | 0.418 | 2.93 | 3.05 | 1.71 | 24.0 | 2.0 |
| Urine | 1.54 | 35.4 | 4.42 | 4.61 | 20.7 | | |

Following IV administration, a very rapid distribution phase is followed by a slower distribution or initial elimination phrase followed at approx 4 h by a prolonged elimination phase. The concentration-time profile of Mitoquinone-C10 was fitted to a three-compartment model with a terminal half-life of 1.8 h, although the half-life based on data called post 4 h dose is 14.3 h (Table 13).

Following oral administration, the absorption of Mitoquinone-C10 from the rat GI tract was fast. The peak plasma concentration of Mitoquinone-C10 occurred within 1 h of oral a administration and then declined slowly over time with an elimination half-life based on post 4 h data of about 14 h. The estimated F value is 12.4%.

TABLE 13

Pharmacokinetics of IV (P2) and Oral (P3) Mitoquinone-C10 mesylate-β- cyclodextrin 1:2) complex

3 compartment model

| Rat Code final value | A | SD | K1 final value | SD | B final value | SD | K2 final value | SD | C final value | SD | K3 final value | SD | r2 | A.I.C |
|---|---|---|---|---|---|---|---|---|---|---|---|---|---|---|
| P2 01 IV | 22766.1 | 12412.7 | 0.7080 | 0.1143 | 378.5 | 23.2 | 0.0456 | 0.0047 | 49.6 | 13.2 | 0.0057 | 0.0016 | 0.9999 | 69.21 |
| P2 02 IV | 2868.7 | 1502.0 | 0.3945 | 0.1855 | 591.0 | 325.4 | 0.0902 | 0.0317 | 105.0 | 26.2 | 0.0100 | 0.0024 | 0.9996 | 85.45 |
| P2 03 IV | 6736.1 | 1535.2 | 0.4168 | 0.0738 | 1029.7 | 248.0 | 0.0945 | 0.0128 | 72.2 | 11.4 | 0.0067 | 0.0013 | 0.9999 | 77.63 |
| P2 04 IV | 13002.7 | 880.7 | 0.3973 | 0.0198 | 591.4 | 96.3 | 0.0639 | 0.0092 | 88.5 | 13.7 | 0.0050 | 0.0010 | 1.0000 | 82.32 |
| P2 05 IV | 9353.2 | 943.4 | 0.4073 | 0.0257 | 510.0 | 80.0 | 0.0638 | 0.0094 | 50.4 | 14.0 | 0.0060 | 0.0020 | 0.9999 | 77.42 |
| Mean | 10945.3 | 3454.8 | 0.4648 | 0.0838 | 620.1 | 154.6 | 0.0716 | 0.0136 | 73.1 | 15.7 | 0.0067 | 0.0017 | 0.9999 | 78.4 |
| SD | 7573.8 | 5016.9 | 0.1362 | 0.0686 | 244.9 | 126.6 | 0.0204 | 0.0105 | 24.1 | 6.0 | 0.0020 | 0.0005 | 0.0001 | 6.1 |

2 compartment model

| Rat Code final value | A | SD | KI final value | SD | B final value | SD | K2 final value | SD | | A.I.C |
|---|---|---|---|---|---|---|---|---|---|---|
| P2 01 IV | 8722.0 | 2340.9 | 0.4962 | 0.0583 | 320.2 | 28.9 | 0.0267 | 0.0027 | 0.9990 | 96.46 |
| P2 02 IV | 2131.2 | 135.1 | 0.2295 | 0.0158 | 219.5 | 27.7 | 0.0199 | 0.0029 | 0.9986 | 97.56 |
| P2 03 IV | 4787.7 | 303.8 | 0.2642 | 0.0173 | 313.8 | 61.8 | 0.0289 | 0.0056 | 0.9990 | 108.04 |
| P2 04 IV | 10519.2 | 755.6 | 0.3306 | 0.0165 | 316.4 | 46.5 | 0.0203 | 0.0038 | 0.9992 | 117.86 |
| P2 05 IV | 7711.2 | 581.3 | 0.3466 | 0.0187 | 324.2 | 46.0 | 0.0317 | 0.0044 | 0.9995 | 100.53 |
| Mean | 6774.2 | 823.3 | 0.3334 | 0.0253 | 298.8 | 42.2 | 0.0255 | 0.0039 | 0.9991 | 104.1 |
| SD | 3324.2 | 881.7 | 0.1028 | 0.0185 | 44.53 | 14.17 | 0.0052 | 0.0012 | 0.0003 | 8.9 |

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The compounds of the invention have application in selective antioxidant therapies for human patients to prevent mitochondrial damage. This can be to prevent the elevated mitochondrial oxidative stress associated with particular diseases, such as Parkinson's disease or diseases associated with mitochondrial DNA mutations. They could also be used in conjunction with cell transplant therapies for neurodegenerative diseases, to increase the survival rate of implanted cells.

In addition, these compounds could be used as prophylactics to protect organs during transplantation, or ameliorate the ischaemia-reperfusion injury that occurs during surgery. The compounds of the invention could also be used to reduce cell damage following stroke and heart attack or be given prophylactically to premature babies, which are susceptible to brain ischemia. The methods of the invention have a major advantage over current antioxidant therapies they will enable antioxidants to accumulate selectively in mitochondria, the part of the cell under greatest oxidative stress. This will greatly increase the efficacy of antioxidant therapies.

Those persons skilled in the art will appreciate that the above description is provided by way of example only, and that different lipophilic cation/antioxidant combinations can be employed without departing from the scope of the invention.

The invention claimed is:

1. A chemically stable antioxidant compound, comprising:
a lipophilic cationic moiety linked by a linking moiety to an antioxidant moiety; and
an anionic complement for said cationic moiety,
wherein the cationic moiety is capable of mitochondrially targeting the antioxidant moiety,
wherein the anionic complement is a pharmaceutically acceptable anion that is not a halogen ion or a nitrate anion and is selected from the group consisting of an alkyl sulfonate, an aryl sulfonate, tetrafluoroborate, trifluoromethanesulfonate, hexafluoroantimonate, hexafluoroarsenate, hexafluorophosphate, tetraphenylborate, and tetra(perfluorophenyl)borate, and does not exhibit reactivity against the antioxidant moiety, the cationic moiety or the linking moiety, and wherein the antioxidant compound exhibits less than 10% decomposition after 60 days at 25° C., 50% relative humidity, the antioxidant compound having the general formula I:

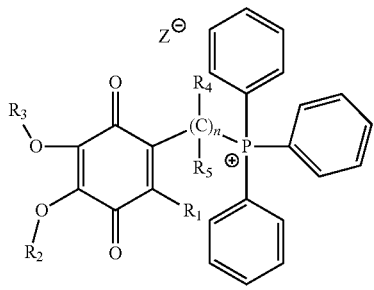

I or its quinol form, wherein $R_1$, $R_2$, and $R_3$ are the same or different and are selected from $C_1$ to $C_5$ alkyl, substituted $C_1$ to $C_5$ alkyl and H, wherein $R_4$ and $R_5$ are independently selected from the group consisting of H, hydroxyl, carboxyl, amide, unsubstituted or substituted alkyl, unsubstituted or substituted alkenyl and unsubstituted or substituted alkynyl, and wherein n is an integer from 2 to 20, and wherein Z is the anionic complement.

2. A compound according to claim 1 wherein the lipophilic cationic moiety is a substituted or an unsubstituted triphenylphosphonium cation.

3. The compound of claim 1 wherein the pharmaceutically acceptable anion is not a halogen ion.

4. The compound of claim 1 wherein the pharmaceutically acceptable anion is not nucleophilic.

5. The compound of claim 1 wherein the pharmaceutically acceptable anion is an alkyl sulfonate.

6. The compound of claim 1 wherein the pharmaceutically acceptable anion is selected from the group consisting of methanesulfonate, p-toluenesulfonate, ethanesulfonate, benzenesulfonate and 2-naphthalenesulfonate.

7. The compound of claim 1 wherein the pharmaceutically acceptable anion is methanesulfonate.

8. The compound according to claim 1 wherein the antioxidant moiety is a quinone or a quinol.

9. The compound according to claim 1 wherein the quinone or quinol antioxidant moiety is replaced with an antioxidant moiety that is selected from the group consisting of (i) vitamin E (ii) a chain breaking antioxidant, (iii) a fullerene, and (iv) a spin trap.

10. The compound according to claim 1 wherein the quinone or quinol antioxidant moiety is replaced with an antioxidant moiety that is selected from the group consisting of butylated hydroxyanisole, butylated hydroxytoluene, 5,5-dimethylpyrroline-N-oxide, tert-butylnitrosobenzene, tert-nitrosobenzene and α-phenyl-tert-butylnitrone.

11. The compound according to claim 1 wherein Z is selected from the group consisting of an alkyl sulfonate and an aryl sulfonate.

12. The compound according to claim 1 wherein C of $(C)_n$ is saturated.

13. A compound according to claim 1 having the formula:

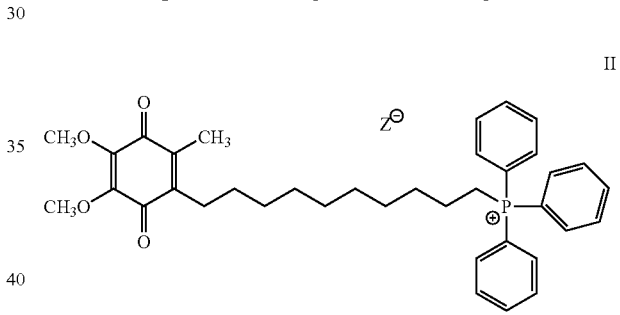

II or its quinol form, wherein Z is the anionic complement.

14. A compound according to claim 1 having the formula:

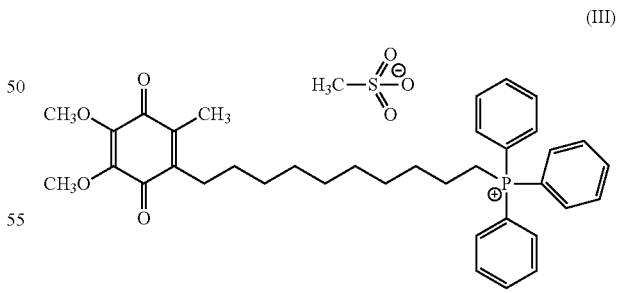

(III)

or its quinol form.

15. A pharmaceutical composition, comprising:
(a) a chemically stable antioxidant compound that comprises a lipophilic cationic moiety linked by a linking moiety to an antioxidant moiety;
an anionic complement for said cationic moiety, wherein the cationic moiety is capable of mitochondrially targeting the antioxidant moiety, wherein the anionic complement is a pharmaceutically acceptable anion that is not a halogen ion or a nitrate anion and is selected from the group consisting of an alkyl sulfonate, an aryl sulfonate, tetrafluoroborate, trifluoromethanesulfonate, hexafluoroantimonate, hexafluoroarsenate, hexafluorophosphate, tetraphenylborate, and tetra(perfluorophenyl)borate, and does not exhibit reactivity against the antioxidant moiety, the cationic moiety or the linking moiety, and wherein the antioxidant compound exhibits less than 10% decomposition after 60 days at 25° C., 50% relative humidity, the antioxidant compound having the general formula I:

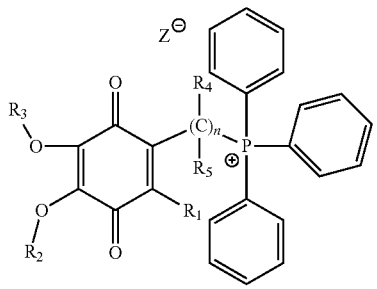

or its quinol form, wherein $R_1$, $R_2$, and $R_3$ are the same or different and are selected from $C_1$ to $C_5$ alkyl, substituted $C_1$ to $C_5$ alkyl and H, wherein $R_4$ and $R_5$ are independently selected from the group consisting of H, hydroxyl, carboxyl, amide, unsubstituted or substituted alkyl, unsubstituted or substituted alkenyl and unsubstituted or substituted alkynyl, and wherein n is an integer from 2 to 20, and wherein Z is the anionic complement; and (b) a carrier or excipient.

16. The pharmaceutical composition of claim 15 wherein the lipophilic cationic moiety is a substituted or an unsubstituted triphenylphosphonium, cation.

17. The pharmaceutical composition of claim 15 wherein the pharmaceutically acceptable anion is selected from the group consisting of (i) an alkyl sulfonate, (ii) a pharmaceutically acceptable anion that is not a halogen ion, and (iii) a pharmaceutically acceptable anion that is not nucleophilic.

18. The pharmaceutical composition of claim 15 wherein the pharmaceutically acceptable anion is selected from the group consisting of methanesulfonate, p-toluenesulfonate, ethanesulfonate, benzenesulfonate and 2-naphthalenesulfonate.

19. The pharmaceutical composition of claim 15 wherein the pharmaceutically acceptable anion is methanesulfonate.

20. The pharmaceutical composition of claim 15 wherein the quinone or quinol antioxidant moiety is replaced with an antioxidant moiety that is selected from the group consisting of (i) vitamin E, (iii) a chain breaking antioxidant, (iii) a fullerene, and (iv) a spin trap.

21. The pharmaceutical composition according to claim 15 wherein Z is selected from the group consisting of an alkyl sulfonate and an aryl sulfonate.

22. The pharmaceutical composition according to claim 15 wherein C of $(C)_n$ is saturated.

23. The pharmaceutical composition according to claim 15 wherein the compound has the formula:

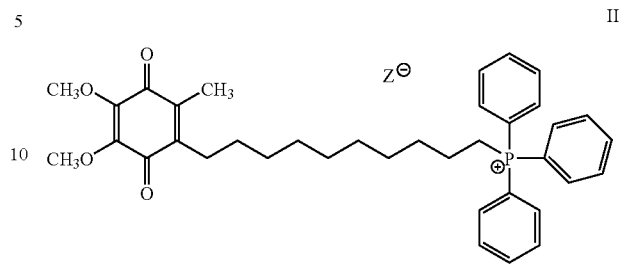

or its quinol form, wherein Z is the anionic complement.

24. The pharmaceutical composition according to claim 15 wherein the compound has the formula:

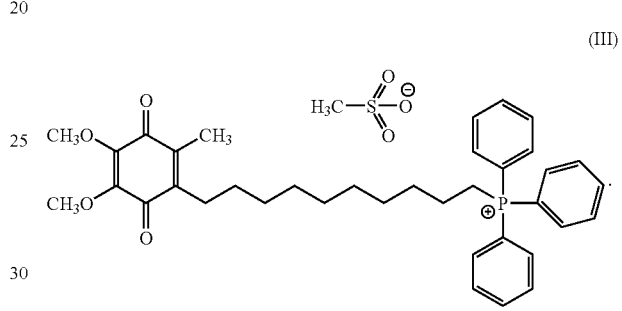

25. The pharmaceutical composition according to either claim 23 or claim 24 which comprises cyclodextrin.

26. The pharmaceutical composition of claim 25 wherein the compound and cyclodextrin are present at a compound-to-cyclodextrin molar ratio that is from about 10:1 to about 1:10.

27. The pharmaceutical composition of claim 25 wherein the compound and cyclodextrin are present at a compound-to-cyclodextrin molar ratio that is selected from the group consisting of (i) from about 5:1 to about 1:5, (ii) from about 4:1 to about 1:4, (iii) from about 2:1 to about 1:2, (iv) about 1:1 and (v) about 1:2.

28. The pharmaceutical composition according to claim 25 wherein the cyclodextrin is β-cyclodrextrin.

29. The pharmaceutical composition according to claim 24 which comprises cyclodextrin wherein the compound and cyclodextrin are present at a compound-to-cyclodextrin molar ratio that is about 1:2.

30. The pharmaceutical composition according to claim 15 that is selected from the group consisting of a pharmaceutical composition that is formulated for oral administration and a pharmaceutical composition that is formulated for parenteral administration.

31. The pharmaceutical composition according to claim 24 which comprises cyclodextrin, and that is selected from the group consisting of a pharmaceutical composition that is formulated for oral administration and a pharmaceutical composition that is formulated for parenteral administration.

32. A method of reducing oxidative stress in a cell, comprising:
contacting a cell that comprises mitochondria with a chemically stable antioxidant compound that comprises (i) a lipophilic cationic moiety linked by a linking moiety to an antioxidant moiety, and (ii) an anionic complement for said cationic moiety, wherein the cationic moiety is capable of mitochondrially targeting the antioxidant moiety, wherein the anionic complement is a pharmaceutically acceptable anion that is not a halogen ion or a nitrate anion and is selected from the group consisting of an alkyl sulfonate, an aryl sulfonate, tetrafluoroborate, trifluoromethanesulfonate, hexafluoroantimonate, hexafluoroarsenate, hexafluorophosphate, tetraphenylborate, and tetra(perfluorophenyl)borate, and does not exhibit reactivity against the antioxidant moiety, the cationic moiety or the linking moiety, and wherein the antioxidant compound exhibits less than 10% decomposition after 60 days at 25° C., 50% relative humidity, under conditions and for a time sufficient for accumulation of the antioxidant compound in the mitochondria, and thereby reducing oxidative stress in the cell, the antioxidant compound having the general formula I:

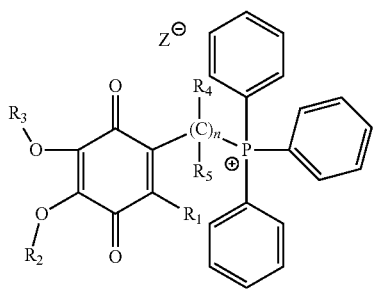

or its quinol form, wherein $R_1$, $R_2$, and $R_3$ are the same or different and are selected from $C_1$ to $C_5$ alkyl, substituted $C_1$ to $C_5$ alkyl and H, wherein $R_4$ and $R_5$ are independently selected from the group consisting of H, hydroxyl, carboxyl, amide, unsubstituted or substituted alkyl, unsubstituted or substituted alkenyl and unsubstituted or substituted and wherein n is an integer from 2 to 20, and wherein Z is the anionic complement.

33. The method of claim 32 wherein the lipophilic cationic moiety is a substituted or an unsubstituted triphenylphosphonium cation.

34. The method of claim 32 wherein the pharmaceutically acceptable anion is selected from the group consisting of (i) an alkyl sulfonate, (ii) a pharmaceutically acceptable anion that is not a halogen ion, and (iii) a pharmaceutically acceptable anion that is not nucleophilic.

35. The method of claim 32 wherein the pharmaceutically acceptable anion is selected from the group consisting of methanesulfonate, p-toluenesulfonate, ethanesulfonate, benzenesulfonate and 2-naphthalenesulfonate.

36. The method of claim 32 wherein the pharmaceutically acceptable anion is methanesulfonate.

37. The method of claim 32 wherein the quinone or quinol antioxidant moiety is replaced with an antioxidant moiety that is selected from the group consisting of (i) vitamin E (iii) a chain breaking antioxidant, (iii) a fullerene, and (iv) a spin trap.

38. The method of claim 32 wherein Z is selected from the group consisting of an alkyl sulfonate and an aryl sulfonate.

39. The method of claim 32 wherein C of $(C)_n$ is saturated.

40. The method of claim 32 wherein the antioxidant compound has the formula:

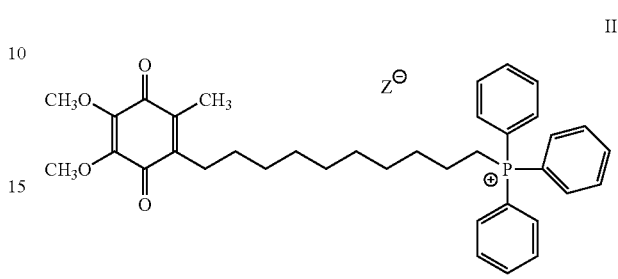

or its quinol form, wherein Z is the anionic complement.

41. The method of claim 32 wherein the antioxidant compound has the formula:

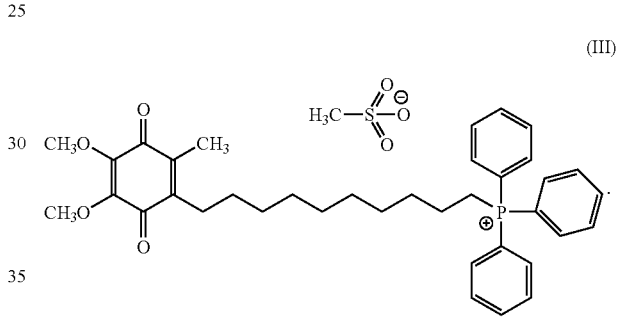

42. The method of either claim 40 or claim 41 wherein the antioxidant compound is present in a pharmaceutical composition that further comprises a carrier or excipient, wherein said carrier or excipient comprises cyclodextrin.

43. The method of claim 42 wherein the antioxidant compound and cyclodextrin are present at a compound-to-cyclodextrin molar ratio that is from about 10:1 to about 1:10.

44. The method of claim 42 wherein the compound and cyclodextrin are present at a compound-to-cyclodextrin molar ratio that is selected from the group consisting of (i) from about 5:1 to about 1:5, (ii) from about 4:1 to about 1:4, (iii) from about 2:1 to about 1:2, (iv) about 1:1 and (v) about 1:2.

45. The method of claim 42 wherein the cyclodextrin is β-cyclodextrin.

46. The method of claim 42 wherein the compound and cyclodextrin are present at a compound-to-cyclodextrin molar ratio that is about 1:2.

47. A method of preparing an antioxidant compound that is capable of reducing oxidative stress in a cell, comprising admixing cyclodextrin or a cyclodextrin derivative that is selected from β-cyclodextrin, sulfobutylcyclodextrin, maltosylcyclodextrin, and hydroxypropylcyclodextrin, with a compound of the formula I

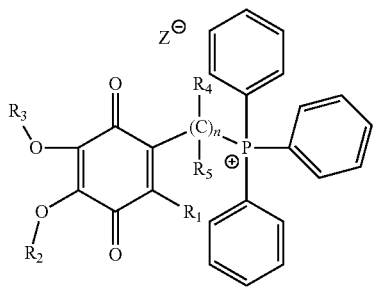

or its quinol form, wherein $R_1$, $R_2$, and $R_3$ are the same or different and are selected from $C_1$ to $C_5$ alkyl, substituted $C_1$ to $C_5$ alkyl and H, wherein $R_4$ and $R_5$ are independently selected from the group consisting of H, hydroxyl, carboxyl, amide, unsubstituted or substituted alkyl, unsubstituted or substituted alkenyl and unsubstituted or substituted alkynyl, wherein n is an integer from 2 to 20, wherein Z is a pharmaceutically acceptable anion that is not a bromide ion or a nitrate anion and does not exhibit reactivity against any moiety of the compound of formula I, and wherein the compound exhibits less than 10% decomposition after 60 days at 25° C., 50% relative humidity.

48. A method of preparing an antioxidant compound that is capable of reducing oxidative stress in a cell, comprising admixing cyclodextrin or a cyclodextrin derivative that is selected from β-cyclodextrin, sulfobutylcyclodextrin, maltosylcyclodextrin, and hydroxypropylcyclodextrin, with a compound having the formula:

(III)

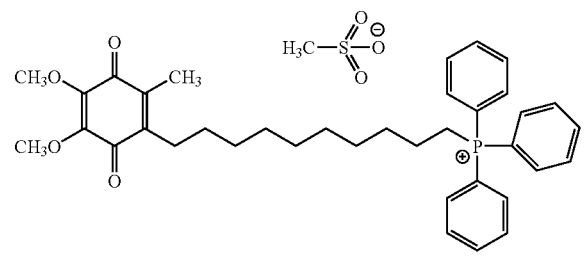

or its quinol form, wherein the compound exhibits less than 10% decomposition after 60 days at 25° C., 50% relative humidity.

49. A method of synthesis of a compound having the formula (III)

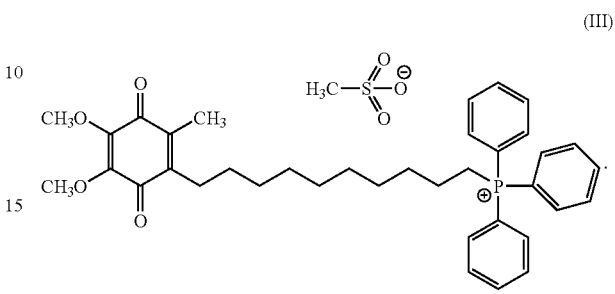

or its quinol form, said method comprising reacting idebenol mesylate with triphenylphosphine, wherein the compound exhibits less than 10% decomposition after 60 days at 25° C., 50% relative humidity.

50. The method of claim 49 which comprises chemically reducing idebenone mesylate to obtain idebenol mesylate prior to the step of reacting the idebenol mesylate with triphenylphosphine.

51. The method of claim 49 further comprising, prior to the reaction of idebenone mesylate with triphenylphosphine, the steps of:

(a) adding triethylamine to an idebenone solution to obtain an idebenone triethylamine mixture;

(b) cooling the idebenone triethylamine mixture of (a); and

I reacting the idebenone triethylamine mixture with a methanesulfonyl chloride solution to obtain idebenone mesylate.

52. The method of claim 51 comprising at least one of:

(i) step (a) wherein adding triethylamine comprises adding a molar excess of triethylamine relative to idebenone, (ii) step (b) wherein cooling comprises cooling to 10±3° C., and (iii) step I wherein reacting comprises reacting at approximately 10-15° C.

* * * * *

UNITED STATES PATENT AND TRADEMARK OFFICE
CERTIFICATE OF CORRECTION

PATENT NO.            : 7,888,335 B2                                          Page 1 of 1
APPLICATION NO.       : 10/568655
DATED                 : February 15, 2011
INVENTOR(S)           : Kenneth Martin Taylor It is certified that error appears in the above-identified patent and that said Letters Patent is hereby corrected as shown below:

Column 63, Line 60:
"of (i) vitamin E, (iii) a chain breaking antioxidant, (iii) a" should read, --of (i) vitamin E, (ii) a chain breaking antioxidant, (iii) a--.

Column 65, Line 45:
"or substituted and wherein n is an integer from 2 to" should read, --or substituted alkynyl and wherein n is an integer from 2 to--.

Column 65, Lines 65-66:
"that is selected from the group consisting of (i) vitamin E (iii) a chain breaking antioxidant, (iii) a fullerene, and (iv) a spin" should read, --that is selected from the group consisting of (i) vitamin E (ii) a chain breaking antioxidant, (iii) a fullerene, and (iv) a spin--.

Signed and Sealed this
Fourth Day of October, 2011

David J. Kappos
*Director of the United States Patent and Trademark Office*